US006330831B1

(12) United States Patent
Lynnworth et al.

(10) Patent No.: US 6,330,831 B1
(45) Date of Patent: Dec. 18, 2001

(54) STREAM-CLEANED DIFFERENTIAL REFLECTION COEFFICIENT SENSOR

(75) Inventors: Lawrence C. Lynnworth, Waltham; Yi Liu, Bolton, both of MA (US)

(73) Assignee: Panametrics, Inc., Waltham, MA (US)

( * ) Notice: Subject to any disclaimer, the term of this patent is extended or adjusted under 35 U.S.C. 154(b) by 0 days.

(21) Appl. No.: 09/420,453

(22) Filed: Oct. 18, 1999

Related U.S. Application Data
(60) Provisional application No. 60/104,913, filed on Oct. 20, 1998.

(51) Int. Cl.[7] .................................................. G01F 1/66
(52) U.S. Cl. ............................................... 73/861.28
(58) Field of Search .............................. 73/290 V, 589, 73/592, 597, 599, 629, 644, 602, 54.41, 64.53, 861.28, 861.27, 861.31

(56) References Cited

U.S. PATENT DOCUMENTS

| 4,320,659 | * | 3/1982 | Lynnworth et al. | 73/589 |
| 4,756,650 | * | 7/1988 | Smalling et al. | 73/861.28 |
| 4,787,252 | * | 11/1988 | Jacobson et al. | 73/861.28 |
| 4,829,833 | * | 5/1989 | Feller | 73/861.77 |
| 4,991,124 | | 2/1991 | Kline | 364/558 |
| 5,214,966 | | 6/1993 | Delsing | 73/861.28 |

FOREIGN PATENT DOCUMENTS 195 35 848
C1    9/1995  (DE).

* cited by examiner

*Primary Examiner*—Helen Kwok
(74) *Attorney, Agent, or Firm*—Nutter McClennen & Fish LLP

(57) ABSTRACT

An ultrasonic system employs a path through a fluid to determine fluid density by a differential reflection coefficient measurement of fluid impedance Z and a fluid sound speed c. Preferred configurations use clamp-on (external) transducers and combine ultrasonic measurements of flow velocity V over one or more paths, to obtain the mass flow rate. Z is determined by comparing reflections from a reference target, which may be totally reflective, with reflections from a sensor target having an effectively lower Z, which may be close to that of the fluid. Both targets are preferably located to be cleaned by the natural flow of the fluid. The low-Z target is interrogated at least once. Vee blocks provide a compact combination of reference and sensor targets that can be integrated with a velocity-sensing flowcell. Folded-path flow cells compactly measure V alone or in combination with density. The principal surface may be aligned parallel to the free stream direction and located to yield a flow value substantially equal to the area averaged flow, and the system may further correct for variations in the vicinity of the reflector.

16 Claims, 47 Drawing Sheets

Möbius strip

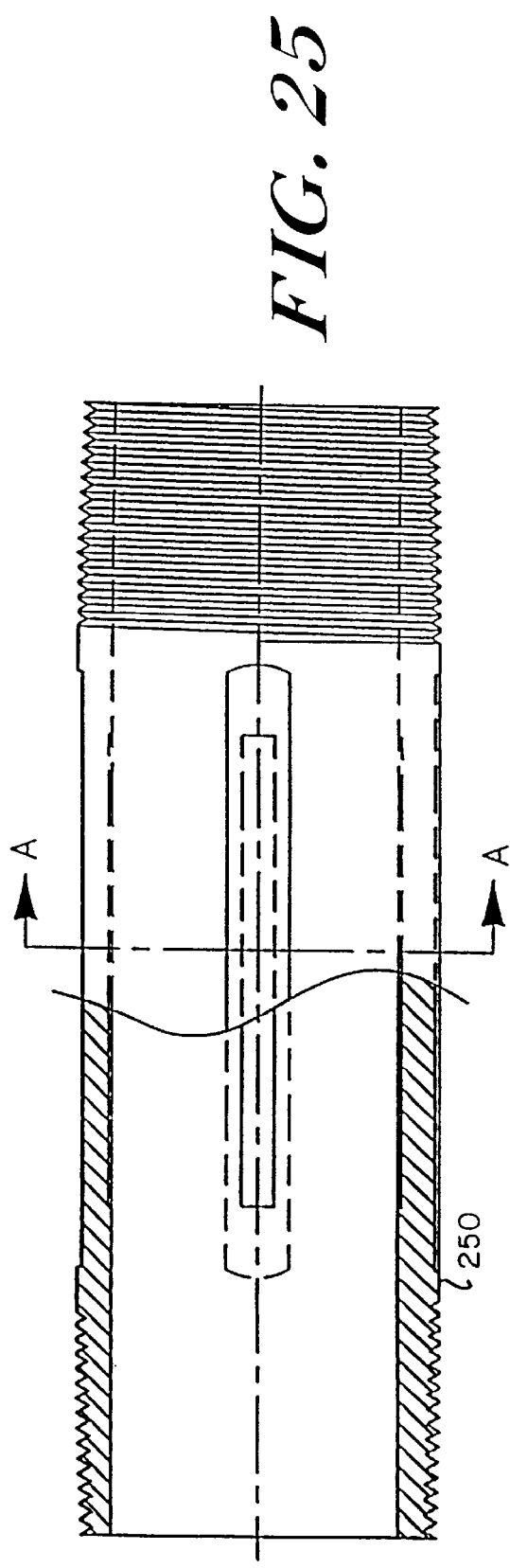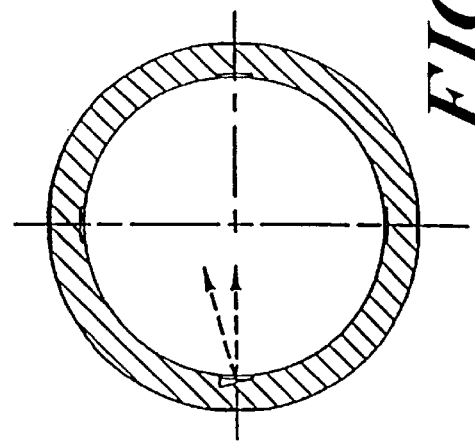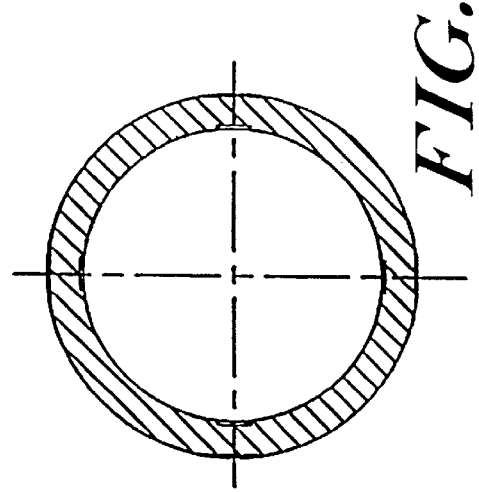

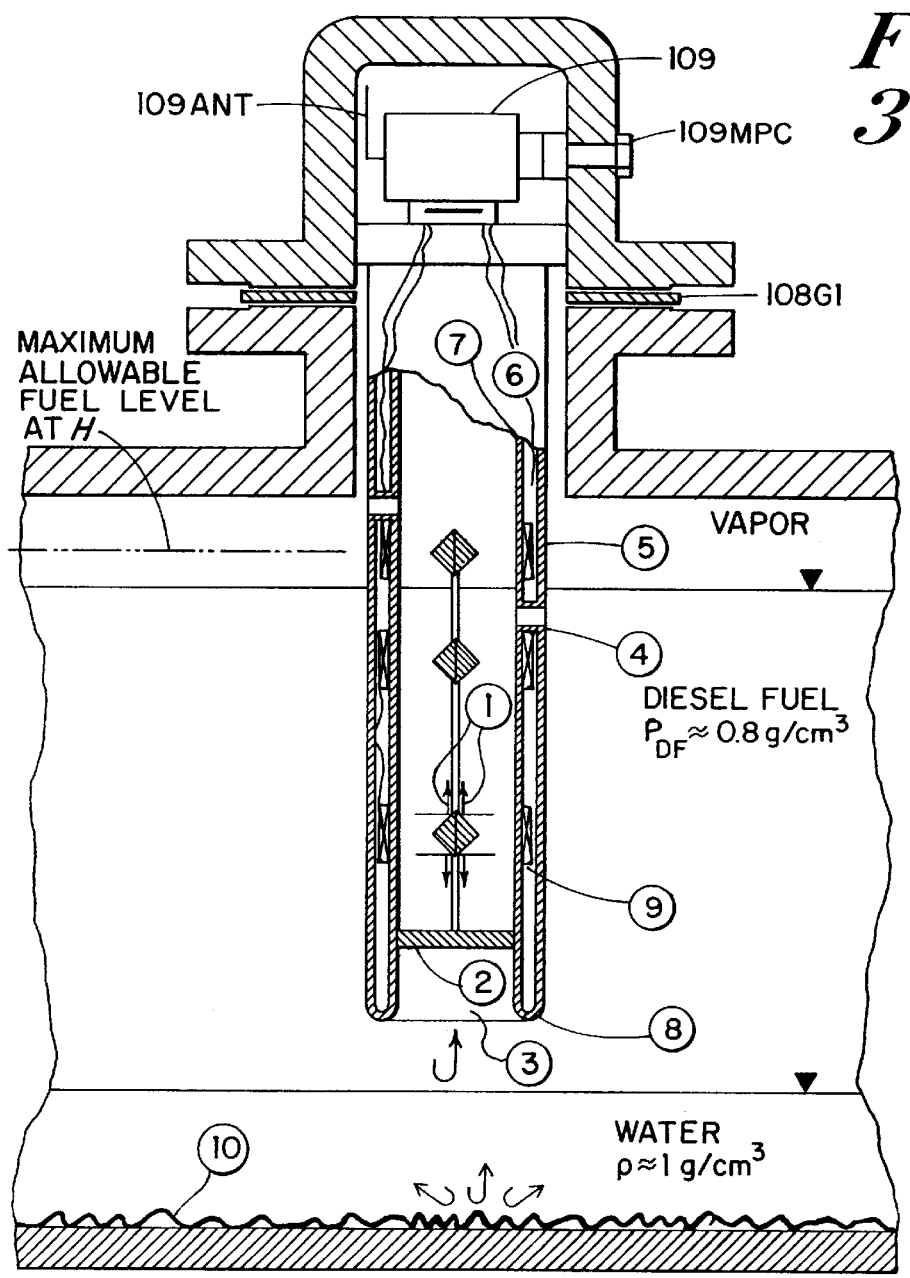

FIG. 30A

Legend:

① Echoes off 90 beam-splitting prism reflector. Right half of prism may be metal; left half, plastic.

② Spider support blade & axial rod attached thereto.

③ Part of reference path.

④ Sealed short-tube passageway through stillwell double wall.

⑤ Outer wall, e.g. 1" to 1.5" pipe, optionally threaded @ one or both ends.

⑥ Potting and damping.

⑦ Inner wall o1 cm to 1 inch.

⑧ End welded closed.

⑨ Piezo disks at same height as prism reflector.

⑩ Debris

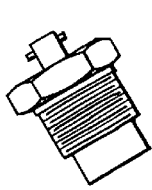
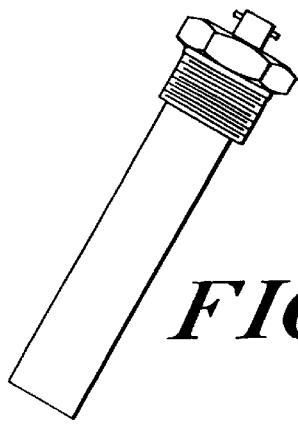
*FIG. 33B*  *FIG. 33C*
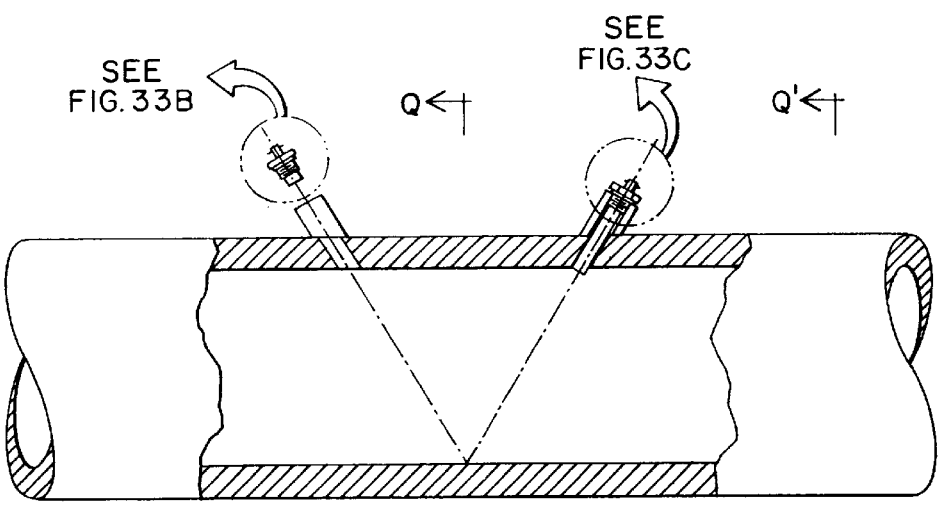
*FIG. 33A*
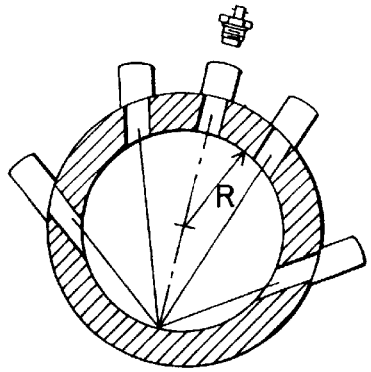   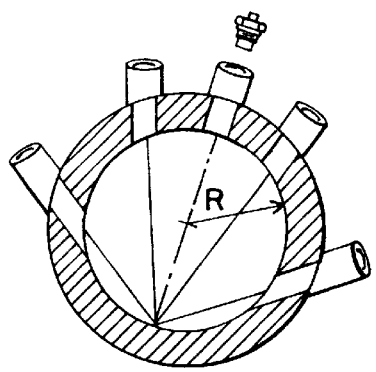
*FIG. 33D*   *FIG. 33E*

STREAM-CLEANED DIFFERENTIAL REFLECTION COEFFICIENT SENSOR

This application claims benefit of Prov. No. 60/104,913 filed Oct. 20, 1998.

BACKGROUND

This invention relates in general to ultrasonic measurement systems for ascertaining density or other characteristics of a fluid. More particularly, it relates to determining density of fluids flowing in pipes, including fluids like liquids, gases, and some two-phase combinations or mixtures.

It has been recognized in the ultrasonic literature since the 1960s, and perhaps earlier, that by measuring the acoustic impedance and sound speed of a fluid, one can determine the fluid density, dividing the impedance by the sound speed. In the prior art it is also known that impedance can be obtained from reports of the reflection coefficient at a fluid/solid reflecting interface. The 1982 U.S. Pat. No. 4,320,659 for Ultrasonic System for Measuring Fluid Impedance or Liquid Level of inventors Lynnworth, Seger and Bradshaw, teaches, in connection with FIGS. 4–9 thereof, that the reflecting surface should be substantially flush with the interior surface of the vessel or conduit in which the reflection coefficient is measured. The clamp-on systems of those figures used the existing internal wall of the vessel as the surface at which R is sensed. This sensor was minimally intrusive, and thereby minimally disturbed the process operations or the flow, and introduced little pressure drop. Generally, since a protrusion could be a site for buildup, an intrusive reflector is viewed as undesirable. This idea of flush mounting a reflecting surface is still prevalent, and is found in several recent technical papers on the subject, examples being Van Deventer and Delsing, 1997, An Ultrasonic Density Probe, pp. 871–875 in *Proc. 1997 IEEE Ultrasonics Symposium*, and the peer-reviewed paper by Adamowski, Buiochi and Sigelmann, Ultrasonic Measurement of Density of Liquids Flowing in Tubes, *IEEE Trans UFFC* 45 (1), pp. 48–56 (January 1998). These two papers may be taken to represent the current teaching in this field regarding reflective determinations of fluid density. They also teach that, to achieve sensitivity to fluid density, the characteristic acoustic impedance ($Z_0$) of the reflector should be comparable to that of the fluid. The $Z_0$ of many liquids is on the order of one to two mks rayls, water having a value of 1.5 in these units. If one scans a handbook of physics table of characteristic acoustic impedances of solids, one finds $Z_0$ of about 2 to 3 for plastics, and about 17 to 50 for commonly-used metals. This leads one to select a plastic as the reflector. If a metal were to be used, the reflection coefficient R at a metal/fluid interface is typically so close to unity, that the small changes in fluid density that are of interest would be very difficult to detect, let alone measure with high accuracy. This would lead one to conclude that using a metal reflector would not be of much practical use in a reflectometer designed for sensing fluid density. This would appear particularly true for a metal such as stainless steel (SS), having $Z_0$ about 45 mks rayls, or nickel, with $Z_0$ of 54 mks rayls. In the 1982 '659 patent mentioned above, a high-$Z_0$ sensor is shown.

Nonetheless, there remains a need for sensing or determining fluid properties, such as density, or properties such as mass flow rate, that depend on density.

OVERVIEW OF THE INVENTION IN RELATION TO THE ART

The present invention provides improved density or related fluid measurements through reflection of one or more signals from specially configured or positioned reflectors. Applicant surprisingly finds high-Z metal reflectors to be particularly useful as key parts of a density sensing system, when used in certain novel configurations. In exemplary embodiments: (a) the high-Z reflector provides, even at normal incidence, a useful reference echo amplitude nearly independent of the fluid impedance and the reflector temperature; (b) an even better reference echo is obtained at sufficiently oblique angles of incidence, e.g. 45°, which may for example be achieved in a vee block internal right-angled corner reflector. Applicant utilizes the fact that metal generally has a sound speed so much greater than that of the fluid that total internal reflection within the fluid occurs at angles of incidence between about 30 and 75° to provide a reference echo from the metal that is substantially independent of fluid impedance and reflector temperature. As a third example: (c) through impedance transformation, a high-Z material is made to behave like a low-Z plastic, yet retain better stability than a plastic over a temperature range, and, unlike some plastics, not absorb or change characteristics when immersed in fluid for extended periods.

In some instances an exceptionally robust system of the invention is made by combining the reflection principles with transmission principles. To illustrate this idea we may consider dry steam at high temperature and high pressure. In one such combination, sound speed is measured accurately in the dry steam, along with pipe wall temperature, without requiring penetration of the pipe. (The pipe wall temperature can be determined from the speed of sound in the wall, which is determinable from the arrival time of the pipe-borne noise, sometimes called short circuit noise or crosstalk.) From such measurements of speed of sound in steam at a known (measured) temperature, the pressure in dry steam is calculable. We shall take the steam temperature to be equal to the pipe wall temperature. From the steam pressure and temperature, steam density is obtained, by reference to steam tables. This provides a useful cross-check on the density obtained by reflection, and so yields a better, more robust mass flowmeter for dry steam. In the example just cited, transmission principles are used not merely as an algebraic equivalent related to the basic energy coefficient equation T+R=1.

Other embodiments of a system provide robustness through redundancy. One can, for example, install in the fluid, by means of a spoolpiece or other known means, a wave guide in which a torsional or flexural or breathing-mode guided wave has a phase velocity that slows down as the density of the surrounding fluid increases. This provides an average density over the sensing length of that wave guide in the fluid, typically across the diameter. Sometimes just the speed of sound across such a diameter path provides a reasonably accurate measure of average fluid density over that path. Sometimes the temperature of the fluid provides the density information, if the fluid composition is known well enough.

A problem with prior-art flush mounted reflection coefficient sensors is that they are easily fouled, when placed in a residue-bearing fluid, because the low flow at the walls (theoretically zero), allows settling of sediment or debris. Fouling can also take the form of microbubbles attaching to the wall, yielding a reflection coefficient that is not representative of the fluid average density. However, if the fluid is clean and does not deposit residue or microbubbles, then it may be acceptable for the reflecting surface to be at the inner wall of the pipe, or very near that wall. The debris problem may be addressed by directing a high-intensity beam of ultrasound towards the reflector, cleaning it by creating acoustic streaming over the reflector; if the beam is focused it may cause cavitation at or near the reflector. Recognizing that steam is often used for cleaning, one can surmise that a pipe conveying dry steam may indeed remain clean and a flush-mounted reflectometer could be expected to not become fouled. Even with presumably clean fluids, however, to avoid bubble or residue problems at the pipe wall, it is advisable to not utilize the very top or very bottom regions, respectively. This is often expressed in a guideline for installations that one should avoid the six and twelve o'clock positions. Instead, sensors are preferably installed between 1 and 5 o'clock or between 7 and 11 o'clock positions. Applicant notes that if the reflection coefficient is to be utilized to determine fluid density, reflections should preferably be generated in regions where the local fluid density is representative of the average density. This preference yields a representative fluid density. It is to be understood that while some of the drawings that follow, indeed show transducers or reflectors at the top or bottom of a pipe, these views can be interpreted as rotated cross sections. In practice applicant contemplates a typical rotation corresponding to one bolt hole of a flange. This means if the flange has twelve bolt holes, and if it were installed "one hole on top," then top and bottom problems are avoided by having the transducer and reflector rotated away by 30 degrees from the undesirable locations. More often flanges are installed "two holes on top," in which case the rotation would be a net amount of 15°, in this twelve bolt hole example.

Making a reflector from plastic as recommended in the above-cited 1997 and January 1998 papers has several advantages. There are, however, two problems of using a plastic material for the sensor. Plastics are not always of uniform density, and their density and sound speed are strongly temperature dependent. Density and sound speed temperature dependence affects the reflection coefficient. In turn, this requires complicated compensation, which may be aggravated in part by the typically low thermal conductivity of plastics (compared to metals like SS or Ti) which allows large temperature gradients to occur within a plastic reflector, especially during thermal transients. Some plastics are hygroscopic, and would introduce confounding variations from this mechanism. Further, if a plastic is subjected to very low pressure, it can outgas. In some space applications, devices cannot be used in zero-g orbits if they contain plastics that outgas and if the outgassing products could deposit on lenses of nearby optical equipment. This is another manifestation of instability. Some plastics, of course, have been developed to achieve stability. Among the more stable types one can choose from Rexolite, PEEK, polyamide, or others recommended for high temperature and corrosive service. In addition to plastics, porous graphite, when sealed by nickel, becomes a stable, low-Z reflector material, and its sound speed is nearly independent of temperature, especially over temperatures typically encountered in industrial processing of fluids. ATJ and other commercial grades of porous graphite have shear wave sound speeds near 1500 m/s, comparable to the sound speed in water and in many industrial liquids (e.g., gasoline, c≈1100 m/s). Impedance and sound speed will figure prominently in the discussion below, and thus, in many instances below, the term "plastics" will be understood to include materials like graphite whose characteristic impedance is comparable to typical plastics, and whose c is desirably low, under about 2000 m/s. Applicant also contemplates chalcogenide glasses for their low shear wave sound speeds, and certain silicate glasses identified in the IEEE Ultrasonics Symposium presentation of J. I. Kushibiki et al, Sendai, Japan, (Oct. 8, 1998).

The present invention includes novel uses of materials like plastics, graphite or chalcogenide glasses as reflectors, for example, using them at oblique incidence in a manner that allows a substantial fraction of incident energy from a fluid to proceed into the plastic as a shear wave and thereby provide a magnified measure of fluid density. Applicant also increases energy transmission into an immersed plastic at 45° oblique incidence, compared to normal incidence, to improve sensitivity to density. This effect is particularly enhanced when the plastic has the shape of a vee block, allowing double reflection and efficient participation in a mass flow measurement. It will be understood that a metal vee block, itself totally reflective in this situation, when coated by an attenuating plastic, can be converted to a sensitive density-responsive sensor. One embodiment includes a metal vee block, partly bare, partly plastic coated, which provides differential reflectivities in a compact device. Applicant utilizes the ratio of reflectivities as a measure of fluid impedance, which after compensation for fluid sound speed, yields fluid density.

In several preferred embodiments, by placing the reflector in the freestream, fouling is much reduced, and when thermal transients occur, the high flow accelerates the restoration of thermal equilibrium, for reflectors made of plastic or metal, or of two part, metal/plastic construction. In one implementation, the reflector is an axially-oriented sting of robust construction configured to lie essentially on the axis of a pipe, which is interrogated from one or more points on the pipe, e.g. from four quadrants around the circumference. The reflector is placed in the flowing stream on axis, i.e., at the very center, or the location of the maximum flow velocity. This arrangement provides a simple system for sensing density, and for checking on the symmetry, or lack thereof, of flow. An axial sting reflectometer sensor may be formed of adjacent thin rod segments made of SS and plastic, threaded together, each of diameter 1 to 3 mm and each of length 10 to 30 mm. Diameters and lengths need not be equal. The axial location corresponds to y/R≈1, the equality being only approximate due to the finite diameter of the sting, whose reflecting surface(s) are not exactly at the axis. In this expression y is the distance in from the wall, and R is the pipe internal radius, a notation customary in fluid dynamics.

As described further below, several preferred locations for the reflector achieve "washing," and further, achieve a sampling of the flow in such a way that bidirectional oblique interrogation of the reflecting surface yields sufficient data for determining the average flow velocity. Below, the term differential reflector is taken to mean two or more reflectors having different acoustic impedances, e.g. SS and plastic. Accordingly their reflectivities differ. Depending on context the term will also, or alternatively, mean reflectors placed at different distances in from the wall. One of these positions can indeed be the very center, which has the feature that the path integral to that position corresponds to the well known path integral of flow measured along a tilted diameter, a path employed in the usual ultrasonic contrapropagation flow meters, provided the flow is axisymmetric. Flow asymmetry is compensated by measuring from two or more points around the pipe periphery. Another reflector position of special interest found by recent calculations for a rough wall profile given by Pao's equation, is at the normalized distance in from the wall of y/R=0.58, approximated by 0.6. (The symbol R is also employed below to denote the reflection coefficient. If the meaning would not be clear from the context, an appropriate subscript will be added, e.g., $R_{radius}$ when referring to the pipe radius.)

One of the discoveries of this invention, is that by coating a high-impedance reflector with a quarter wave thickness of intermediate impedance, an input impedance can be created that has a substantially lower value than that of the base material. This can be done locally, or over an extended strip region or even over the entire inside surface of a section of the pressure-bounding pipe or section of a reflector, as described below in connection with a low-Z-lined spoolpiece. We may refer to the resulting structure as an impedance-transformed reflector. For example, the acoustic impedance of SS can be transformed to behave acoustically like a plastic, with respect to reflectivity, by adding to it a quarter wave surface layer of fused silica or quartz. An economical way of achieving this transformation, is to bond in a standard piezoelectric blank of quartz, say a 1-MHz disk, interrogated at 0.5 MHz. To transform SS to an even lower acoustic impedance, applicant has made the quarter wave layer of a syntactic foam. If interrogation is oblique, a slight shift in the interrogation frequency or the thickness is required, compared to parameters for interrogation at normal incidence. As a numerical example, in the case of a syntactic foam transformation coating, applicant found that the thickness theoretically ought to be increased by about four percent or about one thousandth of an inch, for oblique 60° interrogation at 500 kHz. It will be understood that for ease of description below, reflectivity explanations generally are given as if interrogation were at normal incidence. Other plastic transformers may be implemented by placing a plastic tube liner inside a steel pipe to enhance the wall reflection, or centrifugally casting a high-temperature plastic liner inside a metal pipe. In food or pharmaceutical processing the conduit is often glass or special plastic, and this may itself possess an adequately low acoustic impedance to not require transformation for application of the invention thereto. Nevertheless, by applying externally, a steel section, one can modify the traditional process conduit to achieve the two different reflectivities needed for certain practices of the invention, and this further provides a set of reflection measurements that may be processed to avoid drift as the transducer ages or as other parameters change uncontrollably over time.

For more exact descriptions of phenomena at oblique incidence, the somewhat more complicated equations appropriate to oblique incidence must be utilized, including generation, by mode conversion, of additional modes of ultrasonic waves. The "oblique incidence equations", sometimes referred to as Knott's or Zeoppritz' equations, yield the ratio of reflected to incident energy, or energy partition, as a function of angle of incidence. The equations are not very compact, but may be readily found in the literature of reflection seismology, nondestructive testing and elsewhere, so they need not be repeated here, beyond mention of the original papers: C. G. Knott, *Phil. Mag.* 48, p. 64 (1899); K. Zoeppritz, *Nachr. Akad.* Wiss. Göttingen, *Math. Phys.* Kl., IIa, p. 66 (1919). In applicant's description the term reflection coefficient means sound pressure reflection coefficient. It will be understood that the reflection coefficient in general is a complex number. It has an imaginary component that increases in magnitude as the fluid's viscous component increases. The imaginary term also depends on the angle of incidence, absorptive losses in the reflector, and the ultrasonic frequency. For low-viscosity fluids, which are often treated as inviscid (e.g., those having a kinematic viscosity below ten centistokes), for elastic reflectors and for many plastic reflectors, and for ultrasonic frequencies low enough to readily propagate across low-viscosity fluids (e.g., frequencies in the 0.5 to 5 MHz range), the reflection coefficient is substantially a pure real number. The explanation of elements of novelty in the present invention does not rely on any detailed understanding of the energy partition equations nor of the detailed influence of viscosity on reflections.

When the fluid is a clean gas at high pressure, at 100 bar, for example, reflection coefficient measurements of the type described, using external clamp-on transducers, become possible. At lower gas pressures, however, such as just one or a few bars pressure, the technical difficulties of attempting such measurements using clamp-on transducers are considerable. The difficulty may be said to have two parts: firstly, it is difficult to transmit efficiently through a steel pipe into a gas of low density (~1 to 10 kg/m$^3$); secondly, there is an interfering crosstalk noise component that easily travels around the pipe, which is generally much stronger than the gas-borne signal. Applicant reduces the difficulty by lining the pipe with a quarter wave matching layer applied as a local strip where radiation is sought, or by lining the entire pipe inner wall. An epoxy or syntactic foam lining less than or about one millimeter thick is suitable for frequencies on the order of 500 kHz. As a numerical example, if the sound speed in the lining is 2000 m/s=2 mm/$\mu$s, then the wavelength in the lining at 500 kHz is 4 mm. The quarter wave thickness is 1 mm. This quarter wave low-Z-lining remedy increases the transmission coefficient into and out of the pipe, and at the same time, provides a reflection coefficient at the lined (or matched) wall region that is much more sensitive to the fluid impedance than would be possible if the lining or strips were absent. One configuration implementing these features, is a plastic-lined (or low-Z-lined) spool piece that can be calibrated as a mass flow meter, with transducers outside the pressure boundary. The external transducers may be welded or otherwise permanently attached to the outside surface of the pipe portion of the spool piece, to eliminate coupling variations that otherwise might be present with clamp-on transducers.

Below, applicant describes embodiments of the invention wherein normal incidence shear waves provide a completely-reflected reference echo from the solid/fluid interface, while longitudinal waves provide a density-responsive echo.

In some embodiments, the support structure for the density-responsive reflecting element has a second purpose with regard to flow measurement. The support can condition the flow for more accurate flow measurement downstream. This is an alternative solution to the problem of determining mass flow rate, somewhat different from obtaining flow information directly off the density-responsive sensor itself, by the path integral method.

Other combinations of interest are structures where a secondary component of flow is detected. Thus, cross flow or circulation (swirl) is sensed in a region generally perpendicular to the conduit axis, where that flow measurement involves one or more traverses that yield a received or reflected amplitude responsive to a representative fluid density. Such structures are implemented in the present invention either built within a separate flange, or in a flange that is part of a mass flow meter spool piece. We may refer to such structures as flange-mounted densitometers, and they may be lined locally or over their entire inner surface with a quarter wave matching layer, to increase their sensitivity to fluid density. The pipe section between such flanges may provide one or more paths for ultrasonic flow measurements. Multipath configurations may be used, with diameter, midradius, Gauss-Chebyshev, or skewed paths between some of the foregoing planes. Applicant refers to these as diameter and off-diameter paths. It will be understood that the paths may be tilted in the axial direction to respond to flow components in that direction. Skewed paths may be achieved by creating a two-faceted notch within a conduit or flange, one facet refracting along a first path in the fluid, which could be the diameter or an off-diameter chord, while the second facet refracts along a different chordal path in the fluid. Novel Gauss Chebyshev set of paths which lie in skew planes and novel multifaceted notches are described further below in greater detail.

Multifaceted reflectors, or multifaceted transducers, can be arranged to sense in a very short L (where L=axial projection of the path), primary and secondary components of flow, combined with density sensing.

Among the known combinations of diameter and off-diameter paths, or sometimes just off-diameter paths, the quadrature methods exemplified by those in Wyler, U.S. Pat. No. 3,940,985 (Mar. 2, 1976), and in Malone and Whirlow, U.S. Pat. No. 3,564,912 (1971) are of special interest for accurate flow measurements. Midradius combinations are also of interest, for the same reason. In the '985 and '912 patents the quadrature paths lie in planes parallel to one another. Typically, in the prior art, when an even number of paths are used, half are distributed in one half of the pipe, say the upper half, and the others are symmetrically distributed in the other half of the pipe, say the lower half. The present invention finds a way to rotate the traditional quadrature paths such that the paths are still symmetrically distributed, for example, two on top, two on bottom, yet reduces the number of ports and the number of transducers each by a factor of two. We will refer to this as the rotated quadrature method. This new method offers the prospect of the high accuracy achievable with multipaths, yet at the low price associated with only two ports and two transducers. When combined with density measurements, the result is an accurate measure of mass flow rate. To render such rotated GC methods immune to secondary flow one typically additionally measures said secondary components by known means.

The present invention also contemplates using a multifaceted form of the bundle transducer described in Lynnworth and Liu, U.S. Pat. No. 5,962,790 or using other multi-element transducers, to also achieve multipath interrogations via only two ports and two transducer assemblies, either along GC chords or other chords, for example chords that project in the end view as a square or inscribed equilateral triangle.

Below, applicant discusses several ways of introducing the reflector, including: hot tapping; installation in a pipe tee, such as a two-inch tee; and installation in a pipe nozzle, e.g. a two-inch nozzle, which applicant has found appropriate for numerous pipe sizes in the range 3 to 12 inch nominal diameter. Constructions are favored where the transducers themselves are external and in some embodiments are removably mounted outside the pressure boundary. However, if the fluid is a gas at a low pressure, it may be necessary or advantageous in many cases to use wetted transducers (instead of clamp-on transducers). If the transducers are wetted, they can be impedance matched, and it will be shown how this can effectively enhance the sensitivity of a reflection coefficient measurement of fluid density that utilizes an amplitude measurement of the reflection from a remote reflector that can also be matched. In such embodiments, by matching both the wetted transducer and the reflector, one achieves a double effect, something like that described above for a corner reflector, or for the low-Z-lined pipe.

While the freestream location offers advantages with respect to keeping the reflecting surface clean, there are some potential drawbacks, especially if the fluid is a compressible medium such as air or steam, where freestream turbulence translates to amplitude jitter, making it hard to measure the reflection coefficient accurately. Devices in the freestream need to be adequately secured, to avoid vibration problems, especially at high flow rates. The accuracy of the overall measurement may be improved by purposely placing one portion of a two-reflector system, say a reference reflector, in a region of low flow (when the fluid is clean or fouling is unlikely), and utilizing the transit time, rather than the reflection amplitude, of the reflection from the second reflector interrogated over a path that includes free stream turbulence. This can be accomplished in the two-inch pipe tee configuration mentioned above.

Because the field of ultrasonic flow measurement is so diverse, there are a large variety of special situations. Particular sensor embodiments may satisfy some of these applications but not others. With respect to the broad objective of measuring mass flow rate according to the principles set forth in this application, a sensor arrangement wherein one reflectometer geometry yields density and flow velocity information will be considered a generally preferred configuration. That is, in preferred systems, at least one of the paths contributes to both density and flow velocity information, thereby efficiently utilizing transducers and structures for a mass flow determination.

Among the examples of preferred configurations is a compact solution to the problem of measuring mass flow rate at low flow rates. Here we have three technical problems: finding a robust solution to sensing (1) small changes in density; (2) small changes in flow velocity; while (3) achieving compactness. Applicant has found a folded path geometry that solves all three problems, in which ten or more reflections are utilized, to (1) enhance the sensing of small changes in reflection coefficient, and (2) increase the effective flow-sensing path to a numerical value>>ten times the conduit diameter. This solution retains a reference echo, and can even provide for simultaneous contrapropagation and/or redundant paths by using split crystals at each end of the interrogated path.

While preferred configurations are generally those in which both density and flow velocity are measured in one device, which may further include an integral electronics module, applicant also contemplates configurations wherein two devices are connected in series, one responding to density and flow over a first flow range, while the second responds to flow over another range. Such arrangements also offer redundancy. One compact example of combining density and flow sensing in one device is provided by a small hex pipe fitting such as a nipple or coupling (e.g. nominally one inch or 25.4 mm ID×~100 mm long) containing two 90° vee blocks positioned such that one, being plastic, yields a very sensitive measure of density, while the second, being metal, and interrogated such that total internal reflection occurs on the fluid side, yields strong signals unaffected by the density of the fluid but whose transit times with and against the flow are indeed sensitive to flow.

SUMMARY OF THE INVENTION

An ultrasonic system determines fluid density by a differential reflection coefficient measurement of fluid impedance Z and a fluid sound speed c. Preferred configurations use clamp-on (external) transducers and combine ultrasonic measurements of flow velocity V over one or more paths, to obtain the mass flow rate. Z is determined by comparing reflections from a reference target, which may be totally reflective, with reflections from a sensor target having an effectively lower Z, which may be close to that of the fluid. The targets may be located to be cleaned by the natural flow of the fluid. The low-Z target is interrogated at least once. Vee blocks provide a compact combination of reference and sensor targets that can be integrated with a V-sensing flowcell. Folded-path flow cells compactly measure V alone or in combination with density. A target including a flat or curved reflector may be situated at a point about 60% in from the wall towards the axis, defining a signal path to yield an average V. A short square or round tube reflector allows external sampling from four quadrants. Other discrete reflector targets may be distributed to yield density and V distributions. The invention also contemplates rotated quadrature paths configured to sample V in large pipes with multipath accuracy using only half the number of ports and of transducers of typical prior-art four-path flow meters. In a preferred embodiment, the quadrature paths may share a common reflection point. Multifaceted transducers may be utilized to sample over several paths from a single port, or with a minimum number of transducers. The differential reflector measurements are adapted to complex flow patterns and to stratified liquids in tanks.

The ultrasonic reflection coefficient sensor of the present invention may operate to provide multi-parameter data that is more representative of the fluid characteristics, than is possible with a prior art sensor situated in a stagnant or low-flow region. Preferably the sensor's principal surface is placed where flow is nonzero, so the sensor is washed by the fluid and, in the case of compressible fluids, responds to a representative fluid density. The sensor may be made of a strong metal such as titanium or stainless steel to achieve a nonabsorptive, substantially temperature immune and robust construction. When the characteristic acoustic impedance of the underlying reflector is larger than that of the fluid by a factor of ten or more, sensitivity to the sought measurand, e.g. fluid density, is preferably enhanced by one or more of: impedance matching the reflector system; interacting with two or more impedance-responsive reflecting regions, such as a corner reflector or the curved interior wall of a flange interrogated along an inscribed equilateral triangular or regular polygonal path; interacting with two surfaces having different input impedances to constitute a differential reflection coefficient sensor. When used to measure the axial component of flow, the principal surface is aligned parallel to the freestream direction and located such that the path integral from the wall to the reflector located at the normalized distance $y/R$~0.6 in from the wall yields a flow value substantially equal to the area averaged flow. A compensation means may be provided to correct for variations in properties of the reflector or the fluid in the vicinity of the reflector, and the reflector may be interrogated from outside the vessel, when the fluid is a liquid or a gas of high density, by configuring the system with internal impedance-matching strips or an impedance-matching lining that increases transmission between the metal pipe or vessel wall and the fluid (e.g., air or steam), and also increases the sensitivity of a reflection coefficient measurement of fluid density. Systems may configured so that the signals reflect off a multiplicity of reflecting surfaces to yield profile information, such as the distribution within a conduit of the fluid density, fluid temperature, fluid velocity, or combinations of these measurands. One such multiplicity of reflecting surfaces is implemented with a relatively short axisymmetric tube of square or round cross section, centrally installed within the conduit. The mass flow rate may be obtained as the product of average flow velocity, density and the duct area. If the duct is not full (of liquid) this is effected with a measurement of liquid level, which can be thought of as a measure of the density distribution, where that distribution includes a discontinuity at the liquid surface. Among the compact economical configurations of special interest, are those formed within a two-inch pipe tee, or within a two-inch pipe nozzle, the latter being adaptable to pipes up to about 12 inches in diameter. Another compact arrangement is a short sting, shaped like a nail, located on axis, and having portions of two different impedances. Still another compact arrangement includes a differential vee block within a small pipe fitting, modified slightly to accommodate transducers and to provide area averaging of flow. Still another compact arrangement fits transducers, reflectors and paths within the confines of a flange of normal or extra-thick construction. Folded path embodiments also accomplish the goal of a compact assembly. One of the differential arrangements is constructed using parts of relatively high acoustic impedance, but which, through impedance transformation, provides for two different reflectometer input impedances, which are fractionally greater and less than the set point impedance of the fluid by small amounts, such that the two resulting reflection coefficient magnitudes, as generated acoustically or after some adjustment for practical reasons, are equal only when the fluid impedance equals the set point value. This arrangement is useful in process control and sensor calibration procedures. One arrangement that combines multipath sensing of density and flow velocity under disturbed flow conditions is appropriate for valves. While the density sensor of this invention can be added to many prior-art flow sensors, there are particular advantages obtained when the combination of the two sensors is considered, such that optimized configurations are obtained. When placing the reflective density sensor in the freestream is not feasible for reasons such as abrasion, pressure drop or a need to tolerate "pigging" of the conduit, the reflector is stream-cleaned by acoustic streaming at or near the reflector's face, which may be achieved by focusing high-amplitude ultrasonic waves in that region, either continuously or at intervals effective to prevent or to undo fouling.

In one embodiment of the present invention, an ultrasonic system employs at least one reflector and measures the reflection coefficient R and sound speed C near the reflector at which R is measured, computing the fluid density from R and c. For measuring the fluid mass flow rate $M_F$, the system preferably measures flow velocity too, meaning the average flow velocity $V_{AVG}$, such that the product of density and average flow velocity, times the pipe area A, yields the mass flow rate. Details of the various embodiments of the invention relate to obtaining and maintaining a representative value of R, configuring the reflectors so that R is indeed sensitive to fluid density, and yet minimally disturbing the fluid flow. Because the measurement of the amplitude of the reflected echo can be subject to drift in the external transducer and electronics, as well as being influenced by attenuation over the fluid path to and from the reflector, some form of compensation appears essential. Applicant employs high-Z reflectors to accomplish a normalization, such that the ratio of echoes from two reflectors having substantially different reflectivities, yields an accurate measure of fluid density. Furthermore, by placing the two reflectors at slightly different distances from the transducers, a differential path measurement of sound speed c in the fluid in the immediate vicinity of the reflectors is obtained. By measuring c in this region, applicant computes density from the reflection coefficient. Preferred arrangements obtain the sought measurements with no ultrasonic transducers exposed to the fluid. That is to say, the transducers are clamped onto the pipe or are otherwise mounted external to the pressure boundary, i.e., bonded or welded to the pipe exterior for permanent coupling thereto. For an economical system the same transducers are used to determine both density and flow velocity. Likewise the same reflectors are used for both purposes, i.e., for density and flow velocity determinations, in preferred configurations. In some special circumstances, e.g., clean dry steam, the same conditions appropriate for maximizing transmission into the steam, may maximize the sensitivity of a reflection coefficient measurement of the steam density. This leads to special embodiments where a spoolpiece is lined with a quarter wave impedance matcher that can be substantially flush with the spoolpiece inside wall, or flush with the inside wall of upstream piping. This matcher remains clean, and facilitates the objective of permitting a reflection coefficient measurement responsive to steam density to be made without obstructing the steam flow. We may speak of this matcher as nonintrusive relative to the nominal ID of the adjacent piping. This special nonintrusive solution may be applied to other clean fluids, e.g. methane or clean air, and possibly to some anesthesia gases, if the pressure is high enough, such that mass flow rate can be obtained with minimal flow obstruction and with no electrically-energized components of the ultrasonic system within the pressure boundary. The electricity stays outside. The result is a safe and efficient measuring system.

Some configurations are particularly well suited for inclusion within a valve, and preferably form part of a mass flow control system. Designs for sensing density and V within the confines of a ball valve illustrate ways of dealing with complex, non-ideal flow patterns and nonparallel boundaries.

The systems for sensing density by reflecting from 45° reflectors may also be extended to certain 45° arrangements inside a perforated stillwell to implement upward-looking and downward-looking sensing of liquid level, which may be combined with density profiling, interface detection, avoidance of overfill, and sensing of fill rate from the rate of change in position of the density discontinuity at the liquid surface. The stillwell may be installed in an above-ground storage tank, a vehicular fuel tank, or other tank, well or sump. The reflective surfaces are preferably maintained clean by orienting these surfaces slanting down so that debris does not accumulate. The provision of self-cleaning reflectors is especially beneficial for sensing systems in applications normally subject to obscuring deposits, such as in diesel fuel tanks aboard locomotives or ships.

The fluid density is determined from an ultrasonic sound pressure reflection coefficient measurement, usually combined with additional data, such as sound speed in the fluid near the reflector; flow velocity of fluid in the region between the pipe wall and the reflector; reflections from a second reflector wetted structure or wetted surface within or adjacent the fluid (with the wetted structure or surface considered a reference reflector). The second reflector may be located at a different distance in from the pipe wall, compared to the distance that the first reflector is in from the wall, and the pair of them thereby provide a way to integrate the flow velocity along two different paths, such that the two integrals allow one to draw conclusions about the shape of the flow profile or allow one to compute the average flow compensated for flow profile. As each reflector yields information about fluid density adjacent itself, a multiplicity of reflectors yields information about the distribution of density. If the reflectors are suitably positioned, path integrals may provide by tomographic reconstruction or by other means, a picture of the flow distribution, integration of which yields the area-average flow velocity. From the two independent measurements of density distribution and flow velocity distribution, the processor may effectively multiply the two distributions to obtain an accurate measure of the mass flow rate distribution, which when integrated over the pipe area yields an accurate measure of total mass flow rate through the pipe. This integration system in principle also solves the problem of determining mass flow rate in a partly full pipe, yielding in that case an output proportional to the product of area times velocity times density. To complete the picture of the density distribution, R can be measured at the pipe wall by a combined L and S (longitudinal and shear wave) interrogation, for example with a wetted transducer. In these systems, the shear wave is entirely reflected and provides a reference, while the longitudinal wave reflection provides a measure of $\rho c$.

BRIEF DESCRIPTION OF THE DRAWINGS

These and other features of the invention will be understood from the description herein, taken together with illustrative drawings of representative embodiments, wherein

FIG. 25 is a side view of a spoolpiece for conveying clean gas, and containing impedance matching material at specific internal locations, and transducers at associated external locations;

FIG. 25A is an end view cross section showing recesses for impedance matching material at four circumferentially-spaced locations;

FIG. 25B is like FIG. 25A except the internal recesses are multifaceted to provide off-diameter chords instead of or in addition to the diameter paths;

FIGS. 30A–B show further details of a device like that in FIG. 30, the perforated stillwell being double-walled and containing between the walls, the transducers and the wiring, isolated from the fluid;

FIG.33 illustrates showing transducer positions and orientations in a multipath system.

DETAILED DESCRIPTION

Figure 1:
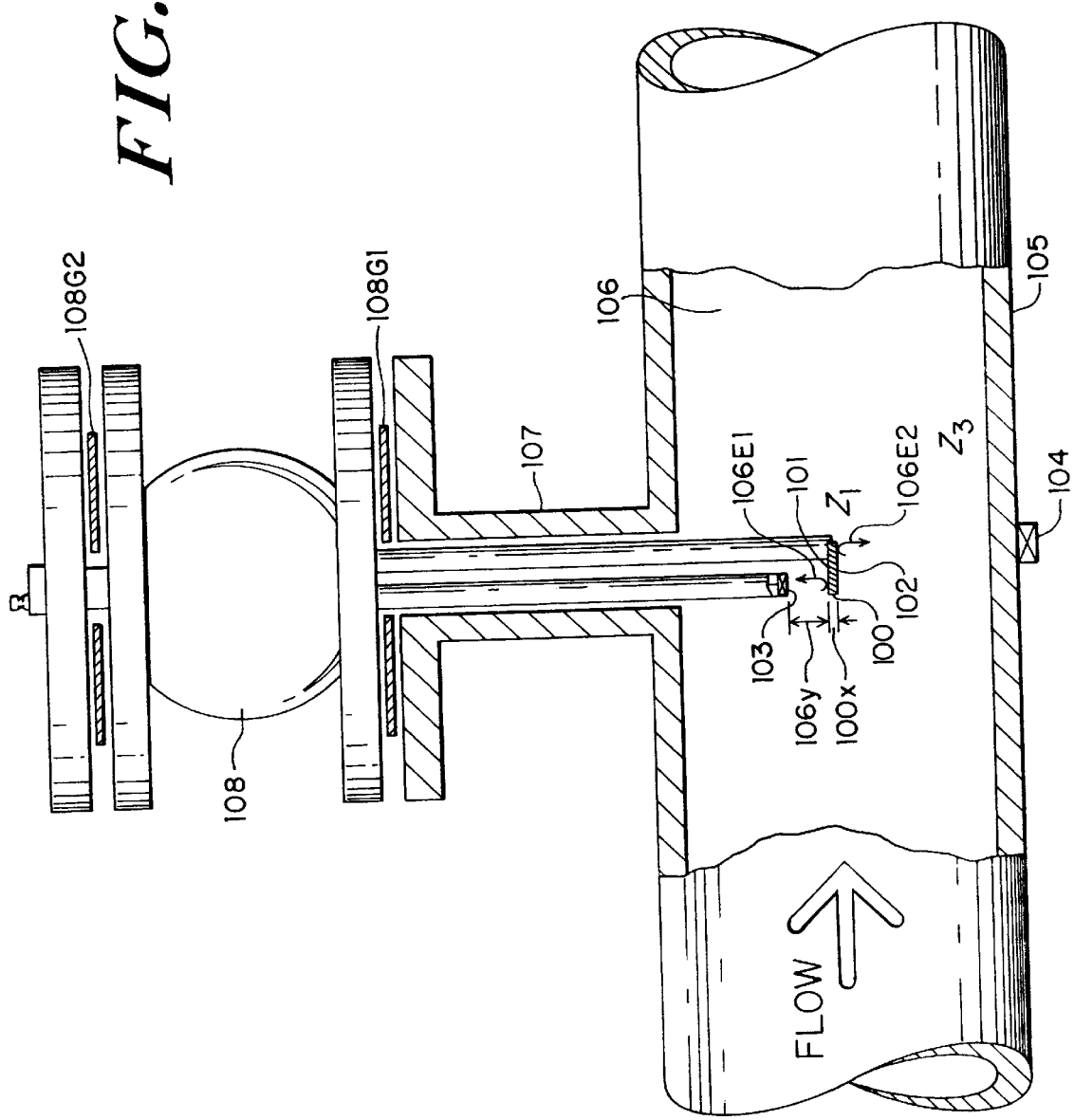
FIG. 1 is a one-port arrangement wherein the reflector, of characteristic impedance $Z_1$, is located in a pipe in the freestream and can be interrogated from a transducer that also lies in the freestream, or from an external transducer.

Broadly speaking, an ultrasonic measuring system according to this invention measures the acoustic impedance of a fluid and a sound speed or temperature, preferably in the immediate vicinity of where the impedance is measured, and from these measurements, determines the fluid density. As is well known, at normal incidence the sound pressure reflection coefficient, R, depends on the impedances on either side of the interface:

$$R=(Z_2-Z_1)/(Z_2+Z_1)=(r-1)/(r+1) \text{ where } r=Z_2/Z_1.$$

This terminology and these relationships are fairly standard and are found in most books on acoustics. R ranges from −1 to +1, passing through 0 when the two impedances match exactly. If there is a large mismatch the magnitude of R is nearly unity, and the sign, +or −, depends on whether the wave is approaching a higher or lower impedance, respectively. If R is to be a sensitive indicator of the impedance of the fluid, then the "input" impedance of the reflector, as seen by the approaching wave, should be comparable to the fluid's impedance. However, this does not mean the characteristic acoustic impedance of the reflector must be similar to that of the fluid. Impedance transformation will be shown to offer another way to achieve the comparable impedance, besides using low impedance materials. One adaptation of this idea is to coat a metal locally or over an extended region with a plastic or other low-impedance material, to achieve reflectivity quite different from that of the metal alone.

If the incident pressure has unit amplitude, then the amplitude of the echo reflected off a given reflector at normal incidence equals the reflection coefficient. Applicant has found it particularly useful in some instances to employ a wetted reflective surface that is totally reflective, $|R|=1$, for generating the reference echo. Totally reflective wetted reflectors can be flat if insonified by shear waves, or vee-shaped if insonified by longitudinal waves in a corner-reflector arrangement, provided that sound speeds in the vee block are high compared to $c_3$ in the fluid.

It may be convenient to introduce these ideas in greater detail by a brief derivation. For this derivation we shall use the notation: $Z_3$=fluid impedance, $Z_1$, $Z_2$=impedances of two solids; $r_1$=impedance ratio $Z_1/Z_3$, and $r_2$=impedance ratio $Z_2/Z_3$. If A and B are the amplitudes of echoes reflected at normal incidence off solids 1 and 2, we find $r_1=(1+A)/(1-A)$ and $r_2=(1+B)(1-B)$. The ratio of echo amplitudes is $A/B=(r_1-1)/(r_2-1)=C$, from which $Z_3=(Z_1-CZ_2)/(1-C)=[Z_1-(A/B)Z_2]/(1-A/B)$.

Thus we have the sought impedance $Z_3$ in terms of known solid impedances and a ratio of measured echo amplitudes. It follows that as long as one can determine the sound speed $c_3$ in the fluid, one can solve for fluid density. A special simplifying case occurs if the reflection coefficient at one of the solids, say solid 1, has unit magnitude. This would occur, according to theory, if the characteristic impedance $Z_1$ were zero or infinite. In accordance with this invention another solution is proposed, namely employing a metal corner reflector as a totally reflecting device, preferably in combination with a low-sound-speed corner reflector, e.g. made of plastic, to achieve in a compact arrangement, an enhanced sensitivity measure of density and flow velocity. Differential reflectivity of this type may be implemented with just one metal vee block corner reflector of which a portion is coated with plastic. The height of the metal's vee can be stepped to accommodate the thickness of the plastic coating and also taking into account that one may want the bare metal to stand up higher than its coated part, so that the echoes from the metal, which are stronger than those off the plastic coating, arrive earlier for accurate contrapropagation timing measurements for flow. In some embodiments, the use of a shear wave for obtaining the totally reflected reference signal is preferred.

Referring to reflectivity equations for normal incidence between two media of different impedances, and as explained in the contemporary references cited earlier (Van Deventer and Delsing, or Adamowski et al.) if one of the two impedances is known, by measuring R, one can determine the value of the other impedance. For example, suppose we assume for now, that the impedance of a solid reflector is known, and we are trying to determine the fluid impedance. Further, if the sound speed c is known, or can be computed or can be measured in the fluid, then the fluid density is readily computed, at least according to simple theory. However, further analysis readily shows that this kind of determination of fluid density requires very precise measurements of the amplitudes of echoes, in order for R to be determined with useful accuracy, including compensation for temperature effects.

Applicant recognized that by obtaining two values for R, one from each of two different wetted reflectors, a normalization can be executed, eliminating much of the potential drift and uncertainty in the usual reflection coefficient determination. Applicant subsequently recognized various ways of obtaining two reflections in combination with flow or other measurements; of obtaining the measurements at certain locations that yield advantages in flow accuracy while retaining a flushed surface for reliable R measurements; obtaining measurements with all transducers outside the pressure boundary; obtaining measurements using very small quantities of special (or polished) materials as reflective buttons or coatings; and found a way of increasing the transmitted signal strength while at the same time optimizing the sensitivity of the measurement of reflections. Each of these approaches enhances the utility of the reflection signals for measuring the desired parameter, although not all these features are used in every embodiment to be described below.

Referring now to FIG. 1, the reflector 100 has a characteristic acoustic impedance $Z_1$, a first reflecting surface 101 and a second reflecting surface 102. Reflector 100 is immersed in the freestream of fluid 106 conveyed in pipe 105 from left to right, as indicated by the fluid flow arrow weld bead on the pipe, at the pipe inlet. The fluid washes over the immersed reflector and transducer, keeping them clean by "stream-cleaning", i.e., in this instance by the natural flow of the stream. The transducer 103 is close to the reflector and a fixed distance above it, and so it is easy to obtain a sound speed c measurement in the fluid between the two. This is readily done by predetermining (measuring) distance 106y and, after fluid fills the pipe 105, the round trip transit time of echo 106E1 is measured. As long as the geometry or thickness 100x of reflector 100 prevents echoes within it from interfering with the sought reflection coefficient measurement from above, this simple arrangement can be used to determine fluid density. One could also determine the reflection coefficient from below, using external transducer 104, and timing echo 106E2. But now it is not as easy to determine c, because the path in the fluid is not known very accurately. There are, however, several solutions. One solution is to measure the time between reverberations within reflector 100, and use these to determine the temperature within the reflector. The reflector is thereby used as an ultrasonic thermometer sensor. If it is reasonable to take the reflector temperature as representative of fluid temperature, then this method may suffice. The fluid sound speed presumably is known as a function of temperature. If the temperature is measurable to within 1° C., then c is probably determinable to an accuracy of ⅓ to ¼ of a percent, for typical liquids. Assuming the goal is to compute density to 1% accuracy, a determination of c to these fractions of 1% appears adequate.

The combination of reflector 100 and immersed transducer 103 enter the pipe through a nozzle 107 by passing through a ball valve 108, details of which are well known in the process industry. If the depth of immersion were variable, one could determine the density profile. In summary, FIG. 1 has illustrated a one-port arrangement wherein the reflector, of characteristic impedance $Z_1$, is located in a pipe in the free stream and can be interrogated from a transducer that also lies in the free stream, or from an external transducer. We have to this point, illustrated some of the basic ideas, but not necessarily in the preferred configuration.

The idea of bouncing ultrasound off an immersed reflector is not new. In Liu and Lynnworth, U.S. Pat. No. 5,456,114, issued Oct. 10, 1995, FIG. 6C shows a pair of wetted transducers utilizing a reflector at one or more depths within a pipe, described briefly in column 11, lines 34–54 therein. The variable-depth reflectors were used for flow velocity measurement(s) averaged out to the reflector(s). The reflecting plates are there described as teflon-coated titanium to resist fouling and corrosion. Those reflectors, however, were not used to sense density, nor to provide reference echo amplitudes. No particular use of the ratio of velocities out to the two reflectors is suggested. In that patent the patentees point out that the reflecting plates could yield an echo more reliably than the far wall of the pipe, if that wall were pitted or corroded.

Figure 2:
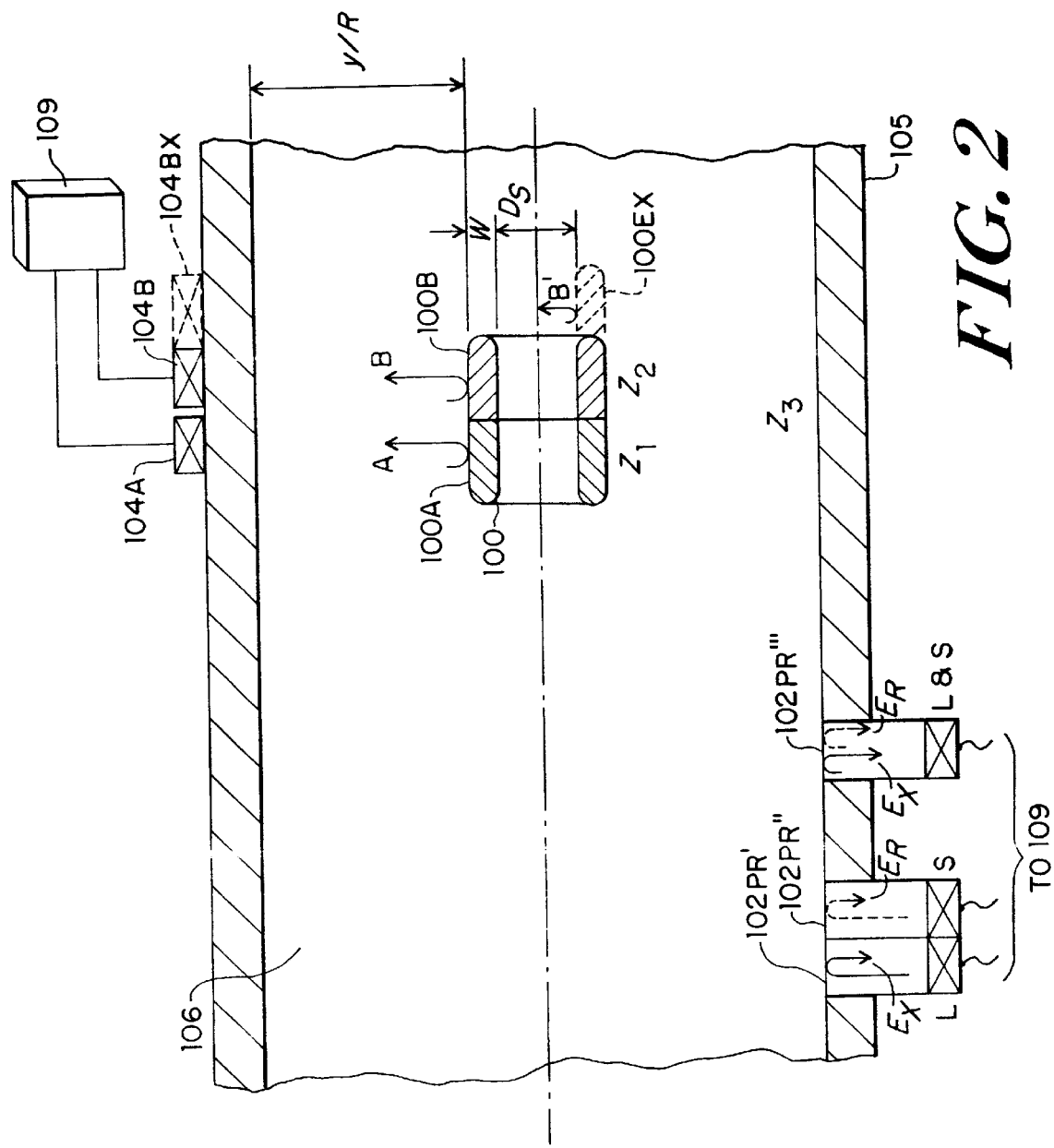
FIG. 2 is cross section showing a differential cylindrical tubular reflector having two different impedance segments, and at least one surface of the reflector is located at a distance in from the pipe wall denoted y/R.

In FIG. 2 there is shown in cross section a pipe 105 conveying fluid 106, and containing a differential cylindrical tubular reflector 100 having two different impedance segments 100A and 100B. Their respective impedances are $Z_1$ and $Z_2$. The upper surface of reflector 100 is located at a distance y/R in from the pipe wall. Reflector 100 is positioned by radial support means, not shown, or by other conventional mechanical means. The full significance of y/R will be discussed in connection with subsequent figures that include means for measuring flow velocity. External transducers 104A, 104B transmit radially inward, generating echoes A & B at reflector surfaces 100A, 100B. The magnitudes of A and B echo amplitudes are unequal, in general, because $Z_1/Z_3 \neq Z_2/Z_3$. The echoes are received and processed in console 109, which determines fluid impedance from (A/B−1) and, in this case, converts impedance to density using a c measured over the fluid path y/R. Basically the density computer 109 solves for density based on the relative echo strengths of echoes bounced off reflectors having two different and known impedances, the calculation including compensating for sound speed in the fluid. [The sound speed in the fluid might also be determined from the time difference between echoes obtained from the near surfaces, namely, echoes A &/or B, and echoes from the inner wall of reflector 100. In this case the fluid path would be well known and can be computed in terms of the reflector's inner diameter. This internal diameter path could be controlled during manufacture and determined more precisely than path y/R, in many instances.] For example, if the lower portion of reflector 100 were extended to the right to provide an extended reflecting portion 100EX, and if the center transducer 104B were similarly extended to have an edge 100BX over the reflector extension 100EX, then an additional echo B' would be obtained with a further delay corresponding to the round trip radial path difference 2(W+$D_S$). At the lower left in FIG. 2, two forms of shear-wave-reference reflectometer probes are installed through the pipe wall 105. One uses separately-interrogatable L and S (longitudinal and shear) piezoceramics, which could be X-cut and Y-cut quartz. The other uses just one piezoceramic which is capable of generating both L and S waves. Echoes are shown dashed for the shear wave reference echo $E_R$, and solid for the longitudinal wave echo $E_X$ that senses the unknown $Z_3$ and $\rho$ of the fluid 106 in the pipe. Lead wires from the transducers connect to the console 109. The echoes are time separated because S waves travel only about one half as fast as L waves in the solid probes 102PR', 102PR" or 102PR'''.

Figure 3:
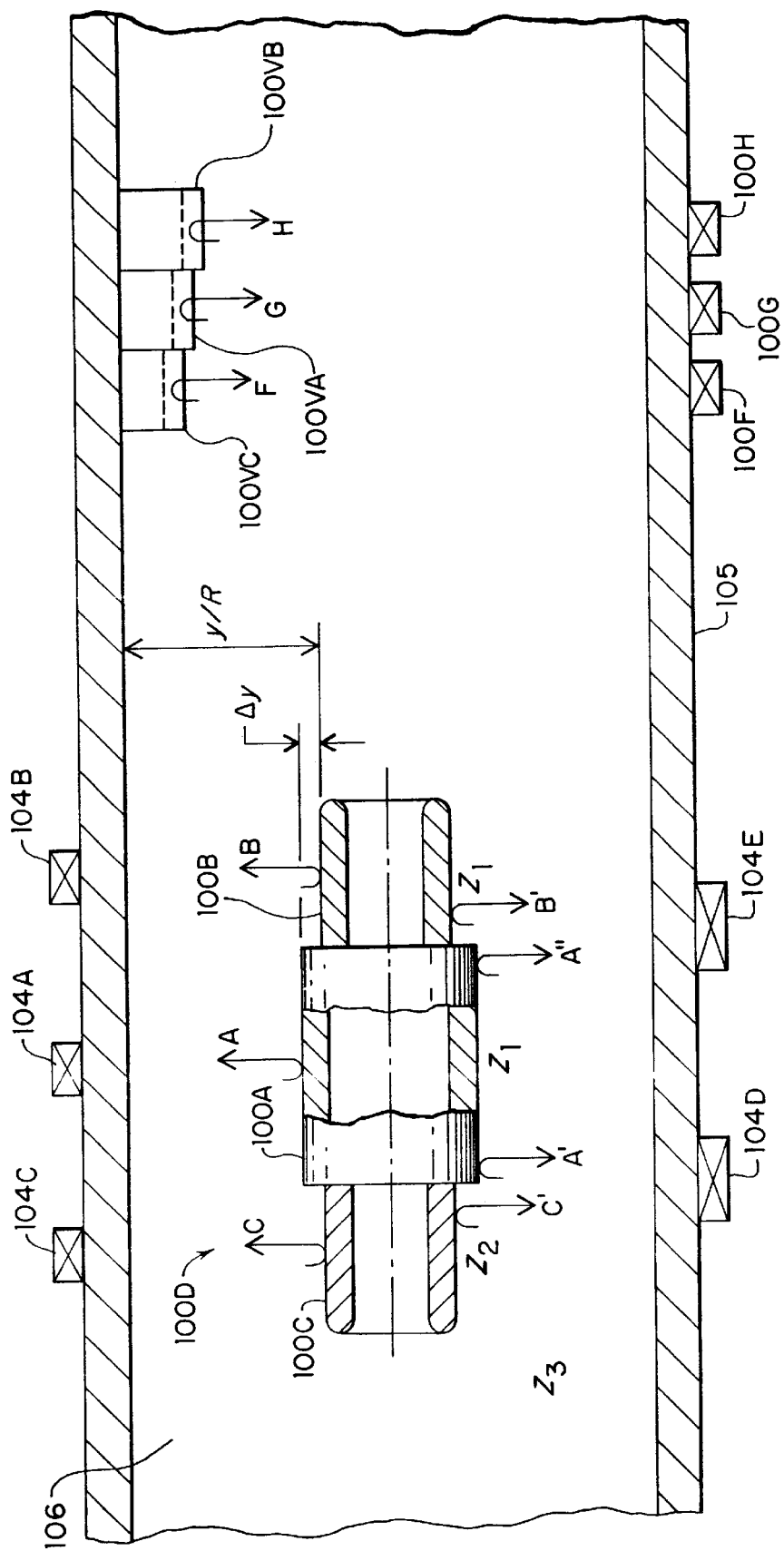
FIG. 3 is a drawing partly in cross section, showing a three-part cylindrical tubular reflector, two of the tubes having equal impedances, and two of the tubes having unequal outside diameters such that their outermost reflecting surfaces are differentially spaced by an amount denoted y.

In FIG. 3, which is a drawing partly in cross section, applicant shows a three-part cylindrical tubular reflector 100D immersed in flowing fluid 106. The center and right tube have equal impedances ($Z_1$) but unequal outside diameters such that their outermost reflecting surfaces 100A and 100B are differentially spaced by an amount denoted Δy. On the top part of the pipe 105, transducers 104A, 104B, 104C are individually shown approximately centered over one of the three sections, to generate the echoes denoted A, B and C. The differential path Δy is used to measure c immediately adjacent the reflector body. The outboard segments have different impedances but are located at the same distance in from the pipe wall, i.e., sections at the left and right yield echoes B and C, with magnitudes that are not influenced by paths in the fluid of different distances. The reflecting surfaces 100B and 100C are both y/R in from the wall of pipe 105. If fluid 106 is of uniform sound speed $c_3$, then the ratio of transit times to reflector 100A and reflector 100B will be in proportion to radial distances (y/R−Δy)/(y/R).

On the bottom side of pipe 105 two transducers are shown, 104D, 104E, each straddling reflecting portions at two different distances in from the wall. The echoes returning to these bottom transducers are denoted A, A", B' and C'. If Δy is 3 mm and the fluid is water near room temperature, then c≈1500 m/s and the echo pair A' and C' will be well separated in time by about t=6 mm/(1.5 mm/$\mu$s)=4 $\mu$s. "Well separated" assumes an ultrasonic frequency in the range 1 to 5 MHz, i.e., >1 MHz, as such frequencies can be pulsed with short durations of just one or a few cycles. In a well-constructed system, the amplitudes of echoes A' and A" would be essentially equal, apart from the effects of reflector curvature and size.

On the bottom right portion of pipe 105 we also show three external clamp-on transducers 100F, 100G, 100H. These transducers each interrogate one reflecting portion of a three-part reflector system, generating echoes denoted F, G, H, reflecting, respectively off vees within corner-reflecting sections 100VC, 100VA and 100 VB. The geometry and function of this three-part reflecting system will be more apparent after considering FIG. 3A.

The echoes A, B and C involve just one interaction with the reflecting cylinder of FIG. 3. To "double" the sensitivity to fluid density, applicant arranges for each echo to interact twice with the reflecting target. This is accomplished in FIG. 3A, using a group of vee-grooved corner reflectors 100VA, 100VB and 100 VC. Reflector 100VA, the central reference section, is made of a metal like aluminum, 316 SS or Ti. Outer reflectors 100VB and 100 VC could be made of plastic, or they could be plastic-coated segments of an underlying all-metal vee block. In a prototype the center piece was indeed made of Al and the side pieces were made of acrylic. As shown, the vees are at different elevations from the face opposite said vees, which face is referred to as the bottom face. That bottom face may be mounted in proximity to the inside wall of a pipe, as in FIG. 3, top right region, to orient the reflector such that the vees can be interrogated from the opposite wall, preferably using clamp-on external transducers. Analogous to the transducers straddling two differentially positioned reflecting cylindrical surfaces in FIG. 3, wide transducers like 104D, 104E may be employed to interrogate the vee assembly, yielding echo pairs as described previously. These echo pairs contain information on c as well as on the fluid impedance Z=$\rho$c, from which $\rho$ may be calculated. The vee surfaces are preferably orthogonal to one another, which means that the angle of incidence for the anticipated across-the-pipe interrogation is very nearly 45°. Since 45° is well above the critical angle for typical metals (Al, 316SS,Ti), total internal reflection occurs for rays in the fluid striking the vee of the metal (central) part. However, for the plastic parts, since their longitudinal sound speed is typically around 2000 m/s, and in shear mode can be as low as 500 m/s if polyethylene were selected, some of the incident energy enters the plastic vee region. This means the low-sound-speed vees provide an echo doubly attenuated (and phase shifted) because of the double interaction of these echoes with the fluid/low-c solid interface. In fact the sensitivity can be increased by a factor much more than two, because at 45° oblique incidence, transmission into the plastic is much greater than at normal incidence. This "effectively-reduced impedance," is analogous to the "transformed impedance" obtained by the quarterwave matcher, when the wave impedance (input impedance) presented by the $\rho$-sensing target closely matches the wave impedance in the fluid.

Figure 3A:
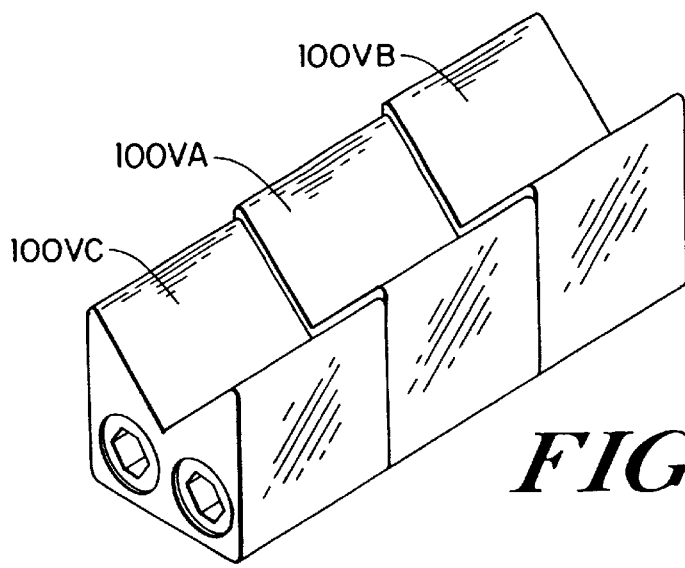
FIG. 3A is a drawing of an alternative three-part reflector system, comprised of vee-grooved corner reflectors, and otherwise sharing some of the differential-impedance, differential fluid path characteristics of the configuration of FIG. 3.

A prototype embodiment of the reflector of FIG. 3A was fabricated to fit within an envelope of one inch by one inch by three inches, with the end pieces bolted to the centerpiece using standard ¼-20 socket head SS cap screws. This could obviously be scaled down to 1×1×3 cm, and the three pieces could be bonded and/or bolted together.

Below, in connection with FIG. 29A applicant describes a compact assembly for folding the path in the fluid such that ten or more reflections occur. In various embodiments, applicant configures a system so that a large selectable number of these reflections occur at low-c solid interfaces (using, for example, plastic button inserts at such points). This increases sensitivity to changes in fluid density when the fluid is a liquid, and in some circumstances might even make it practical to sense changes in gas density, if gas pressure were high enough, provided a sufficient number, e.g., ten to twenty reflections were utilized.

Figure 3B:
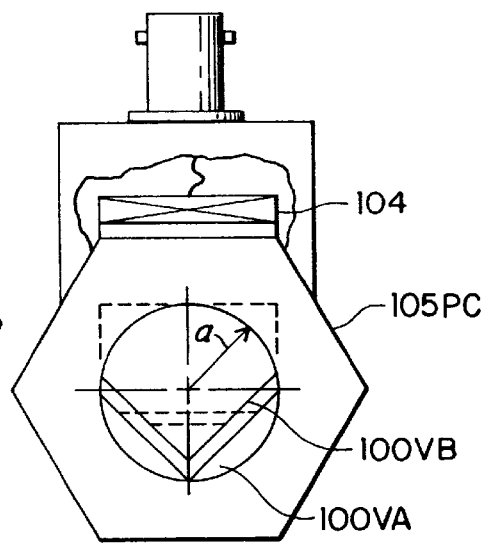
FIG. 3B is an end view showing interrogation of the full cross section of flowing fluid, and including vee blocks at two different heights.

The stepped vee block of FIG. 3A may be introduced into a pipe coupling 104PC having an end view shown in FIG. 3B. Transducer 104 is intended to interrogate the entire cross section of the flowing fluid, according to a known area-averaging method, e.g., that of U.S. Pat. No. 3,906,791 issued Sep. 23, 1975 to Lynnworth. The measuring passageway, however, is not necessarily square or rectilinear in the present design, and in that respect differs from its predecessors. The dashed paths across the vees look like they are in a plane perpendicular to the axis of the pipe coupling, but below applicant describes a more preferred orientation for these paths.

Figure 3C:
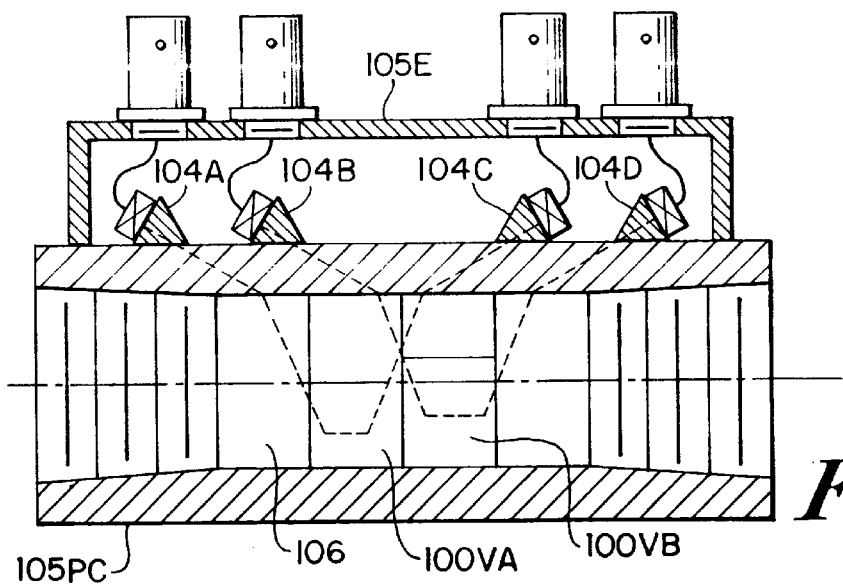
FIG. 3C is a side view corresponding to FIG. 3B, in which transducers are external to a pressure boundary.

Referring now to FIG. 3C, the pipe coupling 105PC, which we can think of as made of plastic, has four "clamp-on" transducers 104A . . . D within a cavity defined by enclosure 105E. Fluid 106, particularly a liquid, flows through the pipe coupling. The coupling also contains two vee blocks 100VA and 100VB, like the ones in FIG. 3A. The dashed paths each strike a first face of a vee, reflect axially downstream (or upstream, depending on interrogation direction), and then proceed off the second face of the vee to make their way back up to a receiving transducer. One of the paths enjoys total internal reflection within the fluid. We shall take this to be the right-hand path that bounces twice off the vee of taller and typically metal vee block 100VB. The left-hand path bounces twice off the vee of the shorter (and presumably plastic) vee block 100VA, arriving later, in fact distinguishably later, and also much attenuated by its double interaction with the plastic vee. In a laboratory experiment the plastic (acrylic) vee attenuated the waterborne 2 MHz test signal by some 30 dB, as compared to a totally internally reflected vee-bounced echo off an aluminum vee block. This great difference may be compared to the small difference in attenuations, only 3 dB between the aluminum and plastic echoes, which occurs at normal incidence. This behavior may thus be seen to quantify the statement made above concerning the "effectively-reduced impedance." (In another test at normal incidence, mentioned here for reference, with the flat reflectors made of carbon steel and Teflon, in water, the echo at a frequency of 5 MHz from steel was about five times stronger than that from Teflon.) In FIG. 3C the four transducer-wedge assemblies are shown separate, for ease of explanation. However, only two are needed, if they are made large enough. Each of the transducer assemblies is connected by a short wire to its respective BNC electrical connector, the connectors being threaded into the top of cavity enclosure 105E. Additional vee blocks like vee block 106 may be added upstream and/or downstream to condition the flow, to lengthen the reflective region along the axial direction, or to act as a mechanical stop for the central pair of vee blocks. The blocks may be pressed in, glued in, pinned in place or secured by other known means. If the pipe coupling 105PC and blocks were to be mostly metal the desired shape could be finished by EDM (electric discharge machining) of a roughed-out metal blank, followed by plastic coating of the "plastic" block 100VA.

Figure 3D:
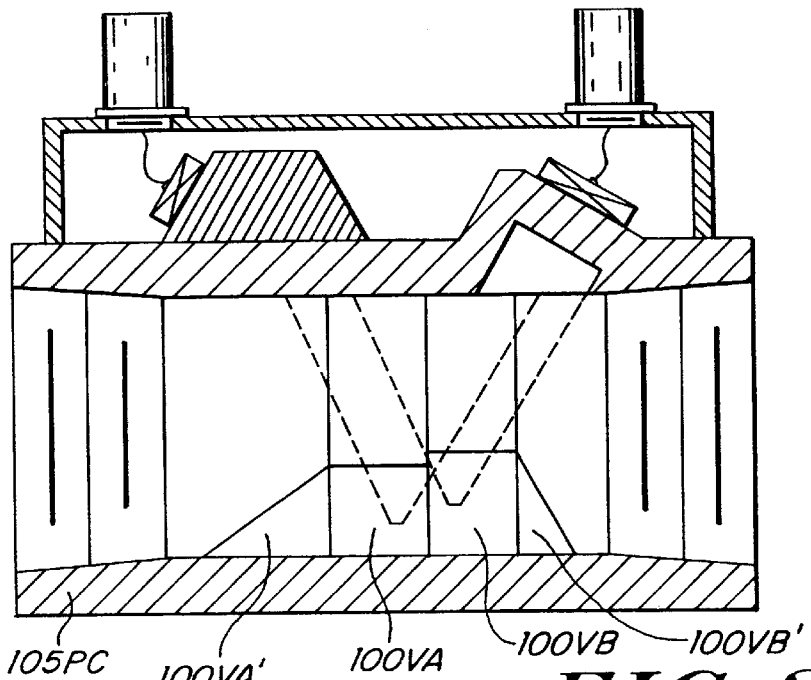
FIG. 3D is like FIG. 3C except a wetted version of the transducer is shown explicitly.

Larger transducers are represented in FIG. 3D, one being clamp-on, one operating through a cavity to avoid refraction. Respective ramps 100VA' and 100VB' are positioned next to the taller and shorter vee blocks 100VB and 100VA, to control fluid flow into the channel formed by the vees and the sides and upper wall of the pipe coupling 105PC. While the diagram shows two different types of transducers communicating with one another, in practice both would typically be of the same type.

Figure 3E:
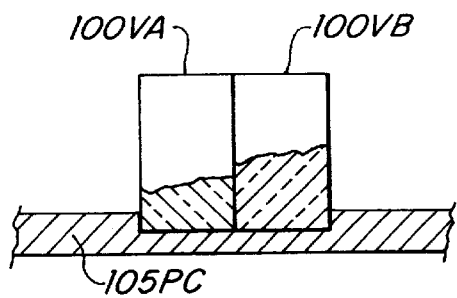
FIG. 3E shows the vee blocks tilted to encourage cleaning action by the flowing stream.

FIG. 3E shows another advantageous construction detail. A section of the wall of a pipe coupling 105PC is shown, including the two vee blocks 100VA, 100VB, but now slightly inclined, so as to promote cleaning action of the vee surfaces for fluid entering at the left. Other means of directing fluid flow in the vicinity of a density-sensing probe are found in Milton H. November, U.S. Pat. No. 3,956,922 issued May 18, 1976.

Figure 3F:
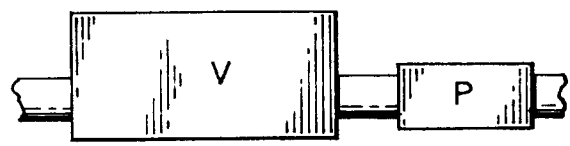
FIG. 3F shows the density section of a mass flowmeter in series with a flow velocity section, where the internal details may be understood from other figures to allow the possibility of the first section to be appropriate for very low flow velocities and the second (density) section to further allow for measurement of high velocities that might be beyond the range of the first section.
Figure 29:
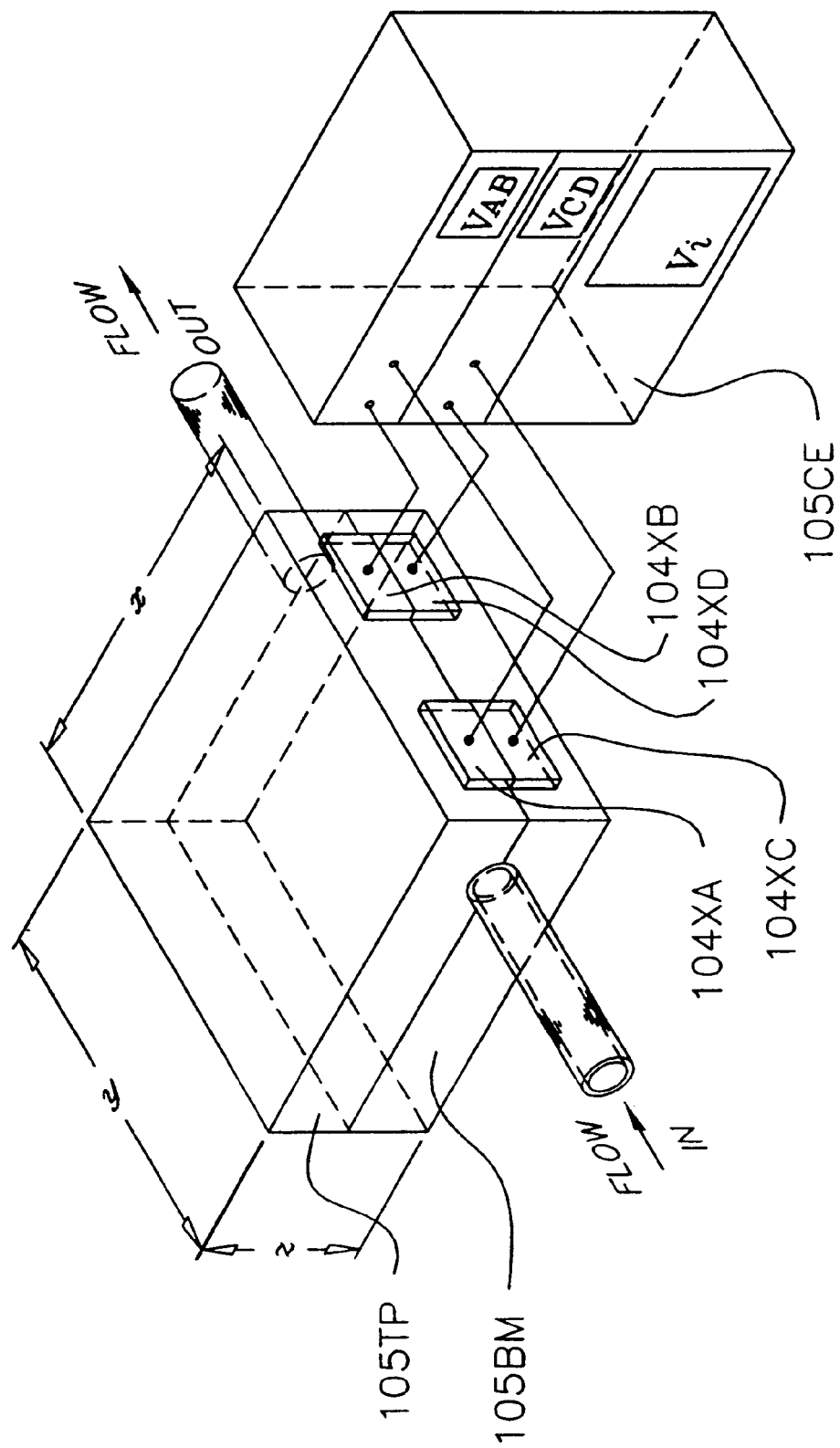
FIG. 29 shows a compact flow assembly that includes a folded path configured to provide more than ten oblique interactions at a fluid/solid interface, and a fluid path length well over ten times the diameter of the passageway, and further including split crystals for simultaneous and/or redundant measurements of density and flow velocity, to obtain an accurate measure of mass flow rate even at low flow rates.
Figure 29A:
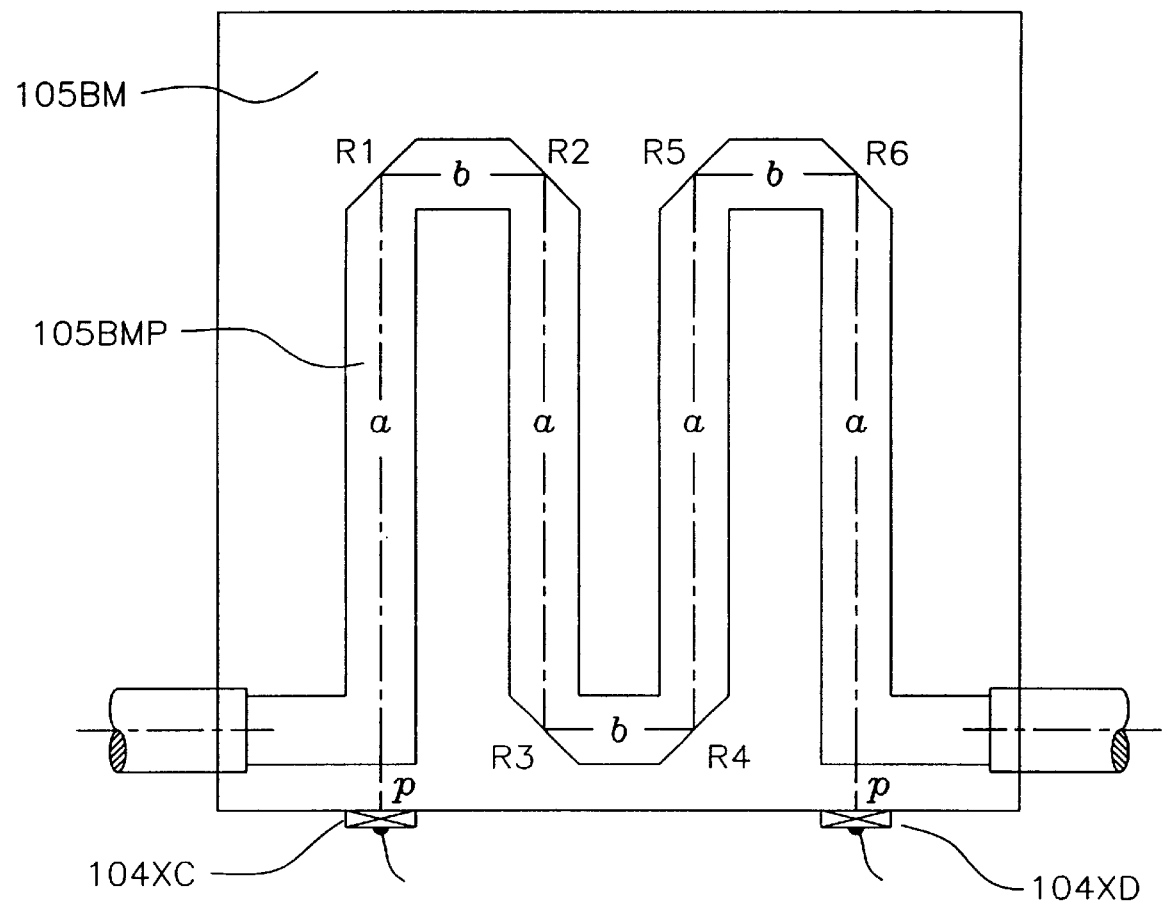
FIG. 29A shows one portion of an assembly similar to FIG. 29, illustrating a folded-path passageway, six oblique reflectors, and an interrogation path over four times greater than the distance between transducers.
Figure 29B:
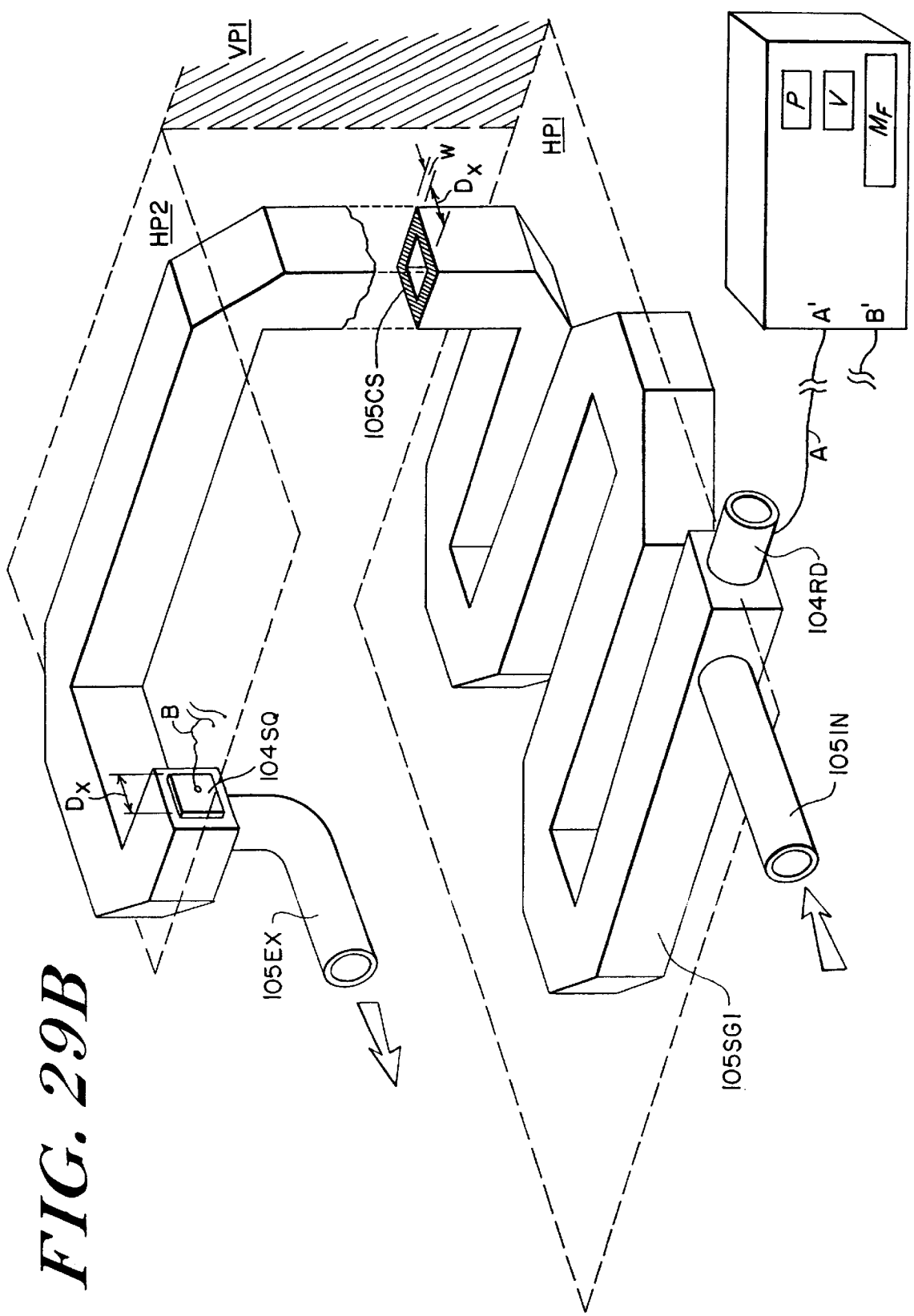
FIG. 29B is another version embodying some of the principles of FIGS. 29 and 29A, wherein the flowcell is comprised of square or rectilinear tubing segments lying in three different planes, the segments conveying the fluid and guiding the interrogating wave such that many internal reflections are utilized, and the total flow-sensing path is much longer than the edge dimension of a cube (or a rectangular parallelopiped) that envelopes the flow-sensing region.

FIG. 3F schematically represents the combination of a density sensing configuration (labeled ρ, on the right) which for example could be the one depicted in FIG. 3C, together with a V-sensing flowcell which might be the folded path flowcell of FIGS. 29A or 29B. The folded path flowcell can measure very small flows, while that in FIG. 3C is more appropriate for high flows up to 10 m/s or more. Either of the two sections shown in FIG. 3F may sense density too; it is implied here, however, that the section labeled ρ would provide the measure of density.

Figure 3G:
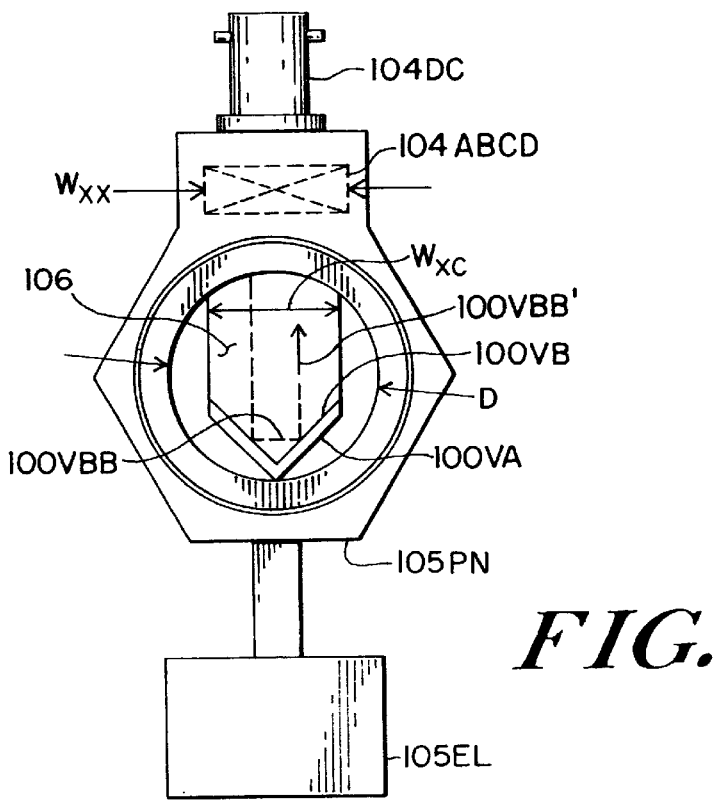
FIG. 3G is an end projection of a short compact assembly responsive to flow and density, utilizing a pair of vee blocks, one plastic, one metal, the metal one being slightly taller such that its echoes arrive distinguishably earlier than the echoes from the plastic vee block.

FIG. 3G is a an end projection of a short compact assembly responsive to flow and density, utilizing a pair of vee blocks, one plastic, one metal, the metal one being slightly taller such that its echoes arrive distinguishably earlier than the echoes from the plastic vee block. In the construction of FIG. 3G, a hex pipe nipple 105PN, which may be of nominal size one inch (~25 mm) and of overall length ~100 mm is modified to contain two vee blocks. The shorter one, vee block 100VA, is made of plastic. The taller one, vee block 100VB is made of metal, such as A1, Ti or SS. In the end view one of the rays appears as a square letter U whose bottom segment, denoted 100VBB, echoes up as ray 100VBB'. This is but one of many rays emanating from four transducers collectively represented by the piezoceramic 104ABCD. The fluid 106 being measured is confined in the vee block vicinity to a channel of width $W_{XC}$ such that interrogation by ultrasound emanating from transducers of width $W_{XX} \times W_{XC}$ is area averaged with respect to flow velocity by known means. The electrical connector to each transducer element is represented by BNC connector 104DC. However, the electrical lead wires may pass by known means directly to an integral electronics module 105EL.

Figure 3H:
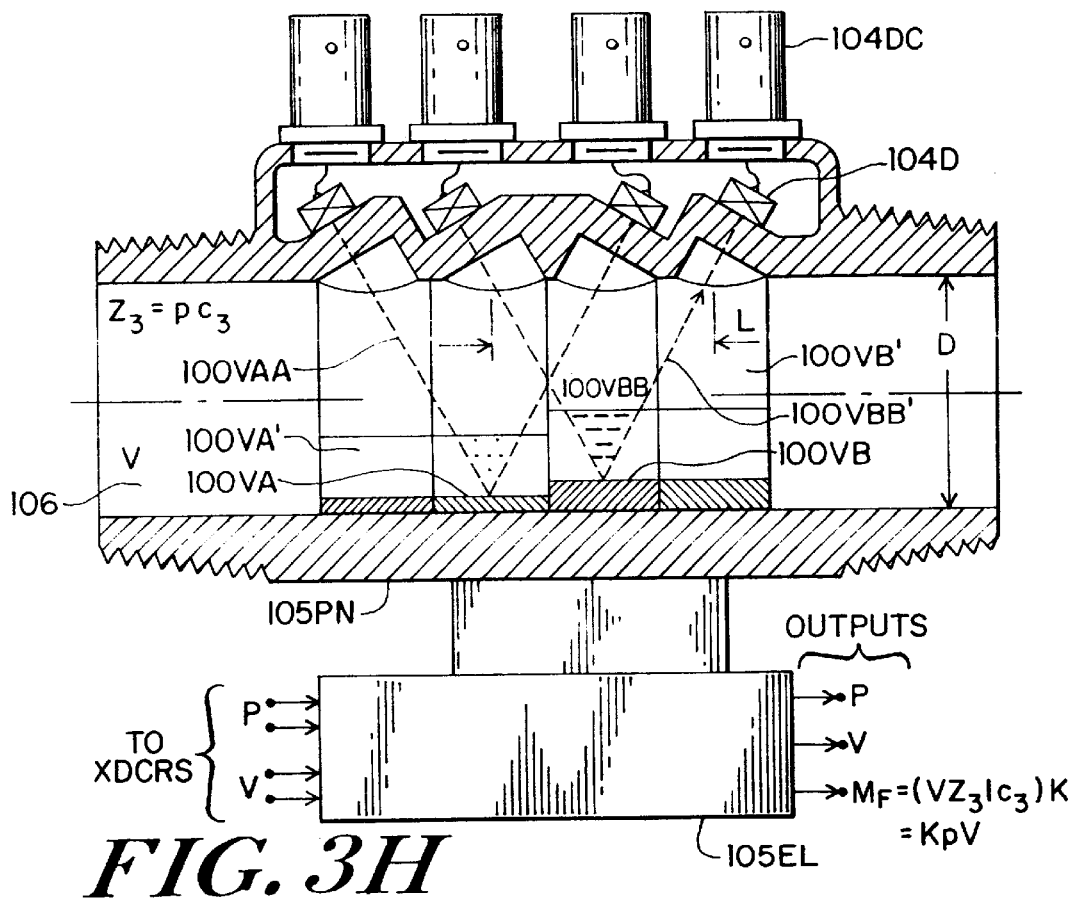
FIG. 3H is a side view of the device of FIG. 3G, clarifying the positions and heights of the two vee blocks, and showing all transducers to be of like construction, and further showing how the paths interrogate the fluid in an axial direction utilizing the reflective properties of a corner reflector illuminated (insonified) obliquely with respect to a plane perpendicular to the flow axis.

FIG. 3H is a side view of the device of FIG. 3G, clarifying the positions, heights and functions of the two vee blocks 100VA, 100VB. Duplicate vee blocks 100VA', 100VB' are shown outboard and adjacent the inboard pair. The outboard pair smooth the flow measured by the inboard pair. Fluid 106, characterized by acoustic impedance Z3 and flow velocity V, is interrogated in two different ways. Path 100VAA obliquely interacts with the vee and is delayed relative to path 100VBB' because its vee block is lower. The rays traversing paths like path 100VAA are efficiently transmitted into the plastic vee block when the sound speed in the fluid is comparable to the shear wave velocity in the plastic, and this leads to a highly attenuated echo the amplitude of which is accordingly quite sensitive to fluid impedance or density. In one laboratory experiment using an acrylic vee block, a ~10 dB difference in echo amplitude was observed, for the two different fluids, water and alcohol. As is well known, the density of alcohol is about 80% that of water. This suggests that if echo amplitudes can be measured to ±0.1 dB then the 0.2 g/cm³ difference can be measured to the order of 2 mg/cm³. Notice too that the interrogating ray or path is inclined axially, the axial projection being L. The actual path includes a short diagonal element such as diagonal element 100VBB. The net result for rays interacting with the metal vee block 100VB, which is taller, is that they arrive distinguishably earlier, so that even if the pair of receiving transducers of the set of four transducers illustrated, were connected electrically in parallel, the electronics module 105EL could still sort out which echoes were from the metal vee block and which ones were from the plastic vee block. (The amplitude difference would also make this apparent, and would eliminate the need for different height, as sound speed $c_3$ in the fluid can be determined in this geometry without recourse to differential heights.) All four transducers are shown as identical (nonrefracting) designs, not mixed as in FIG. 3D. For clarification, we number one of the piezo-ceramic elements 104D wired to its electrical BNC connector 104DC. Two of the BNCs are associated with measuring V, and the other two, with density, and they are so labeled. The electronics module 105EL takes signals from these transducers and using known microprocessor means, converts the amplitudes and transit times to the desired outputs as indicated; the outputs have dimensions of density, flow velocity, or their product, corrected for profile and duct area A. Again, there is little need for profile correction if the area-averaging method is used, as indicated in the end view, FIG. 3G. Again, in FIG. 3H, the illustrated paths interrogate the fluid in an axial direction utilizing the reflective properties of a corner reflector illuminated (insonified) obliquely with respect to a plane perpendicular to the flow axis. Interrogation is bidirectional for vee block 100VB; it is unidirectional or optionally bidirectional for vee block 100VA.

Figure 3I:
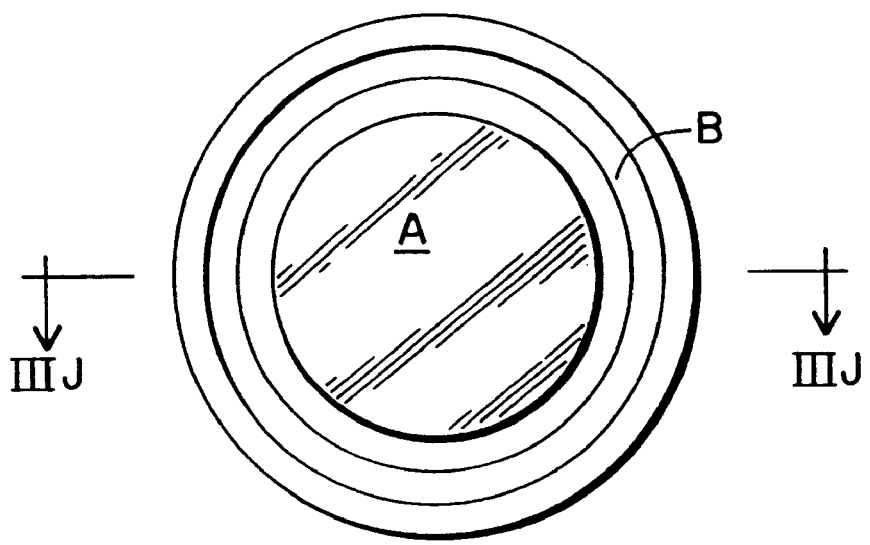
FIGS. 3I and 3J are views of a grooved single material reflector for density sensing.
Figure 3J:
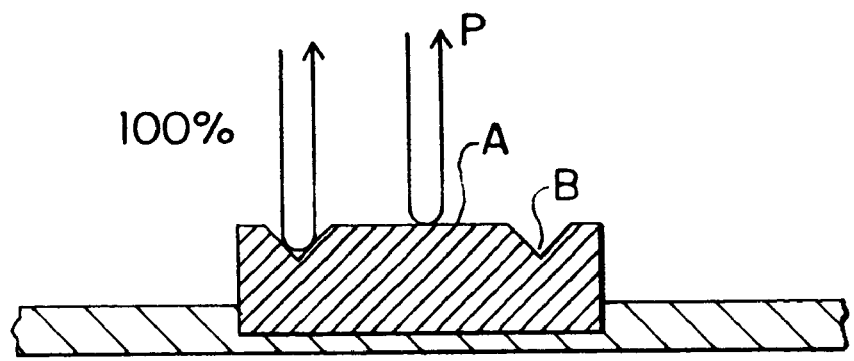

One particularly effective reflector for the practice of the invention is shown in a top plan view in FIG. 3I, and in vertical cross-section in FIG. 3J. As illustrated, this reflector has the shape of a generally solid cylinder, with a V-groove machined about its perimeter. The V-groove may have 45 degree walls so that the signal striking the wall is reflected back along its path of incidence, i.e. may act as a corner reflector. The central portion of the cylinder is faced flat, and may for example have a diameter of 0.707D so that it occupies one-half the cross-sectional area of the reflector face. In this embodiment, the body may be formed of a common engineering metal such as stainless steel, aluminum or titanium, and as discussed above, since the signal strikes the V-groove above its critical angle, it will experience total reflection from the grooved region. The reflection of the portion of the signal incident upon the flat central face, however, will depend on fluid density. The two reflections will be separated in time owing to the slight path difference, and can be received by a single transducer to be processed to yield a difference or ratio.

Figure 4:
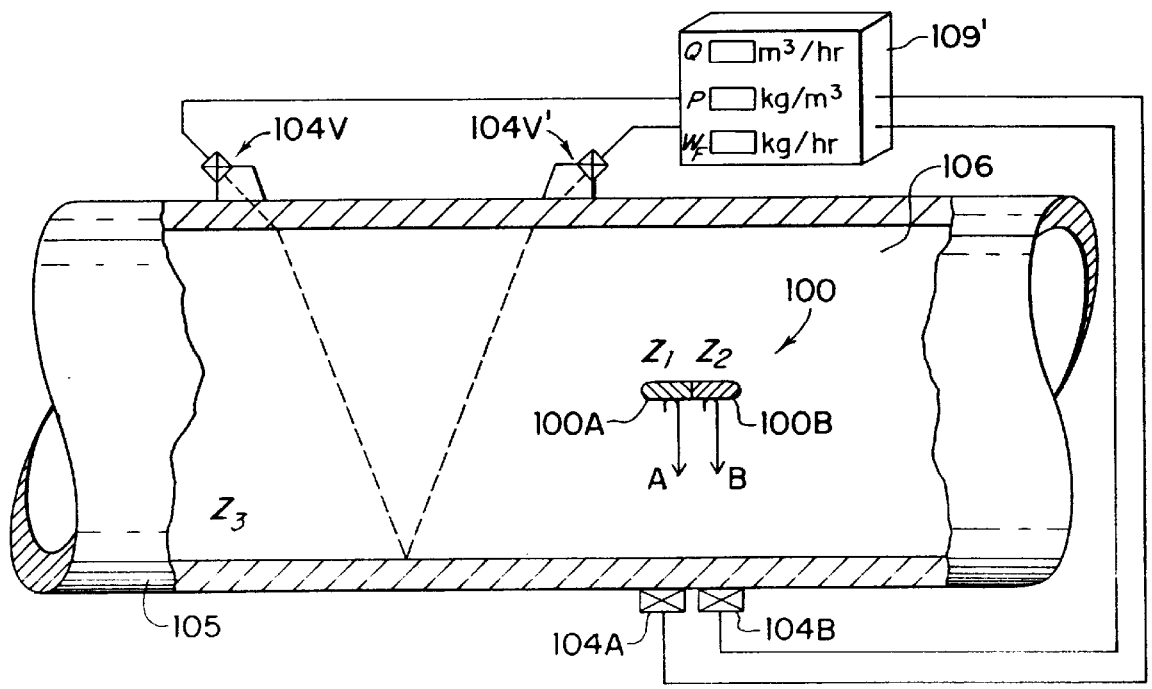
FIG. 4 is drawing, partly in cross section, of a pipe containing a flowing fluid of characteristic impedance $Z_3$ and, in the freestream, a two-part reflector, each part constructed of a material having a different acoustic impedance, thereby generating at a single surface parallel or concentric with the conduit interior, in response to normal interrogation from a first pair of external transducers, two different echoes A & B, with the reflector displaced from the region where flow is measured by a conventional known ultrasonic method along an oblique vee path by a second pair of external (clamp-on) transducers that are independent of those used to obtain echoes A & B, but where all four transducers are connected to one electronic console that performs excitation, receiving, timing, analysis, computation of volumetric flow rate, density and mass flow rate, and display functions, the display functions being represented on said console by the rectangular areas labeled Q, ρ and $M_F$ and having units of $m^3$/hr, kg/$m^3$ and kg/hr, respectively.

FIG. 4, drawn partly in cross section, shows pipe 105 containing a flowing fluid 106 of characteristic impedance $Z_3$. In the freestream, there is immersed a two-part reflector 100. Each part is constructed of a material having a different acoustic impedance, thereby generating at a single surface, in response to normal interrogation from a first pair of external transducers 104A, 104B, two different echoes, one echo denoted A from surface 100A, and echo B from surface 100B, similar to FIG. 2. The reflector is displaced axially from the region where flow is measured by a conventional known ultrasonic method along an oblique vee path by a second pair of external (clamp-on) transducers 104V, 104V' that are independent of transducers 104A, 104B used to obtain echoes having amplitudes A & B, but where all four transducers are connected to one electronic console 109' that performs excitation, receiving, timing, analysis and display functions. The display functions are represented on multi-parameter console 109' by the rectangular areas for displaying volumetric flow rate, density and mass flow rate, labeled Q, ρ and $M_F$ and having units of $m^3$/hr, $kg/m^3$ and kg/hr, respectively. The two-part reflector 100 that generates echoes A & B may be oriented across the pipe, like a wing, passing through the pipe wall and may be welded, epoxied or otherwise attached and sealed thereto by known means.

Figure 5:
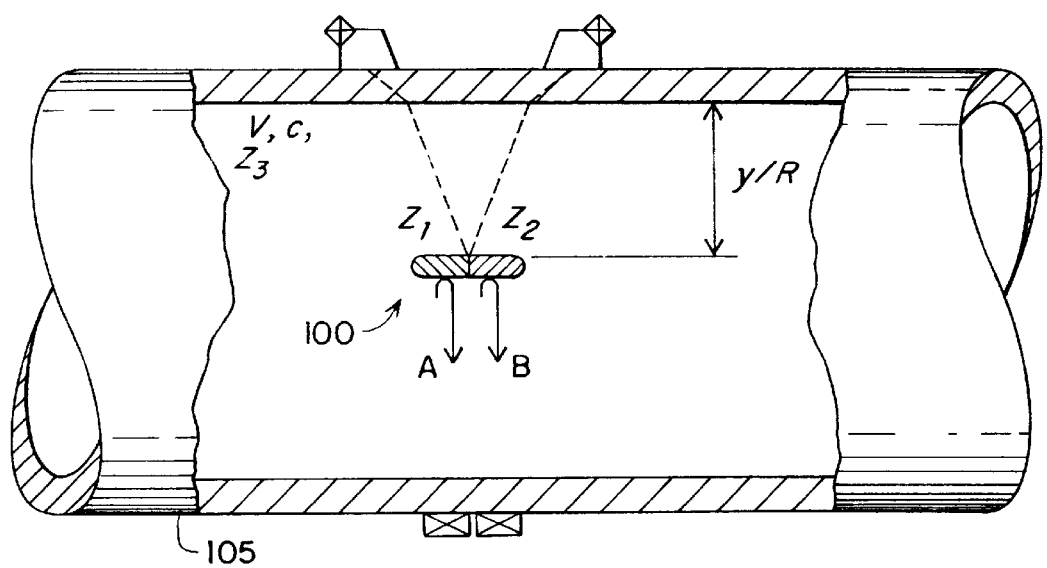
FIG. 5 is a drawing of a pipe, partly in cross section, showing a two-part reflector having two surfaces, one of which surfaces is located at a distance in from the pipe wall denoted y/R, and used for a vee-path measurement of flow velocity between the pipe wall and that reflector surface, while the other surface of the reflector is used to generate two different echoes A & B, having amplitudes denoted A & B, responsive to fluid density, all transducers being external and being understood to being connected electrically to a console as in FIG. 4.

FIG. 5 is a drawing similar to FIG. 4, including the pipe 105, partly in cross section, and showing a two-part reflector 100 having two surfaces. One of its surfaces is located at a distance in from the pipe wall denoted y/R, and is used for a vee-path measurement of flow velocity between the pipe wall and that reflector surface, while the other surface of the reflector is used to generate two different echoes A & B, responsive to fluid density, all transducers being external and being understood to be connected electrically to a console as in FIG. 4. In contrast to the construction of FIG. 4, the reflector 100 is now used for two purposes: first, to yield density-responsive echoes A & B from reflector regions of two different impedances, $Z_1$ and $Z_2$ and second, to yield a vee path for flow measurement over a particular distance y/R from the wall to a reflecting surface. The components in this figure, along with the appropriate console or processing module (not shown), yield three parameters of the fluid: V, c, $Z_3$, and from these determines fluid density and mass flow rate. If y/R=1 the V would have to be multiplied by a meter factor approximated by K=0.750 for laminar flow and K=1/[1.019–0.011 log Re] for turbulent developed flow.

Figure 6:
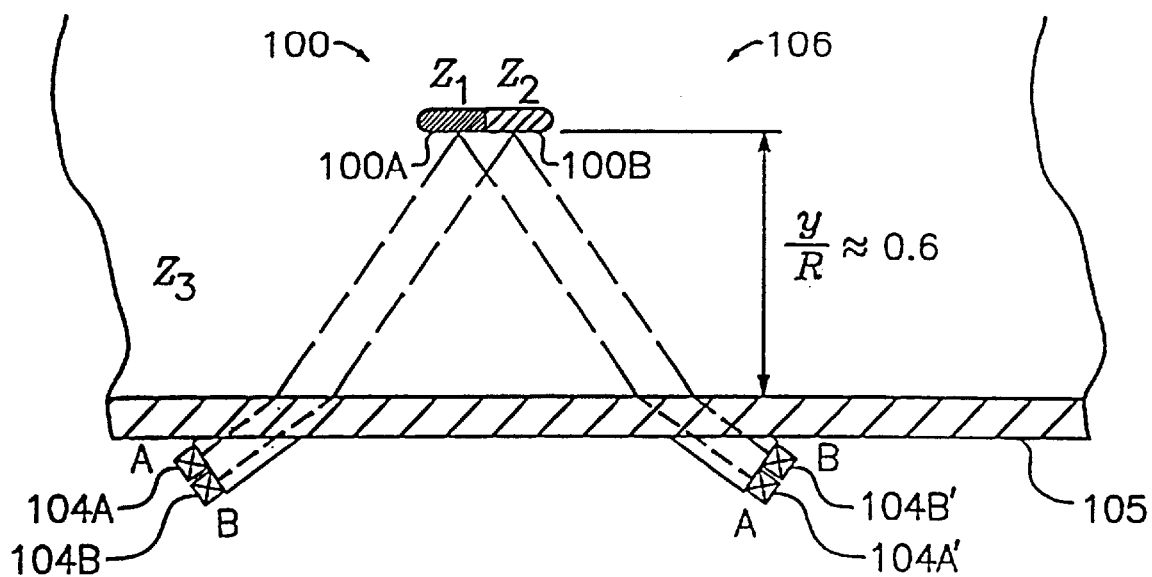
FIG. 6 is a cutaway view of a pipe, similar to FIG. 5 except the same surface of the reflector participates in the flow and reflection coefficient or density measurement, and all transducers are on the same side of the pipe, and the location of the reflector is shown specifically at y/R≈0.6, that location being preferred for obtaining a value for flow that very closely matches the area-averaged value $V_{AVG}$ when the profile is in accordance with a power law or similar distribution.

FIG. 6 is a cutaway view of a pipe 105, similar to FIG. 5 except the same surface of the reflector 100, and specifically its regions 100A, 100B participate in the flow and reflection coefficient or density measurement. All transducers 104A, 104B, 104A', 104B' are on the same side of the pipe. The location of the reflector's bottom surface is specified to be distance y/R=0.58–0.6 from the nearest pipe wall. That location is preferred for obtaining a value for flow of fluid 106 that very closely matches the area-averaged value $V_{AVG}$ when the profile is either laminar, or, if turbulent, is fully developed and in accordance with the known power law or similar distribution. This figure also introduces the determination of R at oblique incidence. The dashed paths imply that the reflection from reflector region 100A is accomplished using transducers 104A, 104A', while that from region 104B uses transducers 104B, 104B'. The console, not shown, includes the necessary switching circuitry, similar to that found in multipath ultrasonic flowmeters that switch between paths and between upstream and downstream directions unless those directions utilize simultaneous transmissions, as could also be used here. However, path separations would be easier if transmissions were alternated between the "A" and "B" paths.

Figure 7:
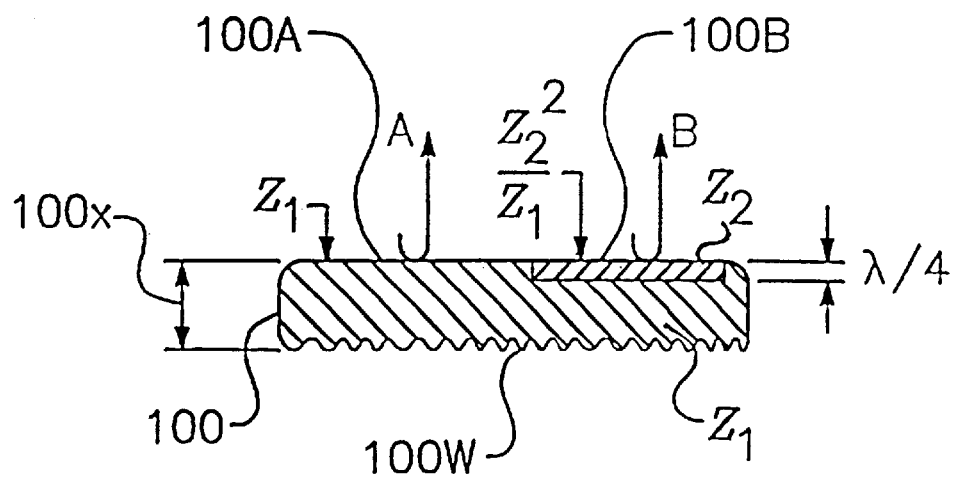
FIG. 7 is a detailed view of a differential reflector where one part of the reflector consists of a small quarter wave insert that transforms the backing impedance, thereby creating two different input impedances $Z_1$ & $Z_2^2/Z_1$ as labeled alongside the two corner arrows, and in turn generating two different echoes A & B, having respective amplitudes A & B, when suitably interrogated, as shown in FIG. 7A.

FIG. 7 is a detailed view of a differential reflector, mostly made of a material having impedance $Z_1$ but where one part of the reflector includes a small quarterwave insert 100B of characteristic impedance $Z_2$. The insert transforms the backing impedance, thereby creating two different input impedances $Z_1$ & $Z_2^2/Z_1$ as labeled alongside the two corner arrows. The reflecting surfaces, when suitably interrogated, generate two different echoes A & B, having respective amplitudes A & B. To prevent corruption of echoes A&B by reverberations within reflector 100, the reflector thickness 100x is made at least a half-wavelength thick and its back wall surface 100W is roughened by corrugations or other anechoic pattern.

Figure 7A:
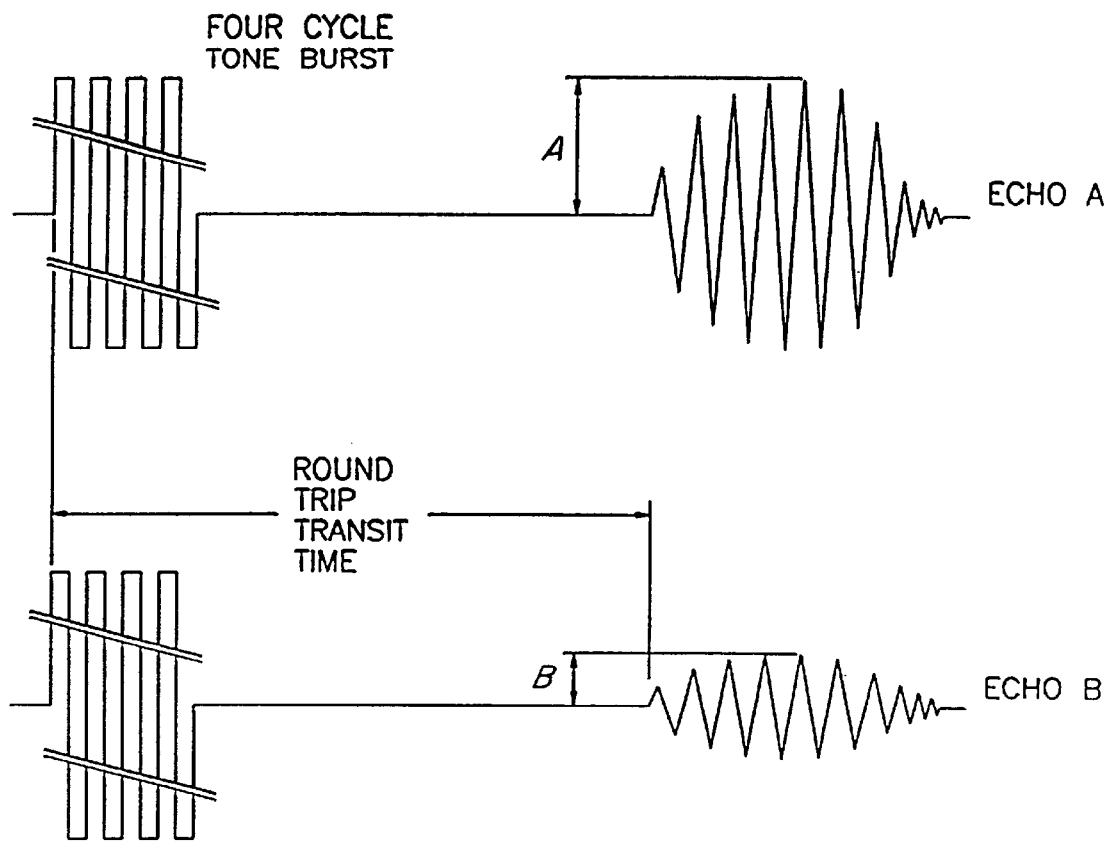

FIG. 7A depicts the shape and amplitude of echoes A&B as would be obtained with the differential reflector of FIG. 7. A four-cycle tone burst of the same amplitude is applied for each echo, but the echo B is much smaller because it echoes off a surface transformed to lie closer in impedance to that of the fluid in which the reflector of FIG. 7 was immersed. Both echoes arrive at the same time, in this example.

Figure 8:
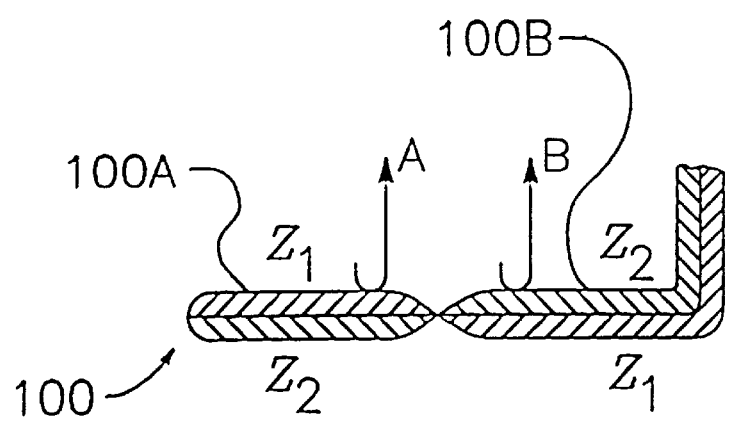
FIG. 8 is a cross sectional view of a bimetallic strip that can be thought of as a portion of a Möbius strip, and which, when installed like a sting into the flow stream, provides two different impedances and when suitably interrogated, two different echoes.

FIG. 8 is a cross sectional view of a bimetallic strip reflector 100 having portions 100A and 100B, each with respective impedances $Z_1$ and $Z_2$ that can be thought of as a portion of a Mobius strip, and which, when installed like a sting into the flow stream, would provide echo surfaces of two different impedances and when suitably interrogated, two different echoes A&B. Here the impedance transformation is obtained by twisting the reflector 180 about an axis typically lying parallel to the flowstream or pipe axis.

Figure 9:
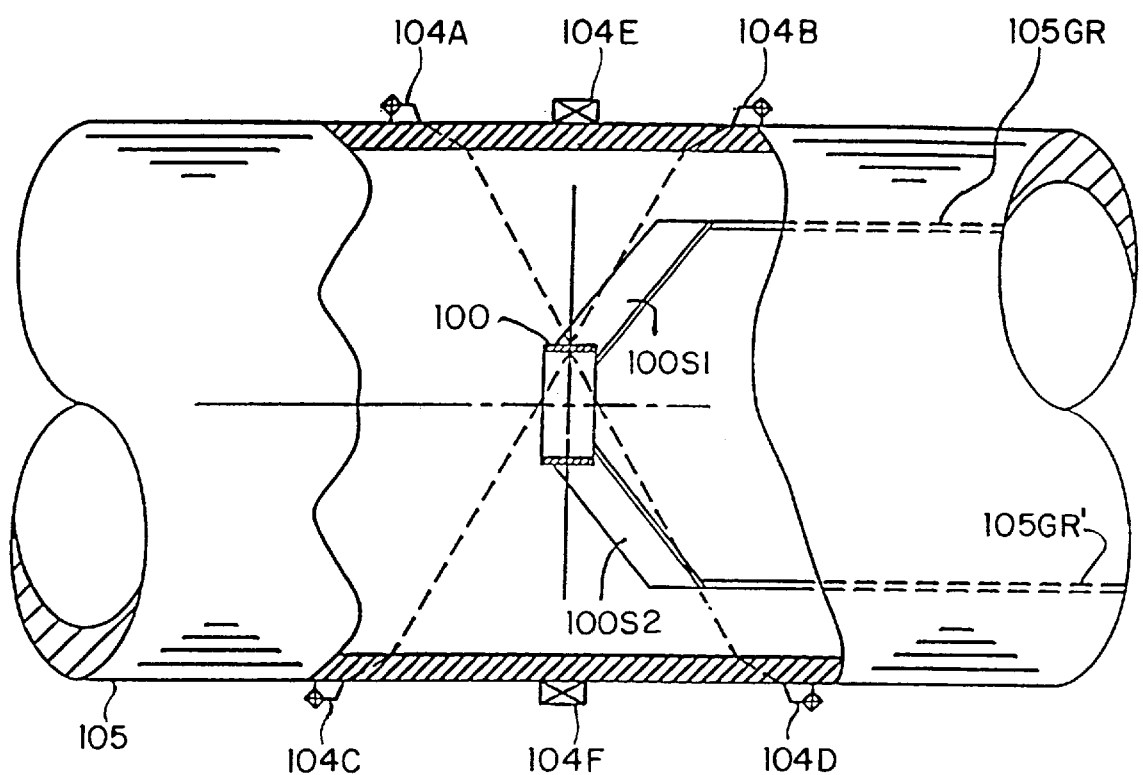
FIG. 9 is a side view, partly in cross section, of a relatively short cylindrical tube reflector, of length less than its diameter, centralized within a pipe, and supported at four points in a way that does not interfere with normal interrogation of the reflection coefficient from any of four equally spaced locations around the pipe exterior, nor with vee path flow interrogation from external transducers such as the top pair that interrogate an outer surface of the reflector, nor interfere with the bottom pair that interrogate an inner surface of the reflector.

FIG. 9 is a side view, partly in cross section, of a relatively short cylindrical tube reflector 100 within pipe 105. The length of the reflector is less than its diameter, and it is centralized within a pipe, supported by radial finlike supports 100S1, 100S2 and two others not shown, thereby being supported by fins welded to it at four points in a way that does not interfere with normal interrogation of the reflector from any of four equally spaced locations around the pipe exterior. Neither the reflector nor its supports interfere with vee path flow interrogation from external transducers 104A, 104B such as the top pair that, as shown, interrogate an outer surface of the reflector. Nor do the reflector and its supports interfere with the bottom pair of transducers 104C, 104D that interrogate an inner surface of the reflector. Transducers 104E, 104F are located for interrogating the top and bottom surfaces of reflector 100 at normal incidence when connected to and energized by suitable electronic means such as the console described earlier. The dashed pairs of lines 105GR, 105GR are grooves to accommodate installation of the reflector with its supports. In a prototype model these grooves were made in a SS pipe by EDM (electric discharge machining).

Figure 9A:
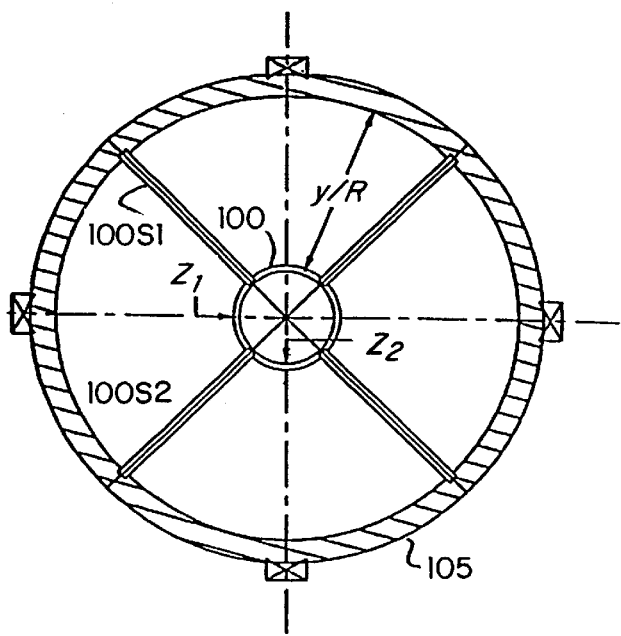
FIG. 9A is an end view of the structure shown in FIG. 9, showing transducer sites at each of four quadrants around the pipe exterior, and symbolizes by way of straight-segment arrows, an embodiment wherein the input impedance of the reflector is different, when looking into the inner vs the outer surface.

FIG. 9A is an end view of the structure shown in FIG. 9, showing transducer sites at each of four quadrants around the pipe exterior, and symbolizes by way of straight-segment arrows, a construction wherein the input impedance of the reflector is different, when interrogated at the inner than when interrogated at the outer surface. This is indicated by input impedance symbols $Z_1$ and $Z_2$. The outer surface of the reflector 100 is located at a distance y/R inward from the inside surface of pipe 105. The transducers are represented by the traditional rectangular symbol containing diagonal links. As in FIG. 9 there are four radial supports, two being denoted 100S1, 100S2.

Figure 10:
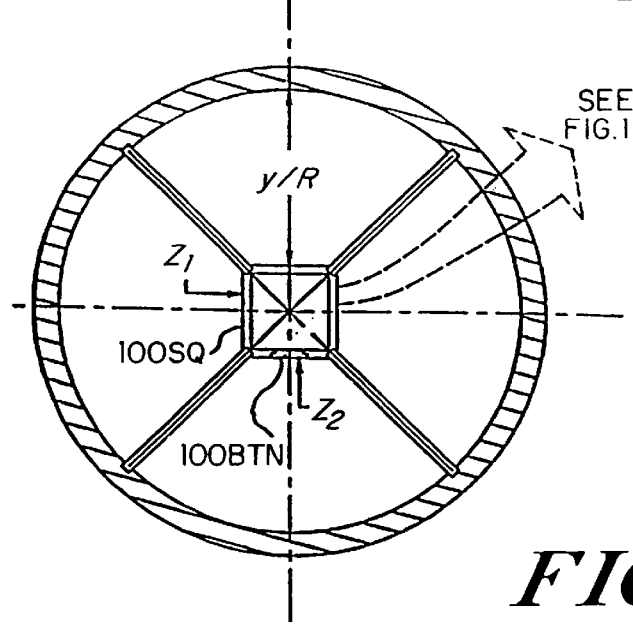
FIG. 10 is an end view of another reflector body of two different impedances, where the reflector 100SQ is of square cross section, and relatively short, typically less than its diameter, and as a numerical example may have length=½ of its diameter.

FIG. 10 is an end view similar to that of FIG. 9, of a reflector 100SQ of square cross section. The square tube reflector 100SQ is supported at its four corners, thereby allowing reflection coefficient and flow interrogations much like those mentioned above in connection with FIGS. 9 or 9A. Different input impedances are provided in the reflector 100SQ by use of a button 100BTN having a characteristic impedance $Z_2$. The rest of the reflector 100SQ has characteristic impedance $Z_1$. These details, particularly the button 100BTN, are seen more easily in the enlarged view comprising FIG. 11.

Figure 11:
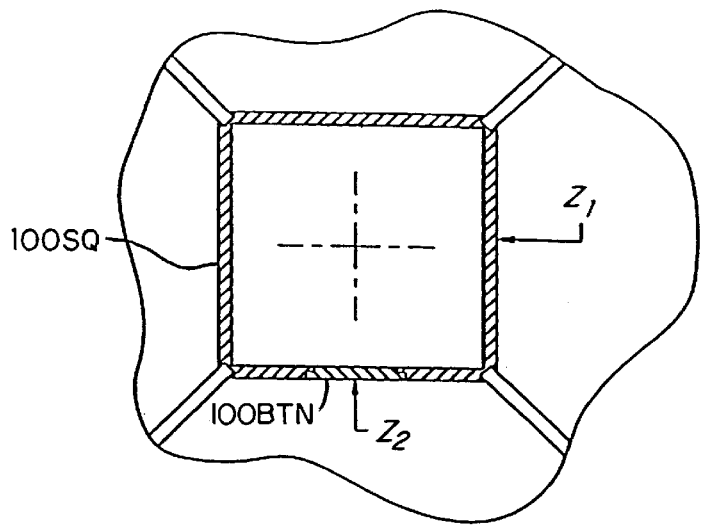
FIG. 11 shows in detail a construction of a square centralized reflector with a small insert button having an input impedance $Z_2$ that differs from the impedance of the rest of the square reflector and denoted $Z_1$; the reflective surface of the button can be made especially flat and smooth.

FIG. 11 shows a construction wherein a small insert button 100BTN provides an input impedance $Z_2$ that differs from the impedance of the rest of the square reflector and denoted $Z_1$. When the button is Ti in a SS square reflector body, the button's impedance is approximately half that of the rest of the reflector.

Figure 12:
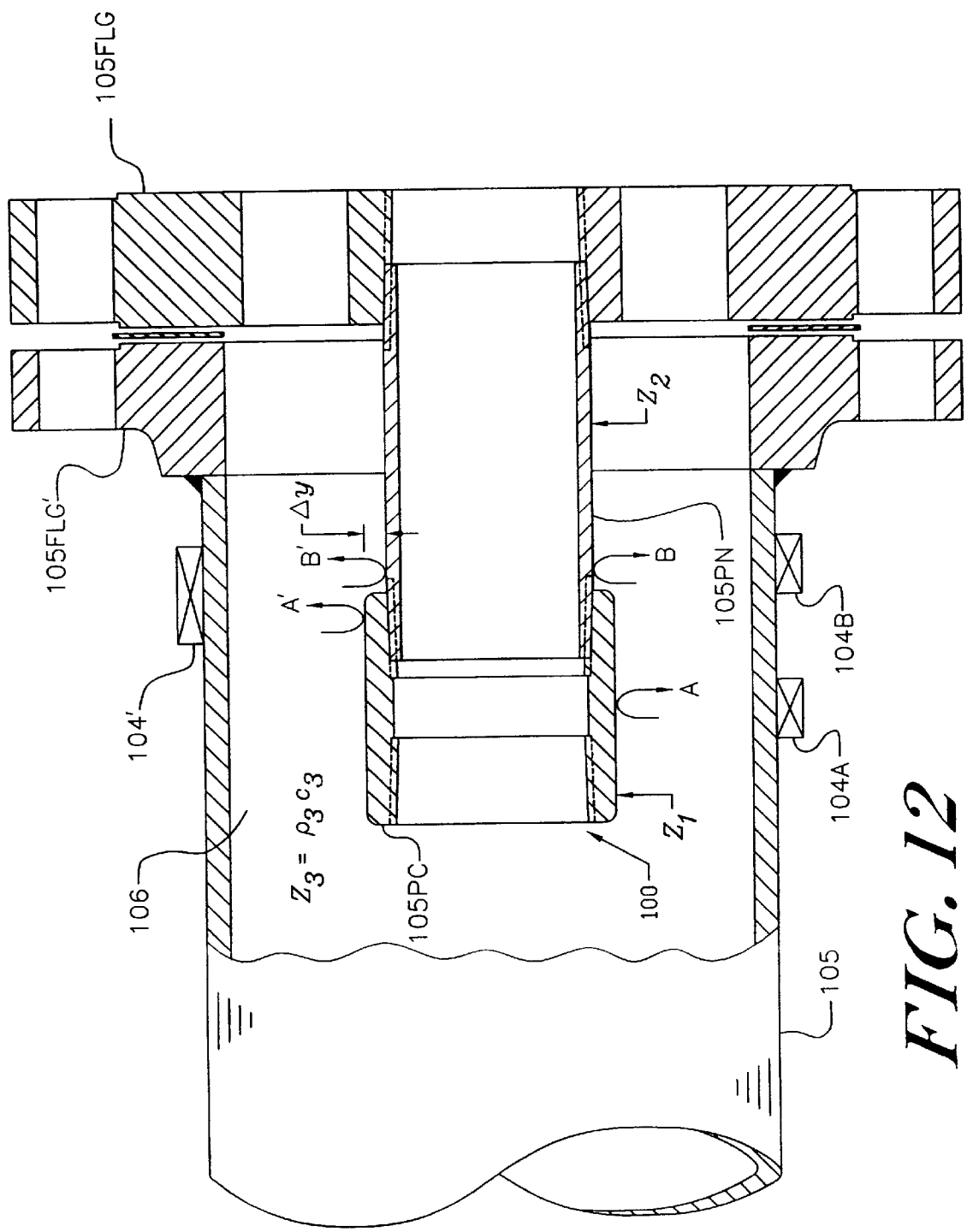
FIG. 12 is a drawing of a cylindrical multisegment tubular reflector made from standard plumbing parts, but preferably precision machined, and held in place cantilevered from a flange which is perforated in a manner that conditions the flow for flow velocity interrogation downstream.

FIG. 12 is a drawing of a cylindrical multisegment tubular reflector 100 made from standard plumbing parts, but preferably precision machined, and held in place cantilevered from a flange 105FLG which is perforated in a manner that conditions the flow for flow velocity interrogation downstream. This flange and the pipe nipple 105PN to which it is threaded, and the pipe coupling 105PC threaded thereto, bolt against the end of another standard flange 105FLG' shown welded to a pipe section 105. The fluid 106, as before, is characterized by an impedance $Z_3$. Under pipe section 105 two external transducers 104A, 104B generate echoes A&B separately. The difference in diameters Ay between the pipe coupling 105PC and pipe nipple 105PN, typically 3 to 6 mm, provides a time separation of several μs. On the top of pipe 105 there is a larger transducer 104 that straddles both the coupling and the nipple and thereby receives two echoes, denoted A' & B'.

Figure 12A:
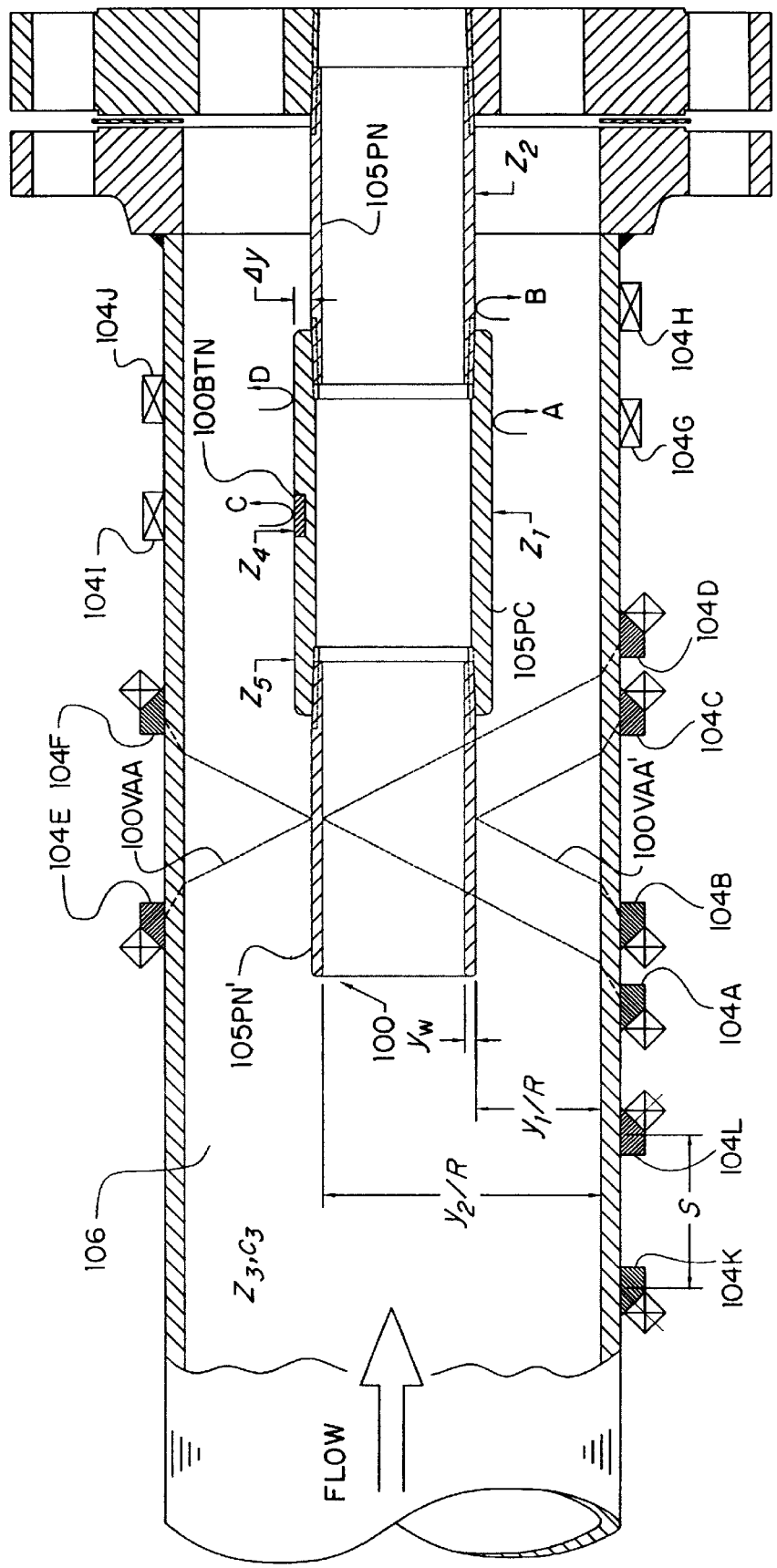
FIG. 12A is another view of a reflector having a cantilevered mounting arrangement similar to that of the one in FIG. 12.

FIG. 12A is another view of a cantilevered reflector like the one in FIG. 12. However, the cantilevered reflector assembly 100 now contains at the left a pipe nipple 105PN' which is of low enough impedance to be transmissive as well as reflective when in the fluid 106, so it can be interrogated obliquely externally and internally along several vee paths, one vee path being denoted 100VAA. The vee paths are associated with external transducers 104A, 104B, ... 104F, similar to those described earlier, and therefore carry notation similar to that of FIG. 3H. Flow velocity is obtainable integrated along paths that reflect at $y_1$ /R and at $y_2$/R, for example. Symmetry of flow can be tested by the symmetrical outboard vee paths 100VAA and 100VAA. Combining flow velocity with density leads to mass flow rate, as before.

At the lower left of FIG. 12A, external transducers 104K, 104L are utilized to measure the travel time of shear (or other) waves in the pipe wall, as the distance S between them is varied in small increments, e.g. 5 mm at a step. From the known properties of the wedges comprising these transducers, the phase velocity $c_{wall}$ of the waves in the pipe wall thereby can be determined. From $c_{wall}$ and the distance between maxima in pipe wall echo amplitudes, or wall transit time, the pipe wall thickness can be determined. Now if the piezoceramic in say transducer 104C is electroded such that an array is created, scanning the array can be thought of as equivalent to sliding the transducers 104K or 104L. This provides a method for determining pipe properties as well as fluid properties.

If pipe coupling 105PC and pipe nipple 105PN have different impedances, as well as the different diameters, then fluid density may be determined as before. If their impedances are equal, then the button method is appropriate, button 100BTN providing echo C to transducer 104I, to be compared with echo D from transducer 104J.

Figure 13:
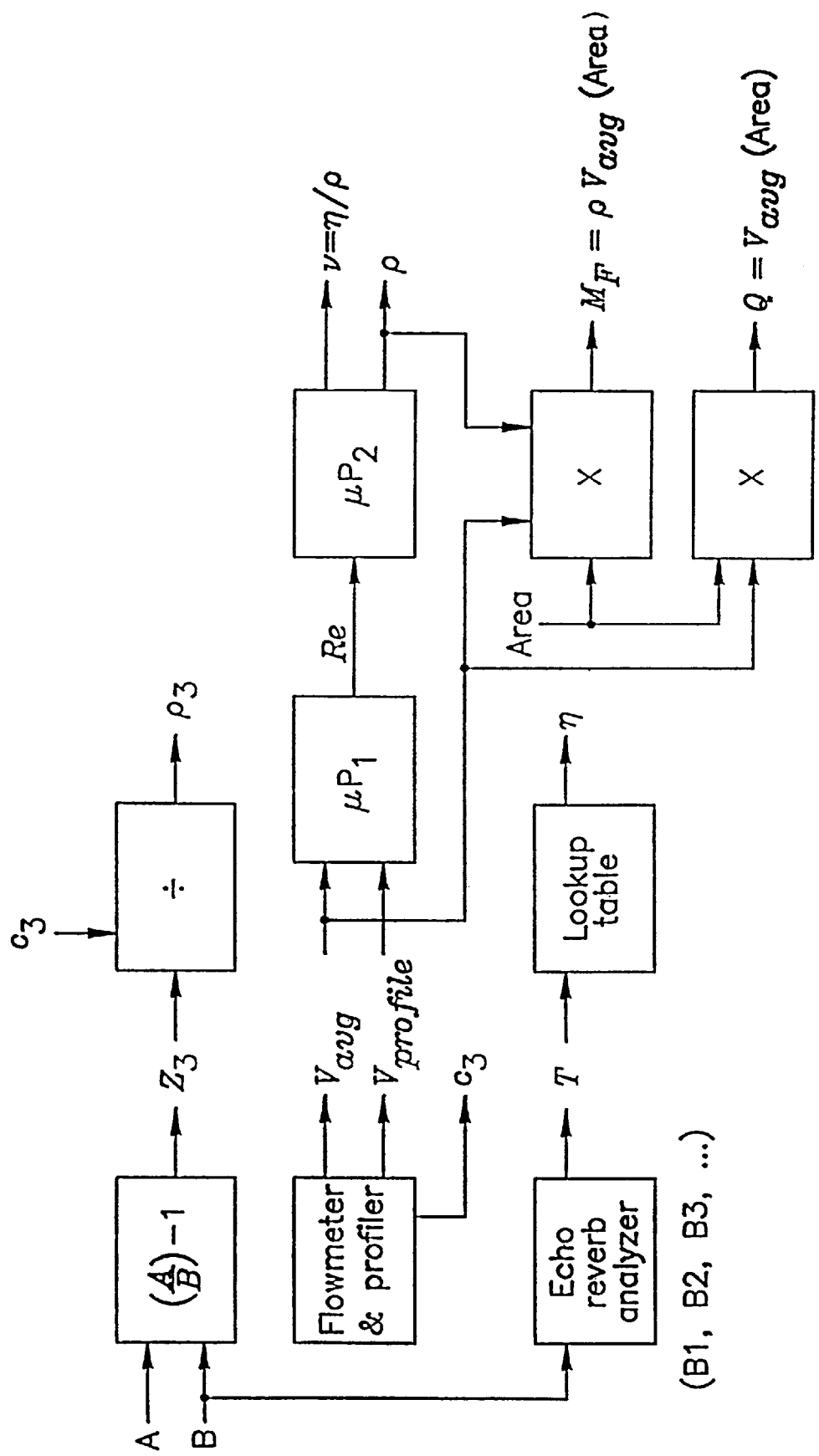
FIG. 13 is a flow chart depicting the processing of echoes A & B and sound speed in the fluid (denoted $c_3$) to yield outputs needed in process control such as fluid density (denoted $\rho_3$) and certain subsidiary measurands like kinematic viscosity ν, absolute viscosity η, Reynolds number Re, mass flow rate $M_F$ and volumetric flow rate.

FIG. 13 is a flow chart depicting the processing of echoes A & B and sound speed in the fluid (denoted $c_3$) to yield outputs needed in process control such as fluid density (denoted $\rho_3$) and certain subsidiary measurands like kinematic viscosity ν, absolute viscosity η, Reynolds number Re, mass flow rate $M_F$ and volumetric flow rate Q.

Figure 14:
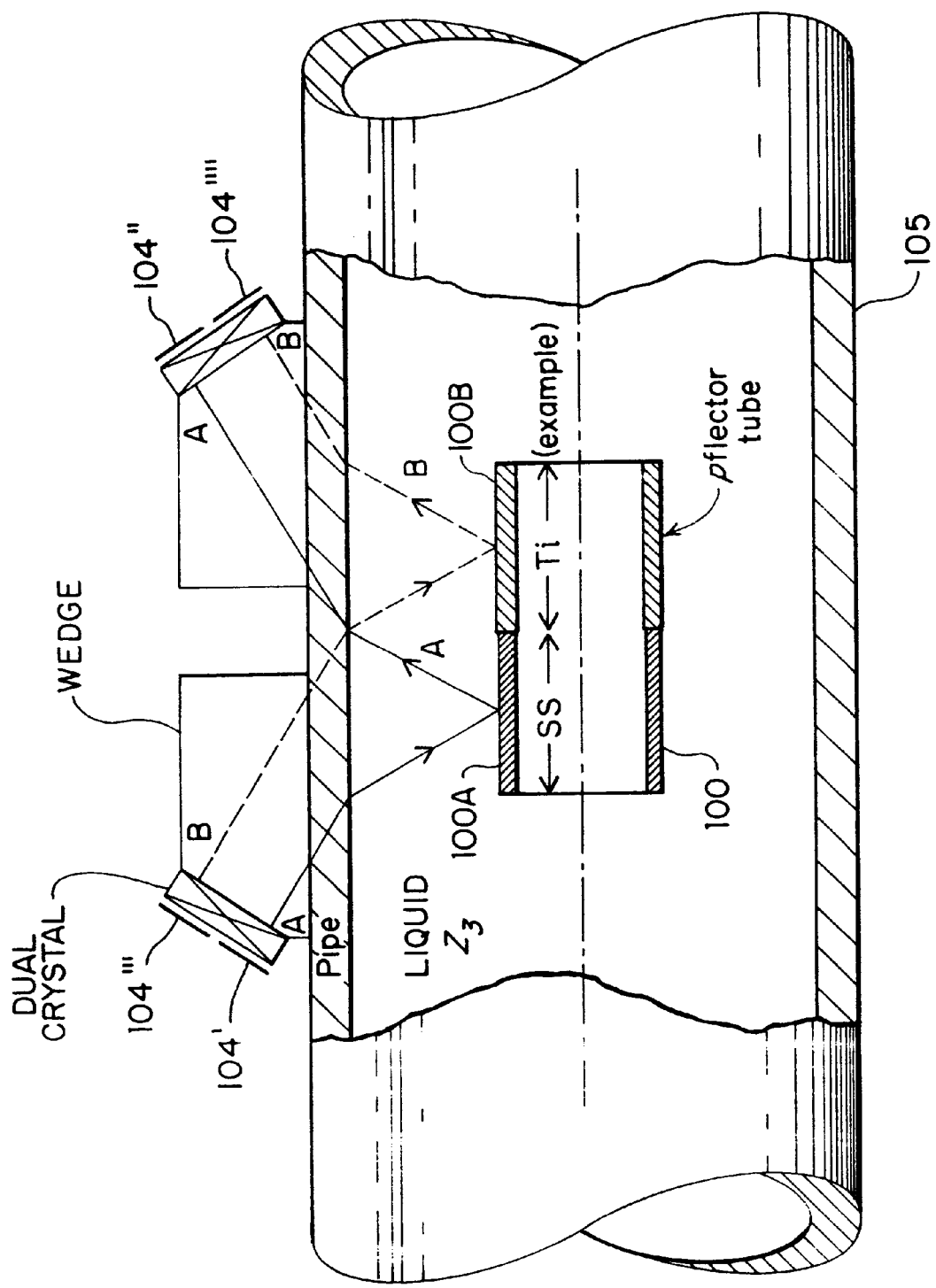
FIG. 14 is a drawing of a pipe, partly in cross section, showing a two-part reflectometer (or "ρflector" tube), comprised in this example of SS and Ti, interrogated obliquely along two different vee paths to provide two sets of echoes, A & B, which are functions of the reflection coefficients at the two different materials (SS, Ti), and also responsive to flow measured along the respective vee paths; the two paths are drawn as rays between corresponding portions of piezoceramic transducer elements that are electroded so they operate as dual elements with the upstream and downstream A portions of the respective piezoceramic elements communicating with one another, and likewise the B portions.

FIG. 14 is a drawing of a pipe 105, partly in cross section, showing a two-part reflectometer (or "pflector" tube 100) comprised in this example of a SS segment 100A and a Ti segment 100B. Each segment is interrogated obliquely along two different vee paths to provide two sets of echoes, A & B, responsive to the reflection coefficients at the two different materials (SS, Ti), and also responsive to flow measured along the respective vee paths. The two paths are drawn as rays between portions of the piezoceramics that are electroded so they operate as dual elements with the upstream and downstream A portions communicating with one another. The portion of the transducer excited by the field produced by electrode 104' communicates with the corresponding portion associated with electrode 104". Similar remarks apply to the B portions, associated respectively with electrodes 104''' and 104''''.

Figure 15:
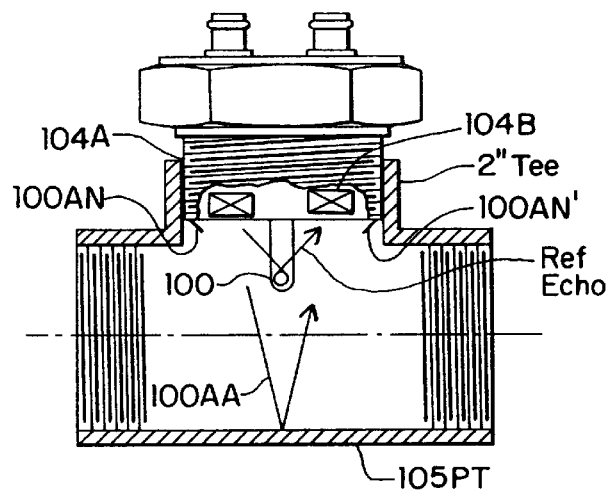
FIG. 15 is a side view, mostly in cross section, of a 2" pipe tee in which a hex plug is threaded, the hex plug containing a pair of transducers, and a bent tube serving as a reference reflector, the transducers generating beams that spread enough so that echoes are obtainable from both the bent tube and also from the far wall of the pipe tee.

FIG. 15 is a side view, mostly in cross section, of a 2" pipe tee 105PT in which a 2" hex plug is threaded, the hex plug containing a pair of transducers 104A, 104B, and a bent tube serving as a density-responsive reflector 100 that additionally provides a timing reference echo. (Conversely, if a plastic button, like button 100BTN of FIG. 11, were installed at the vertex of the vee path 100VAA, it could be more responsive to density, and then the tube, of SS, would be the reference reflector with respect to echo amplitudes.) The transducers of this system generate beams that spread enough so that echoes are obtainable from both the bent tube and also from the far wall of the pipe tee. The vee path 100VAA to the far wall provides a measure of V much as in the system shown in FIG. 6C of the above-noted '114 patent of Liu and Lynnworth, 1995. The present configuration, however, is more compact than that earlier FIG. 6c design mentioned above. Compactness is a feature found in a number of the present configurations. Further, or alternatively, a reference echo may be generated using the small 45° reflectors 100AN, 100AN' shown as not protruding beyond the projected ID of the 2" pipe tee. These small reflectors intercept a small part, approximately 10%, of the sound beams emanating from the transducers 104A, 104B. This provides a small but adequate reference signal, while allowing most of the transducer to effectively communicate with the far wall over path 100VAA.

Figure 16:
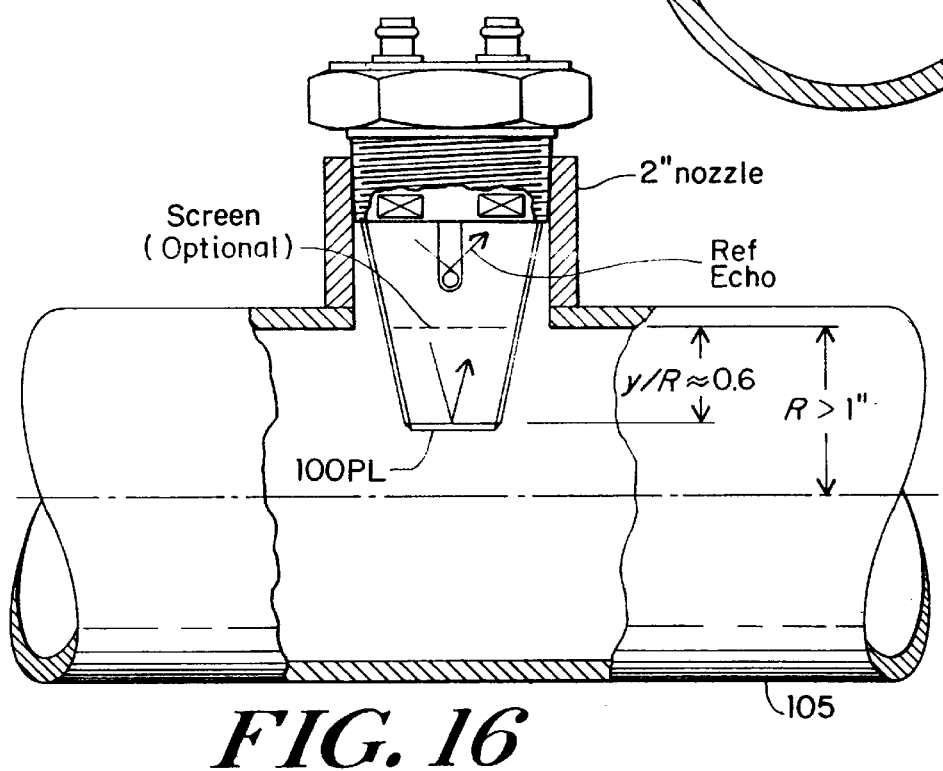
FIG. 16 is similar to FIG. 15 except the plug with transducers contains two reflectors, one like the bent tube of FIG. 15, the other resembling part of the square reflector of FIG. 10A, and with the 2" plug installed in a 2" nozzle that is welded to the side of a pipe that is usually larger than 2", for example 3" to 12" diameter.

FIG. 16 shows a system similar to that of FIG. 15, except the plug with transducers contains two reflectors, one like the bent tube of FIG. 15, the other resembling part of the square reflector of FIGS. 10 or 11, and with the 2" plug installed in a 2" nozzle that is welded to the side of a pipe 105 that is usually larger than 2", for example a pipe 3" to 12" diameter. A preferred location for the reflecting plate 100PL is at a position y/R=0.58, approximated as before as y/R 0.6. If R=6" (12" pipe example) then the preferred y/R=3.48" (3.5=88 mm.). The bent tube is recessed, out of the freestream.

Figure 17:
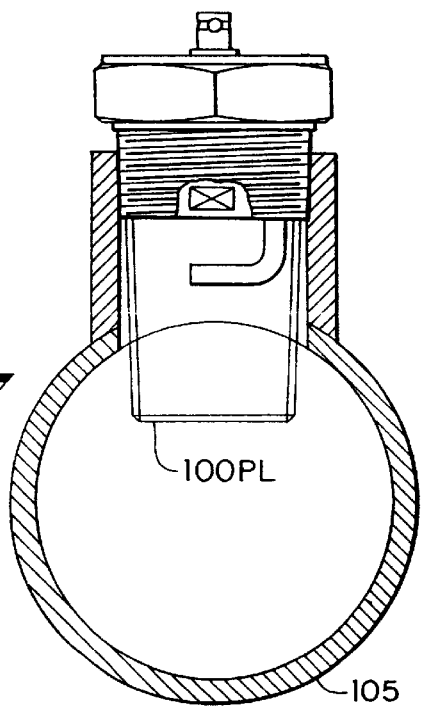
FIG. 17 is an end view of the pipe, nozzle and 2" plug of FIG. 16.

FIG. 17 is an end view of the pipe, nozzle and 2" plug of FIG. 16. The pipe 105 and nozzle are shown in cross section, and the location of the reflecting plate 100PL and the bent tube are shown as well.

Figure 18:
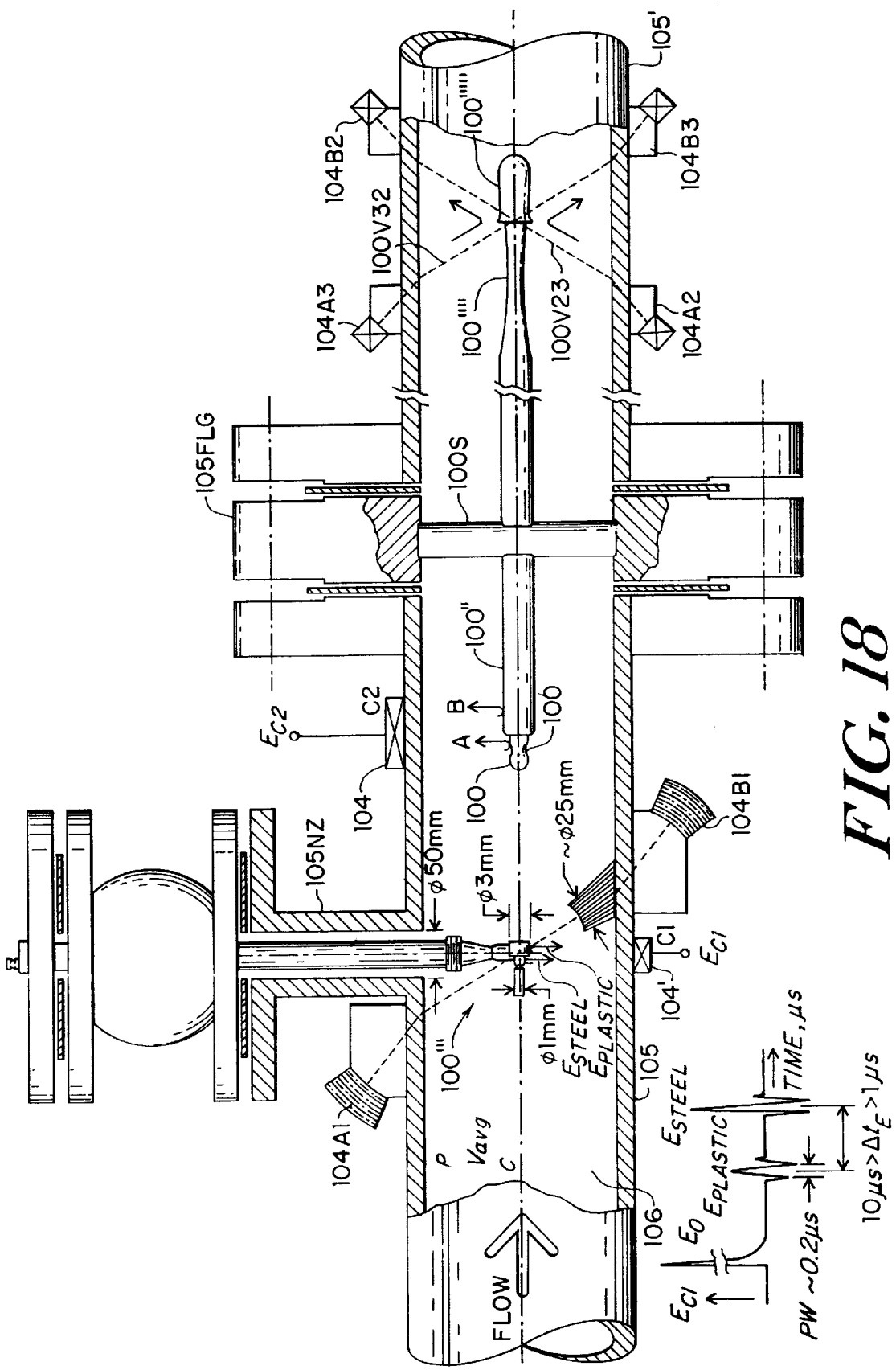
FIG. 18 is a side view of sting arrangements configured, respectively, for nozzle mounting and flange mounting.

FIG. 18 is a side view of several sting reflector configurations, including a nozzle mounting at the left, and a flange mounting at the right. The left side pipe 105 is flange-connected to the right side pipe 105" using long bolts (not shown) passing through a central thicker flange 105FLG. That flange holds a diametral supporting strut 100S, to which are welded orthogonally protruding stings pointing leftwards into the flow, along the pipe axis, and also downstream. The upstream-pointing reflective sting 100 generates echoes A&B as before, both received by a straddling transducer 104. The sting 100 contains a smaller diameter portion 100', which may be made of Ti and therefore about half the impedance of the larger-diameter portion 100" if that part is made of nickel. If transducer 104 were flat, the echoes A&B would be different largely because of their different curvatures. This undesirable effect can be reduced by making the transducer 104 of a cylindrical shape to match the contour of pipe 105. The objective is to achieve a cylindrically focussed beam.

A focussed beam is also used with sting 100 on the left side, installed through the nozzle 105NZ and associated ball valve which may be readily done using commercially available insertion methods. For density sensing, the sting 100 is interrogated from below using external transducer 104'. Echoes from the smaller (e.g. 1 mm diameter) steel portion and from the larger (e.g. 3 mm diameter) plastic portion appear as parts of the waveform $EC_{C1}$ that is sketched beneath the pipe 105. As before, the echoes are time separated and of different amplitudes, the plastic echo being smaller even though it bounces off the larger part of the sting. To measure V in the same region as density, external focused transducers 104A1 and 104B1 may be used to transmit generally across the fluid 106 despite the location of sting 100 in the path. The beam is larger than the sting and diffracts around it. In settings where it is not necessary to crowd the transducers, they are placed a bit to the left, and measure V one or two diameters upstream on the pipe 105.

Turning our attention now to the right side of the support 100S, four transducers 104A2 . . . 104B3 on the conduit 105' communicate over reflective vee paths 100V23 and 100V32 and also over transmissive paths between transducers 104A3 and 104B3, as well as between 104A2 and 104B2. A programmed ultrasonic measurement console like 109' shown in the next figure performs and synchronizes switching, so that on reflection, density is sensed, and on transmission, flow is sensed. The downstream sting has a reduced diameter for portion 100'''', followed by a termination 100''''' of larger diameter, and of different impedance. This arrangement of differently sized and positioned reflectors of different impedances that may be interrogated from multiple directions forms a compact and versatile measurement cell. The complexity of these designs is simplified in the sting configuration of the next drawing.

Figure 19:
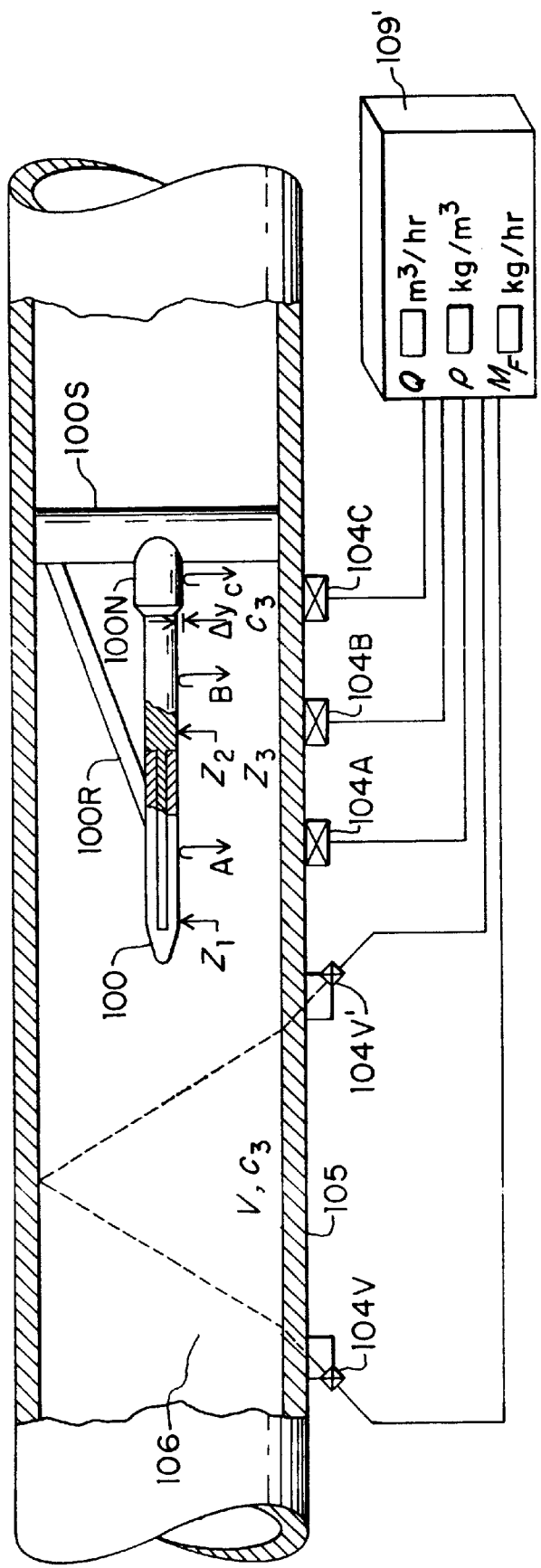
FIG. 19 shows a simple sting arrangement.

FIG. 19 shows a simpler sting arrangement. The sting consists of cantilevered reflector 100 protruding along the axial direction and orthogonal to a sting support member or diameter strut 100S. This support may be a tubular element lying across the diameter of pipe 105. The strut is firmly secured to the pipe interior. The reflector 100 has a metal core 100C of characteristic acoustic impedance $Z_2$ and a plastic cladding 100P of characteristic acoustic impedance $Z_1$ at its left end, and is attached at its right end by threading and/or being bonded to a coupler or nut 100N that itself is welded or otherwise firmly attached to the diameter strut 100S. The sting core may be made of tungsten, which is readily available in the form of an electrode rod for tig (tungsten inert gas) welding, in which case it provides an extremely high value for characteristic acoustic impedance (~100 rayls). Such tungsten (or thoriated tungsten) rods are available economically in diameters of one or a few millimeters, and of length around 150 millimeters. When immersed in water, a tunsten rod is almost totally reflective, the impedance ratio being about 100/1.5=66.7. In contrast, the plastic cladding, having an impedance 3 rayls, yields an impedance ratio in water of 3/1.5=2.] Preferably, as shown, one or more reinforcements 100R of which one is shown, are positioned around the circumference of the reflector sting to structurally support or strengthen the cantilevered mounting, while not interfering with the radial interrogation of the clad and unclad regions of the reflector. (These struts, of which only one is illustrated, act somewhat like the four supports for the cylindrical or square tubular reflector in FIGS. 9–11.) Echoes A and B are obtained as before, utilizing transducers 104A, 104B. Transducer 104C obtains an echo C from the coupler or nut 100N. Echo C arrives earlier than A or B, as the reflector for it lies closer to the wall by the differential amount Δy. This facilitates computation of sound speed c from 2Δy divided by the round trip time difference between paths for echo C and for echo B. The core material occupies the full diameter of the reflector in the region interrogated by transducer 100B, and perhaps ⅕ of the diameter in the region where echo A is obtained. This is sufficient for the core to stiffen what might otherwise be too weak a sting, if the plastic material used for the cladding were to occupy the entire cross section where echo A is obtained. The core acts like a nail having a smaller diameter near its point (perhaps ~1-m diameter) and a larger diameter (perhaps ~3 mm) near its head. As before, the respective echo amplitudes A & B may be combined as (A/B−1) to yield fluid impedance $Z_3$ and then fluid density $\rho_3$. The impedance of the coupler is not critical, so long as it is reflective enough to yield an echo for timing, such that c can be determined, if in fact c is to be determined in this way. It may be more convenient and even more accurate to obtain c in accordance with a further aspect, discussed next.

External transducers 104V, 104V', as before, measure flow velocity V along a vee path, and they also yield the sound speed c, with both V and c being determined by well known methods. The section of pipe 105 may be terminated at each end with standard flanges (not shown). Alternatively the pipe ends may be terminated with pipe threads or with other standard sealing and suitable junction, depending on the pipe size and pressure rating. FIG. 19 therefore schematically represents a calibratable spoolpiece containing a simple sting, whose purpose is to measure the mass flow rate of fluid 106, plus some other parameters, utilizing the programmed electronic console measuring device 109'.

Figure 20:
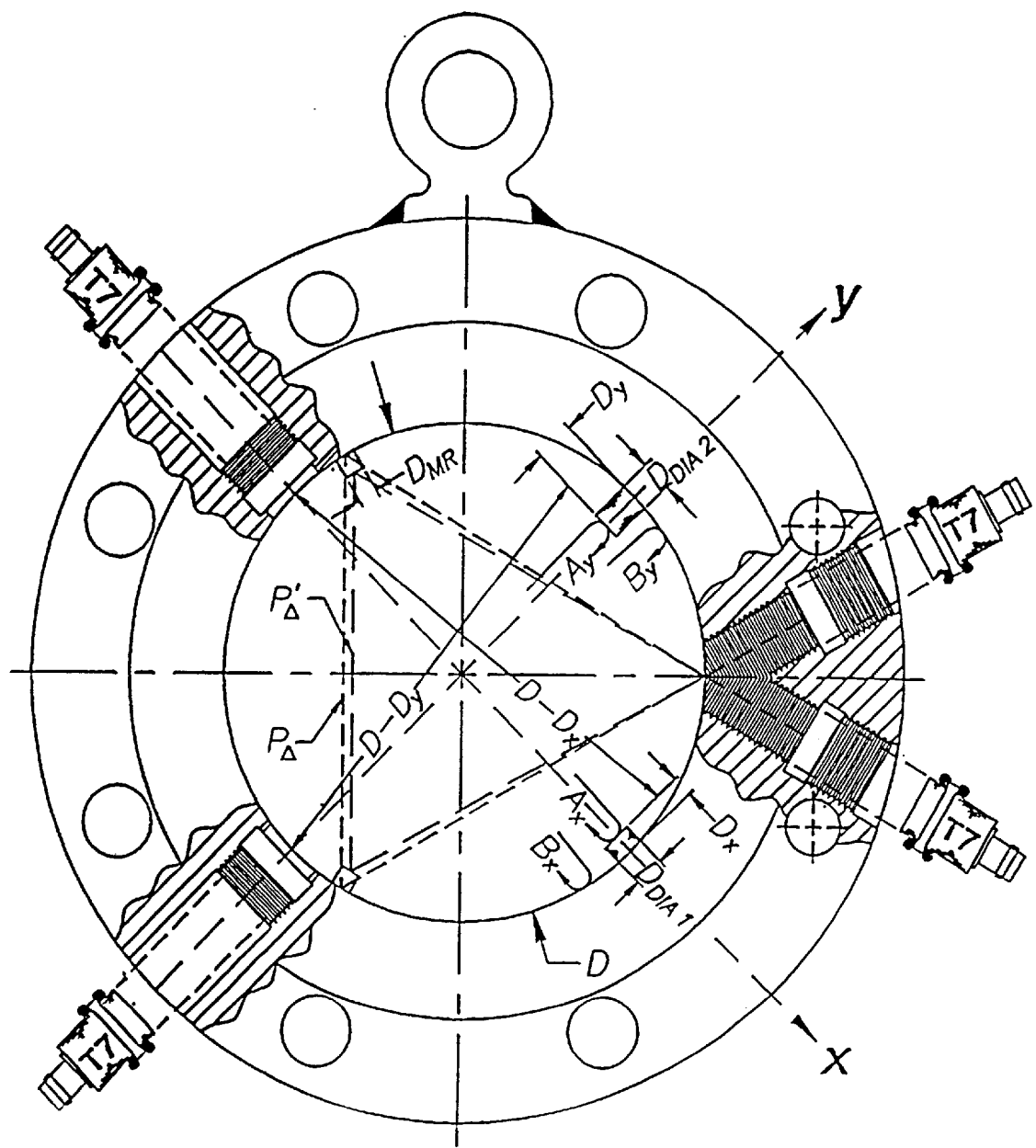
FIG. 20 is an end view of a flange containing measuring paths primarily in a plane perpendicular to the axis of the pipe system in which this device is to be installed, wherein the paths include diameter and off-diameter paths, reference paths, and paths reflecting from reflectors protruding slightly into the flowstream by different amounts.

FIG. 20 is an end view of a flange adapted in accordance with the present invention, and configured with measuring paths primarily in a plane perpendicular to the axis of the pipe system in which this device is to be installed. These paths include diameter and off-diameter paths, reference paths, and paths reflecting from button-like reflectors protruding slightly into the flowstream by different amounts. FIGS. 21–24 discussed below, present simpler versions containing only one or two of the numerous density-responsive paths of FIG. 20. The illustrated flange has four transducers and four paths. Two of the paths, each using a single transducer, are on or near the diameter, oriented along the x and y axes. Echo $A_X$ bounces off a protrusion of diameter $D_{DIA\ 1}$ which protrudes radially in from the flange wall by the amount $D_x$. A portion of the incident beam strikes the flange wall around the protrusion, returning as echo $B_X$. By employing a protrusion of plastic and the flange is steel, these two echoes are a basis for determining fluid impedance in the vicinity of that protrusion. Similar remarks apply for the protrusion along the y axis. This figure also shows two triangular paths, denoted P and P'. Here the purpose is to increase sensitivity to fluid density $\rho$ by utilizing bounces off two protruding reflectors, of which one is shown having a diameter $D_{MR}$. This achieves an increase in sensitivity akin to that achieved with the plastic or plastic-coated corner reflecting vee block of FIG. 3A. All four transducers are indicated by T7, which is simply the commercial designation of the transducers utilized in a prototype flange construction. Their construction and method of installation are described in an article by one of the applicants and his colleagues, in the September 1997 issue of *IEEE Trans UFFC*, 44(5) pp. 1087–1100. FIGS. 21–24 illustrate other constructions for simplified aspects of the system, containing only one or a small number of paths.

Figure 21A:
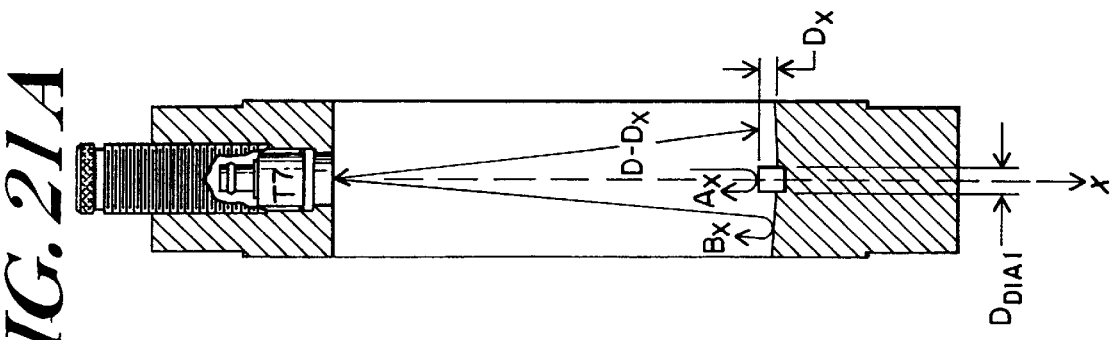
FIGS. 21, 21A show a simplified portion of FIG. 20, illustrating only a set of the paths on or near one diameter.
Figure 21:
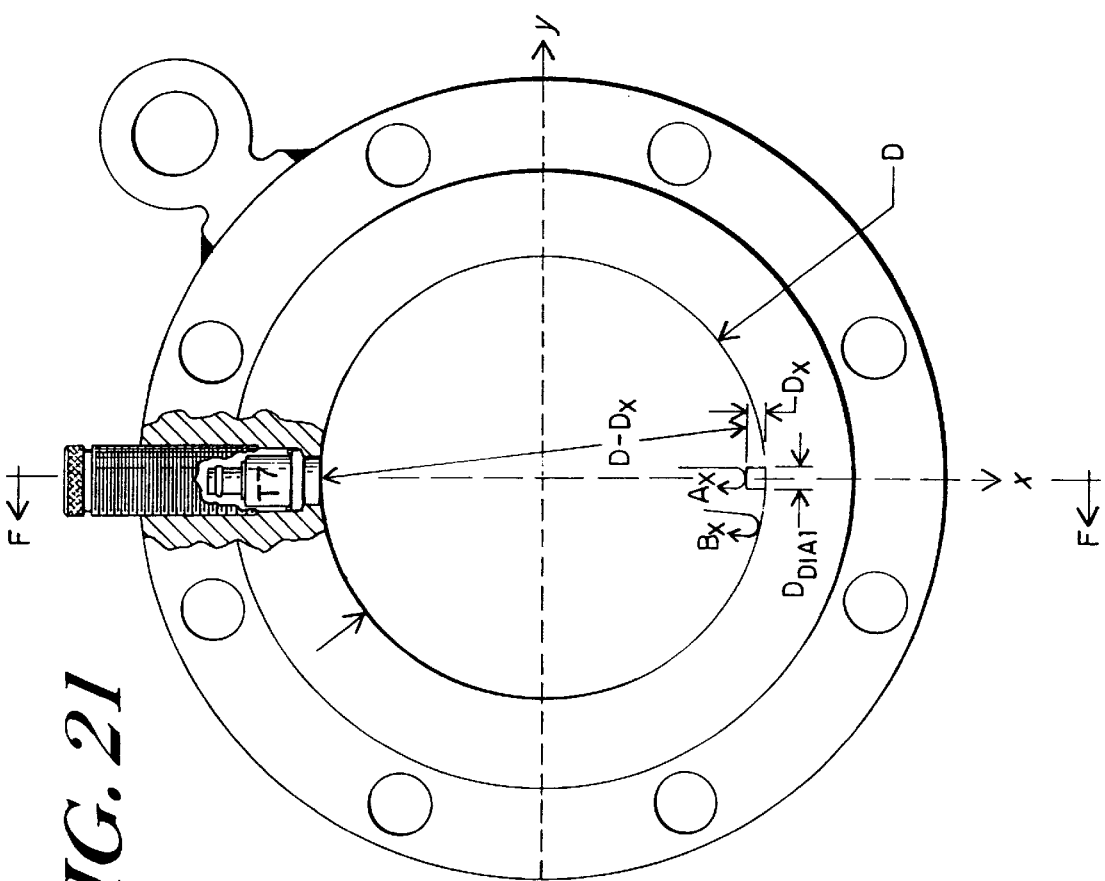

FIG. 21 shows one such simplified assembly, containing paths on or near one diameter. Consider only the paths yielding echoes $A_X$ and $B_X$, generally along the direction of the x-axis. The echo $B_X$ tends to be refocused back to the T7 transducer by the curvature of the flange in the x-y plane. This effect is here reinforced by beveling or curving the flange along the orthogonal (axial) direction, as shown more clearly in FIG. 21A. Here the $B_X$ echo is taken as the reference echo. The protrusion yields a round trip time difference equal to $2D_x/c_3$.

Figure 22:
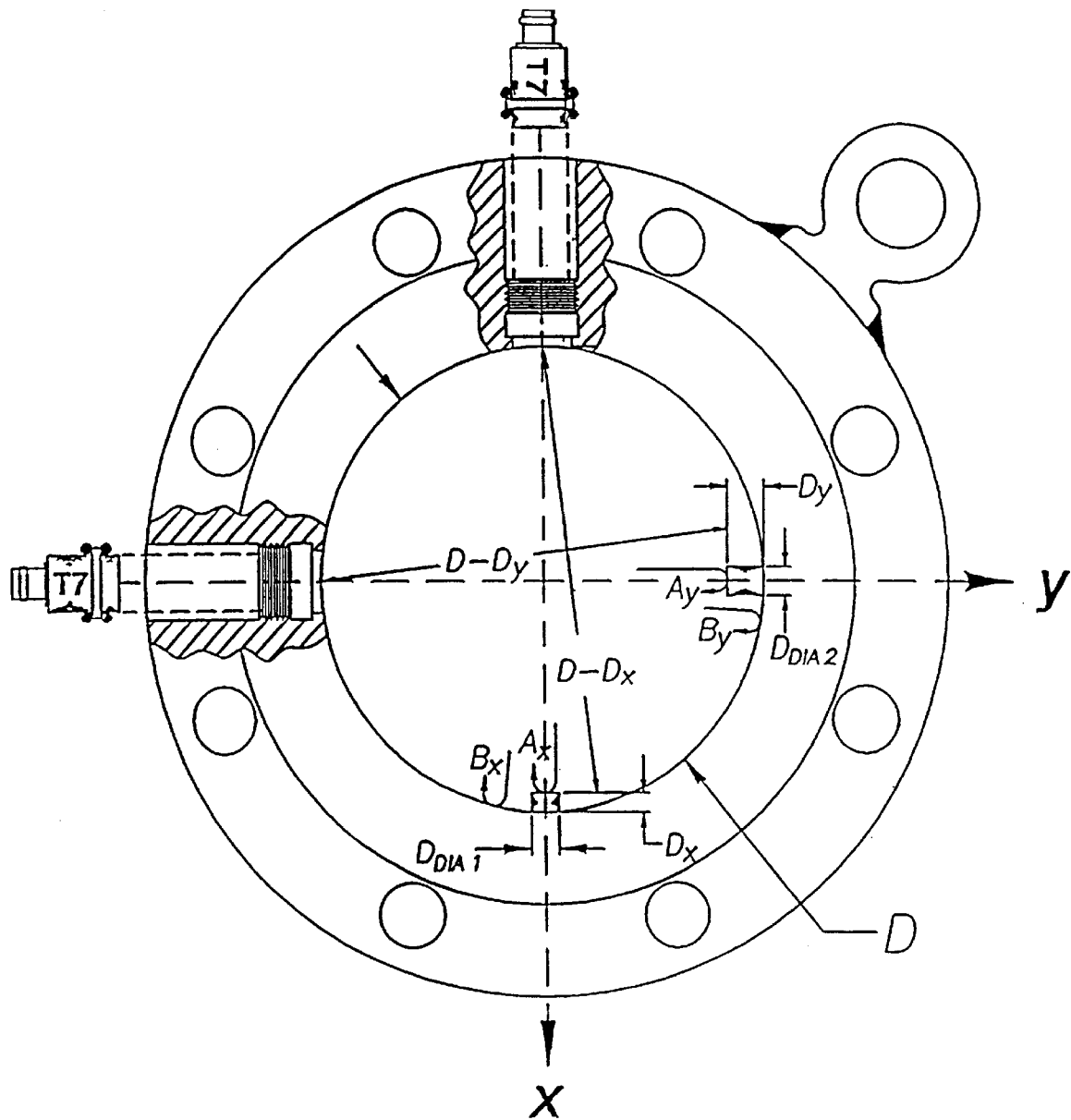
FIG. 22 is another simplified portion of FIG. 20, showing paths on or near two diameters.

FIG. 22 shows an embodiment having a second transducer and a second pair of paths, located generally along the y-axis. The y-axis protrusion is $D_y$. It is not necessarily equal to the x-axis protrusion $D_x$. This creates a differential path across the fluid, and may be used to partly compensate echo amplitudes for attenuation effects in the fluid, or to determine density differences at the two different protrusion sites.

Figure 23:
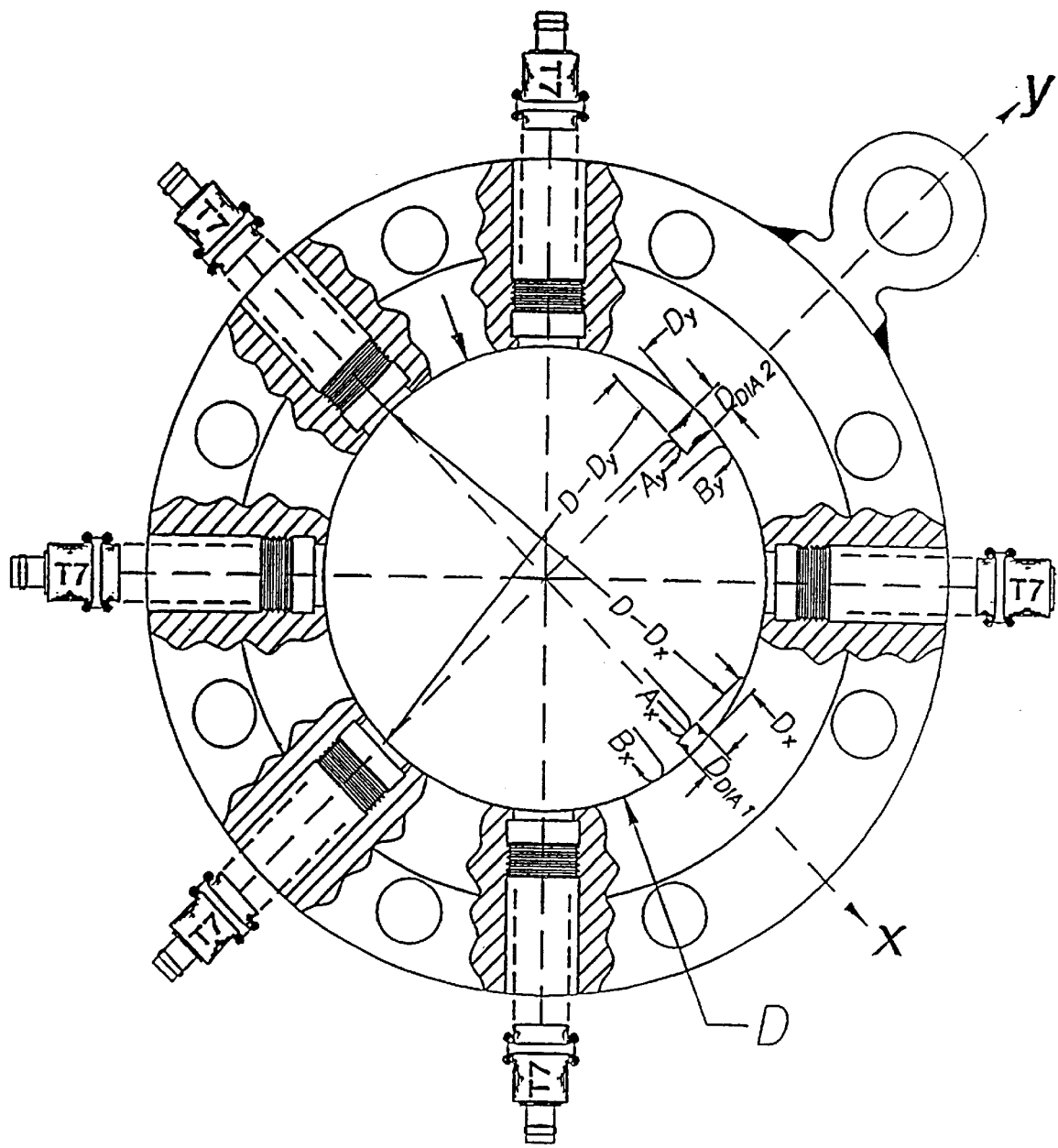
FIG. 23 is another simplified portion of FIG. 20, containing paths on or near one inscribed equilateral triangle.

In FIG. 23 there are, in addition to the transducers associated with the two protrusion x- and y- paths, four T7 transducers situated on paths midway between the x- and y-axes. These mid-axis paths are used to measure cross flow by means described in the applicant and colleagues' 1997 *IEEE Trans UFFC* paper cited earlier. In other words this flange system combines density sensing with sensing of the secondary components of flow.

Figure 23A:
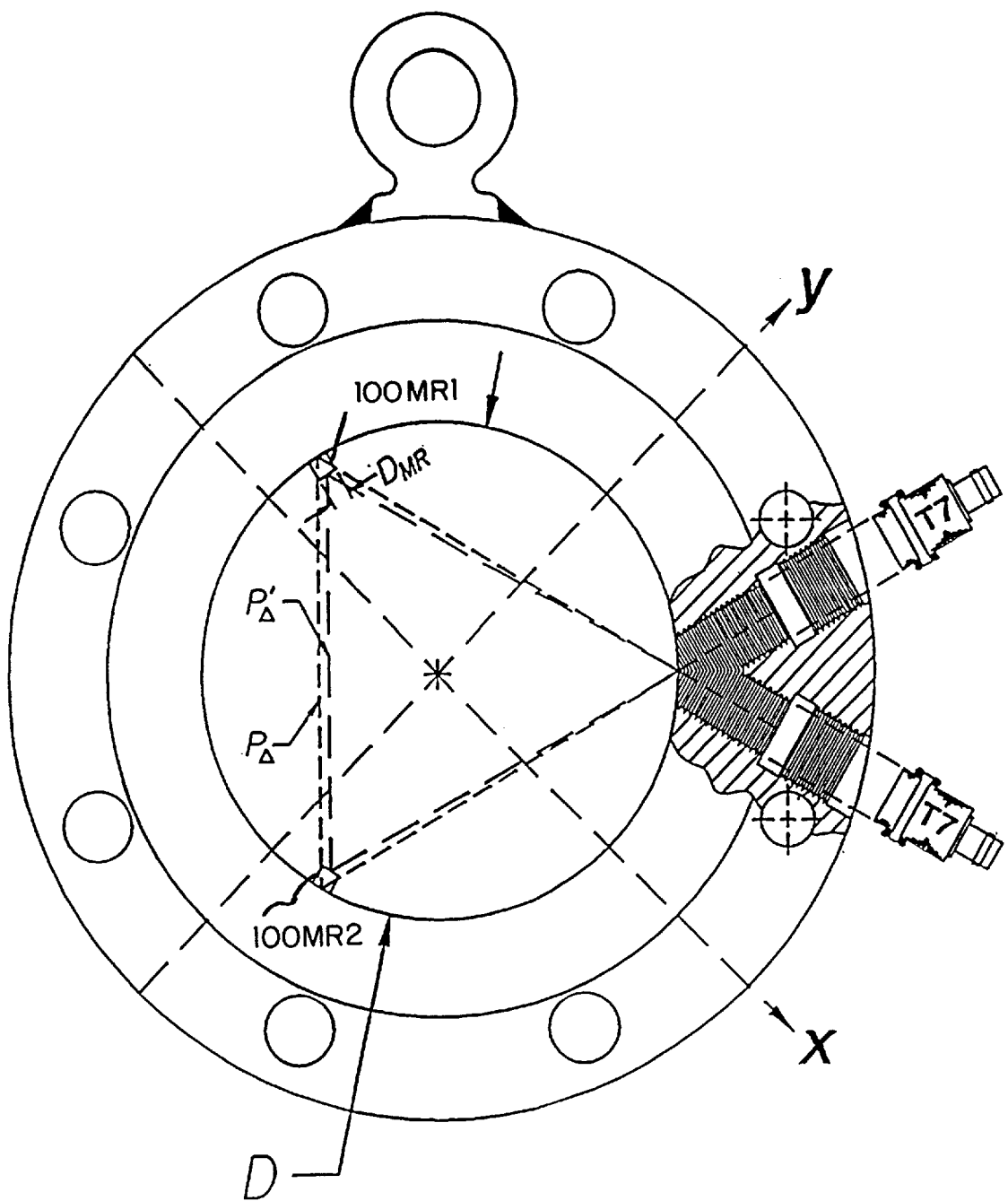
FIG. 23A is an end view like FIG. 22 except it includes provision for measuring crossflow as well as the reflection coefficient.

FIG. 23A shows another simplified flange construction, which contains paths on or near one inscribed equilateral triangle. The inner path interacts with the two protrusions, while the outer path bounces off the inner wall of the flange. The illustrated path is often called the triple midradius path since the chord segments are tangent to a circle of diameter D/2, or of radius R/2 if D=2R. Only two transducers are used in this simplified susbsystem of the device of FIG. 20.

If the flange in FIG. 23A is thick enough, e.g. 50 to 75 mm thick, then it can accommodate T7 transducers placed side by side in the axial direction, rather than circumferentially, with an axial displacement of about 30 mm between transducer centerlines. A side view would resemble FIG. 16. As in that earlier figure, axially-displaced transducers can measure the primary component of flow, which when multiplied by density and pipe area, yields mass flow rate. This is one preferred configuration. If facets on the transducers, or on the reflecting surface of the flange, can also generate off-diameter paths, then possibilities exist to obtain velocity ratios that weight the profile differently and allow profile reconstruction by tomographic or other means, for example by the method described in the U.S. patent application of Robert H. Hammond, Ser. No. 09/412,236, bearing filed on Oct. 4, 1999 and entitled for Ultrasonic Measurement System with Chordal Path.

Figure 24:
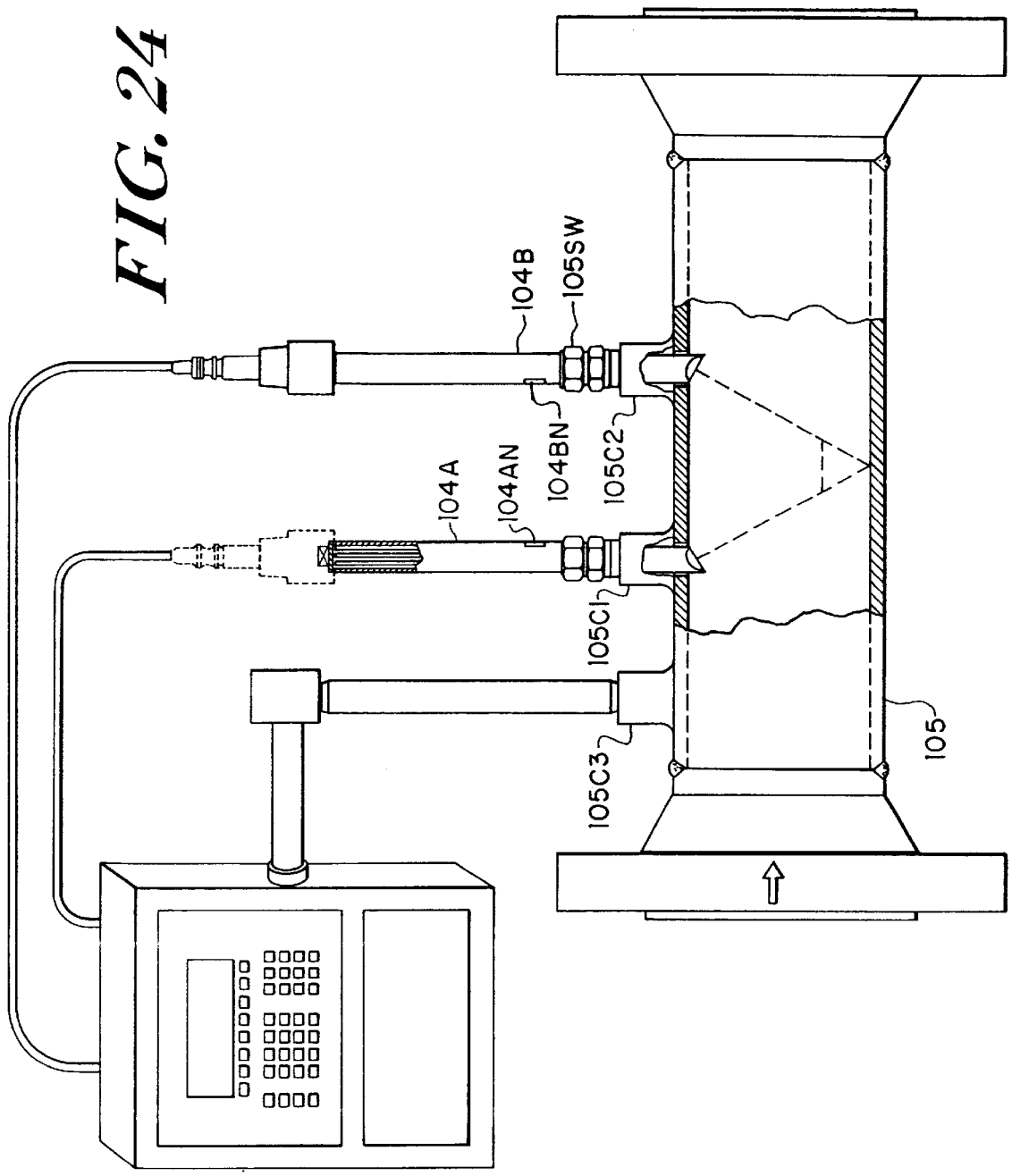
FIG. 24 and FIGS. 24A–I comprise a set of drawings showing ways of sensing along a diametral path and off-diametral paths, including rotated GC paths.
Figure 24A:
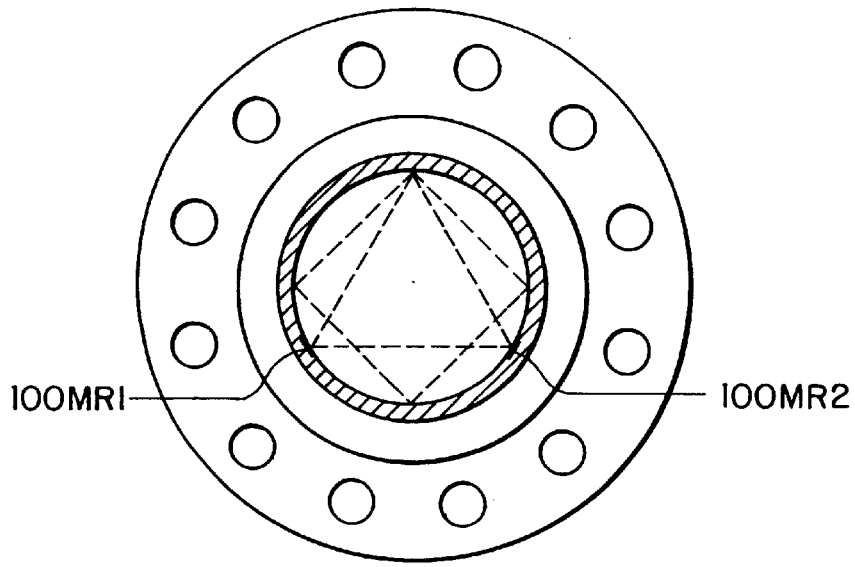

FIG. 24 shows a spoolpiece consisting basically of a pipe section 105 welded between welding neck flanges. The pipe 105, which may have a diameter 6 inches (as a numerical example), has two ports, or holes, each of diameter approximately equal to the inner diameter of the couplings 105C1, 105C2, which are each welded to the pipe 105. These hole diameters may be about 30 mm. Standard swage-type compression fittings 105SW thread into the couplings and secure transducer assemblies 104A, 104B of the types shown in FIGS. 24B–D. These transducer assemblies may be of the bundle type as described in U.S. Pat. No. 5,962,790 of inventors Lynnworth and Liu, and also described in Liu, Lynnworth and Zimmerman, *Ultrasonics* Vol. 36, pp. 305–315 (February 1998). As shown in FIGS. 24C–D, these transducers may be constructed with three and five facets. Note that, when installed in the pipe, at most only one facet in any assembly radiates in a plane containing the major axis of the assembly and the pipe axis. The purpose of these facets is to radiate along diametral and nondiametral tilted paths such as those shown by dashed lines in the end view, FIG. 24A. The dashed lines form an inscribed equilateral triangle corresponding to the well known spiraling midradius path. Two vertices of the triangular path reflect off inserts 100MR1 and 100MR2, which can be plastic in order to increase sensitivity to density. The dashed lines, representing rays launched from a different set of angled facets, can also form the inscribed square, when viewed in the end view. The transducer assembly of FIG. 24D with five facets provides both of these inscribed geometries. The actual paths are not squares or equilateral triangles, and depend on the axial spacing of the transducers in FIG. 24. By arranging for the multipaths as illustrated, this configuration provides (a) a combination of different numbers of reflections, controllably off metal pipe or off plastic or other inserts, to respond to fluid density; and (b) interrogation of flow along plural paths that differ with respect to how they sample the flow profile, and are thus analogous to quadrature or other multipath solutions to measuring average flow despite unknown flow distributions, e.g., disturbed flow conditions. These two features are obtained with only two ports, and only two transducers. In a preferred embodiment, the paths are arranged so that the signals over different paths arrive at separated times, and a single-channel ultrasonic flow meter, represented as Panametrics' Model DF868, suffices for the determination of one or more of: fluid density; average flow velocity (using multichord data); mass flow rate. Coupling 105C3 provides for easy mounting of the electronic console by conventional means, e.g., pipe fittings. Alignment notches 104AN, 104BN, on the transducers, are useful in achieving the paths oriented as shown in FIG. 24A. The idea of using only one electronic timing channel to time transmissions over different paths is itself not new, having been described for example in Lynnworth, U.S. Pat. 5,515,733 (issued May 14, 1996) and is referred to as the N-banger method.]

Figure 24B:
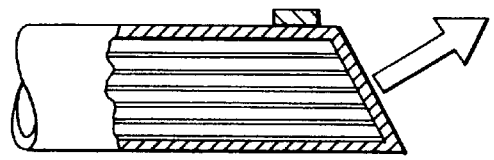
Figure 24C:
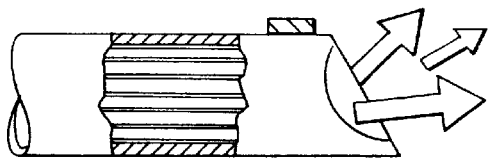
Figure 24D:
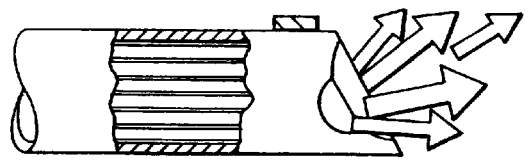

The transducer of FIG. 24B may be installed radially like one of the T7 transducers in FIG. 23, through a radial port in a thick flange. By rotating such a beveled transducer until it radiates in the plane of the flange, a clockwise (cw) path is radiated and a circulation-sensing signal can be picked up at a diametrically opposed port by another similar transducer. Next, if both transducers are rotated 180° about their common axis, a counterclockwise (ccw) measurement is obtained. From the difference in travel times, $\Delta t$, as measured cw–ccw, the circulation $\Gamma$ can be computed, proportional to $c^2 \Delta t$.

Figure 24E:
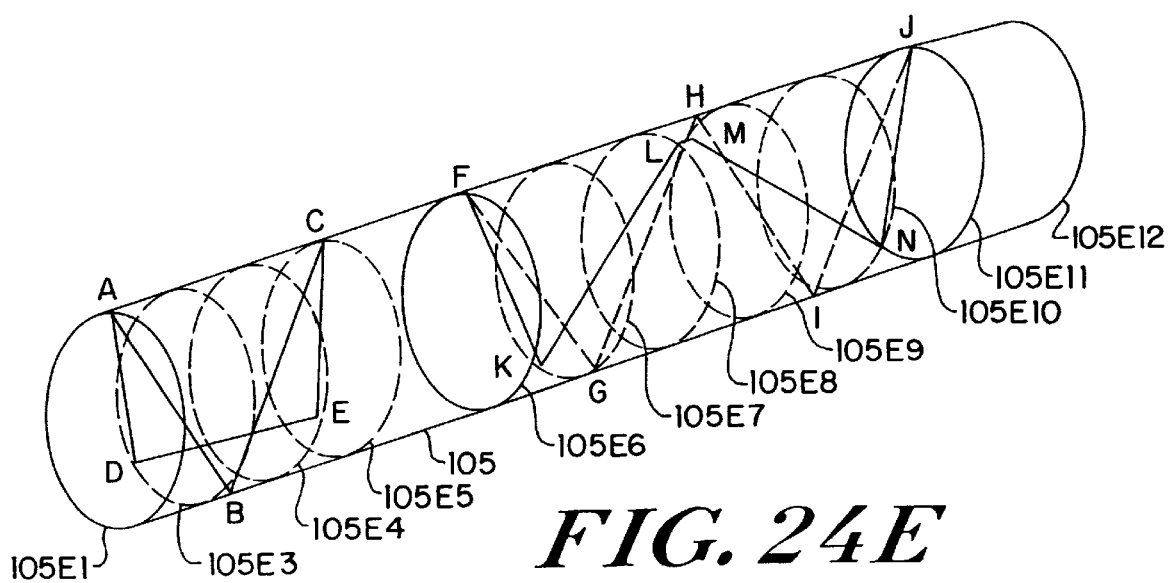

We next investigate whether some of the features of FIG. 24 can be achieved without any penetration of the pipe 105. Referring now to FIGS. 24E, F and G, consider pipe 105 to be truncated at its ends 105E1, 105E2 in planes perpendicular to its axis, and for simplicity, let the pipe in FIG. 24E have zero wall thickness. The cut ends appear as ellipses in FIG. 24E, as do certain construction aids 105E3 . . . 105E11. The construction aids represent intersections of planes perpendicular to the pipe in sets of equidistant cuts.

Figure 24F:
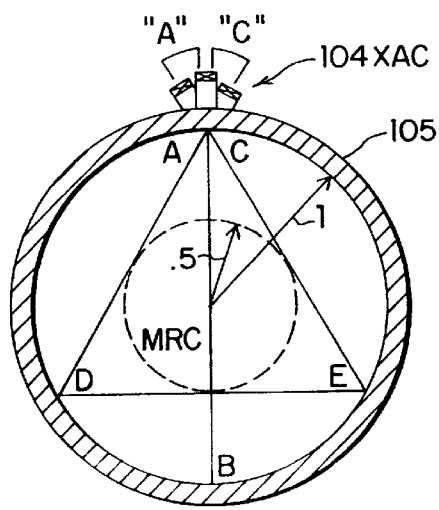
Figure 24G:
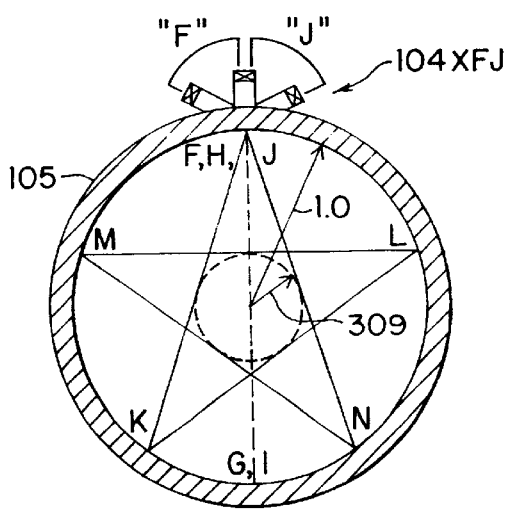

Imagine now a source at A and a receiver at B. Further, let a tilted diameter path follow the route ABC in FIG. 24E or F. Let a midradius path follow the route ADEC. We have the special situation of two different and particularly useful paths achieved using only two transducers. In FIG. 24F we depict the source of ray AB and AD by a symbol marked "A". Similarly we depict the receiver by symbols linked by the mark "C". In practice the source and receiver are each capable of transmitting or receiving. We are not concerned here, with details of their construction. These may be "hockey stick" buffered transducers of the type described in applicant's copending U.S. patent application Ser. No. 08/879,690. Particularly thin angulated constructions are appropriate for the measurements indicated here. To achieve the path ADEC from outside, the pipe must have low sound speed, e.g., must be a plastic, or other material of similar sound speed. Brass pipe works with some liquids. If the pipe is steel, then the fluid inside must have a high c, (e.g., above about 2000 m/s) to refract along midradius chords. For reference, we show a dashed circle inscribed within the triple midradius path. That circle, labeled MRC, is shown with a radius of 0.5 in a pipe of inside radius 1. In contrast, in FIG. 24G, we interpret the pipe 105 in that figure, again having an inside radius of unity, to be steel. Steel limits refractive angles, thereby preventing midradius interrogation but allowing some other paths. One of the other paths of interest is the inscribed star, which, although not considered novel by itself, is considered novel when combined with a tilted diameter path in such a way that both the tilted diameter path FGHIJ arrives at essentially the same axially-displaced location as does the star path FKLMNJ. Again, these arrivals are time-separated, allowing separate measurements of flow over each path, as well as differential reflectivity measurements. For reference, the inscribed dashed circle is shown with radius 0.309, a numerical approximation to $\sin(\pi/10)$.

This invention recognizes that the diameter path and the off-diameter paths can arrive close together in space, if suitably aimed down the pipe, allowing their measurement with only two transducers. Can the job be done with only one transducer? Analysis of FIG. 24G, including the possibility of a multi-angle transducer and/or special facets on the pipe interior, indicates that it is possible in principle. All measurements would have to be confined to a relatively short L, which may require fitting the measurements within the space normally occupied by a flange that is not more than about three times the normal flange thickness, for a given pipe size. The practicality of this construction will in practice depend on pipe diameter, sound speed in the fluid, transducer ringing, and the degree of time resolution sought for the different paths.

In FIG. 23A, where the midradius path strikes the pipe ID, if it is desired to increase the sensitivity to fluid density, inserts 100MR1, 100MR2 can be provided, of plastic or other material, similar to the reflector buttons described for the previous figures. In FIG. 24F, the outside of the pipe surface may be roughened in the vicinity of the reflection points D and E so that, if the fluid is a liquid, reflections will be obtained principally from the inside surface only.

If the density-sensing region is flush, and yet some cleaning action is desired, this may be achieved this by arranging for the pipe to be of somewhat smaller diameter than the upstream and downstream piping. This may be similar to the tapering in some conventional flow cells used to flatten the flow profile. In this construction, the "flush" reflecting surface is somewhat inside the projected ID of the upstream and downstream piping. Another alternative is to direct high-intensity ultrasound at the reflectors, to clean them by acoustic streaming. As used herein, applicant intends the term "stream cleaned" to encompass this latter mechanism also.

Figure 24H:
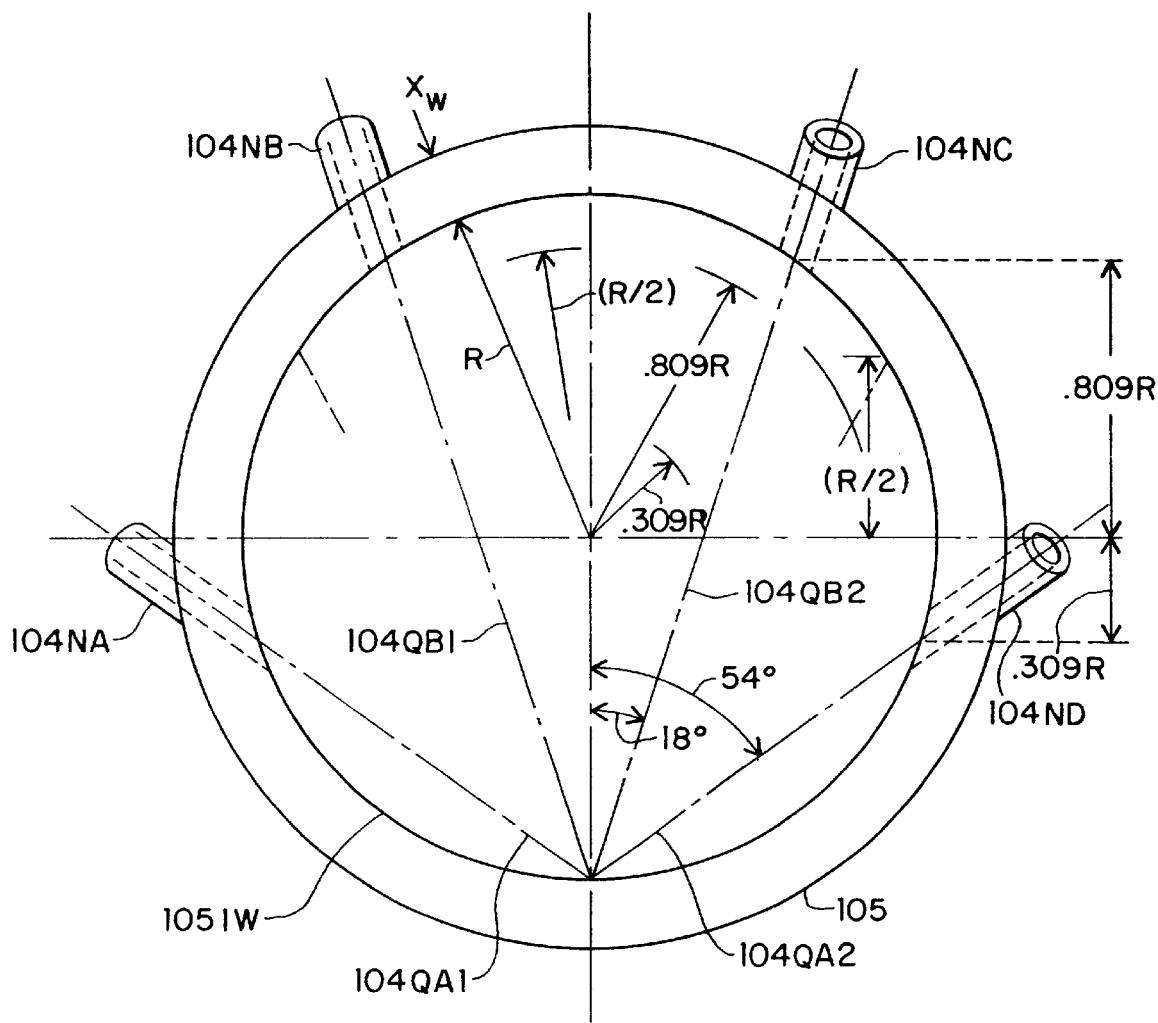

A system having special reflective interrogation paths may also be implemented with another form for the central pipe section between two flanges, as illustrated by the end and side views comprising FIGS. 24H and I. The paths in this section of pipe are positioned to accurately sense the flow velocity using paths like those used in earlier quadrature methods (Malone and Whirlow, 1971, or Wyler, 1976, cited earlier). In these two figures, the GC paths can be located by requiring them to be tangent to certain construction cylinders (circles in the projected end view) having radii for example of 0.309R and 0.809R, for a pipe of internal radius R. The vertices of all paths preferably coincide, but they may also be staggered, with staggering in the axial direction being preferable. Beyond that, several additional options may be employed, according to the severity of secondary flow. Absent secondary flow, the few paths in FIGS. 24H, I suffice. If crossflow and swirl are strong, then additional paths or interrogations are preferably implemented to obtain averages, or, alternatively, one may use the rotated GC paths illustrated but add crossflow and circulation or swirl sensing paths as in FIG. 20, utilizing up- and downstream flange-mounted transducers, or using a plane perpendicular to the pipe axis and also passing through the common vertex point. A circulation-sensing triangle path for gases is illustrated with acoustically-isolated transducers in Lynnworth, U.S. Pat. No. 5,437,194, issued Aug. 1, 1995, in FIGS. 18–19 thereof.

However, beyond the objectives stated above, the construction may use fewer ports and use fewer transducers, for the same number of paths and yet retain the distances those paths are "off" the diameter. This may be done with simple, single-reflection vee paths as shown in end view in FIG. 24H. Referring to the LHS (left hand side) of the pipe, lying left of the vertical centerline, and to the RHS (right hand side) lying to the right of that centerline, it will be seen in this figure that four nozzles 104NA . . . 104ND are shown, having holes drilled through them and continuing through the wall of pipe 105 to generate four ports. These are placed such that transducers (not shown, but of types well known in the art) installed in the ports communicate over the vee paths, which may advantageously be vee quadrature paths, each having a first and a second leg, denoted 104QA1, 104QA2, 104QB1, 104QB2. Illustratively, the pipe has an internal radius R and wall thickness $X_W$. Construction circles are drawn having radii 0.309R and 0.809R to illustrate a set of reflected quadrature paths, which, as shown are symmetrically located about a diametral plane centerline, and make angles of 18° and 54° with that centerline. The paths are tangent to the construction circles. These illustrated paths are the same distance in from the wall, or the same distance from the pipe axis, as the well known Gauss Chebyshev paths, such as those listed in the Wyler '985 patent in column 4, lines 21–23 for a four-path system. However, only four nozzles and four transducers (not shown) are required to define these paths, rather than the eight nozzles and eight transducers used in the Wyler configuration. This halving of the number of ports and transducers, while retaining four paths tangent to the same circles as in prior-art GC quadrature flowmeters, promotes high accuracy but yields a substantial saving in manufacturing cost, and accordingly allows a substantial reduction in the price paid by the customer. Additional paths, which may be added for redundancy or other purposes, can include the diameter path, which may be considered as tangent to a circle of infinitesimal radius.

The illustrated paths need not utilize welded nozzles to define the transducer mountings, but may be implemented using thick-walled pipe (Schedule XXS pipe) having a wall thickness sufficiently above ¾ inch to allow the transducers to be directly mounted in threaded ports drilled and tapped in the pipe wall. In this case, the inner and outer pipe walls are turned concentrically, and tapered threaded holes (for receiving a transducer having a tapered pipe thread fitting) as shown in FIG. 24J, or straight-threaded holes with a faced off gasket sealing surface, are made at the desired angles through the wall of the pipe 105 to define the reflection paths between transducers. As illustrated schematically in FIG. 24K, the transducer mountings may be positioned to define reflected vee paths tangent to construction circles that range in normalized radius from 0.1 to 0.9, so as to interrogate different regions of the flow profile, and combine, with different weight to yield a more accurate measure. The construction circles may be equi-spaced, and may, for example, include the traditional midradius paths tangent to R/2. As noted above, preferably the refection point Q lies 5–30 degrees above the bottom of the conduit, and the transducers are all angled downwardly toward the reflector region. As discussed further below in regard to FIG. 33, the set of ultrasonic measurement paths may also include a diametral path to further enhance measurement accuracy. In general, these reflections may be made directly off the pipe inner wall, which may be smoothed or finished in the region Q to enhance reflection.

In a typical measurement situation, weights are assigned to the flow measured along each path for computing the total volumetric flow rate with the design of FIGS. 24H, I, FIGS. 32A–C, or FIG.33. The flow contributions obtained with the diameter path, if used, should be weighted by less than 15–20%, for example by about 10%, while at the same time the traditionally weighted GC path measurements should be weighted by greater than 80%, with 90% being preferred in one proposed configuration. Midradius paths, tangent to a circle of radius R/2, can be added to the four rotated GC paths illustrated above. If swirl is strong, another set of rotated paths, oriented oppositely, may also be provided so that averaging of the cw and ccw spiral paths cancels swirl effects common to both interrogations. In the side view, FIG. 24I, the paths are shown in their proper tilted configuration. Construction lines 309 and 809 are tangent to the construction circles in the end view FIG. 24H. The paths in the end view, in the fluid, begin and end at the intersections of the tangents to the construction circles and the pipe ID (inside diameter), i.e., the pipe interior wall. In this view a broken line symbolizes legs in the LHS, and centerline symbols represent the legs in the RHS. We further refer to the vee paths as rotated GC inboard or outboard, adapting known "inboard" or "outboard" notation for the earlier GC (Gauss Chebyshev) paths. The paths as shown would be undesirably sensitive to swirl and crossflow. Accordingly, one of several known compensation techniques is preferably applied. These may include one or more of: the use additional rotated vee paths, rotated in the opposite sense to those shown; the measurement, via flanges welded to the ends of pipe 105, of crossflow and swirl; or the measurement, within pipe 105, of the crossflow and swirl or circulation. In side view of pipe 105 there are also shown short segments of midradius and diameter paths denoted, respectively, 104MR1, 104MR2, 104DIA1, 104DIA2. We do not show these paths completely, in order to leave the diagram uncluttered. At the bottom of pipe 105 there is shown in phantom, a reflecting button 105BTN which is considered an option that may be advantageous if the pipe 105 is of small diameter, e.g. <100 mm diameter. It will be understood that this button can be of the same material as the pipe and welded thereto, or it could be another material having different reflective characteristics.

If the pattern of vee paths were duplicated elsewhere in the pipe, and two different button materials were used, then the ratio of echo amplitudes could be used to obtain the fluid density by the methods described above. Likewise the ratio of echo amplitudes could be obtained using the pipe 105 to yield a reference amplitude, and the reflection elsewhere could then provide the density-responsive echo. In the figure, the vicinity of the button 105BTN, on the inside of pipe 105, serves as a common reflection point for the four quadrature-related paths, or for the other suggested paths (midradius, diameter). Hence the button material and its internal finish could be selected to enhance resistance to corrosion and resistance to fouling. A titanium or SS button may serve these purposes well, and may be advantageous even in a pipe of large diameter made of less-expensive carbon steel.

While FIG. 24H illustrates the common refection point at the bottom of the pipe, applicant's preferred construction is one in which the entire set of paths are shifted (rotated) by a small angle clockwise or counterclockwise about the pipe axis, e.g., about five to fifteen degrees. This configuration assures that the reflector itself does not become submerged in sediment or condensate, and preferably also that the transducers or ports are directed downwardly and so they too are immune to collecting condensation, sediments or debris. The nozzle axes make angles of at least 15 degrees to the horizontal so they are self-draining. The vee paths not only double the axial projection of the path compared to a single leg at the same angle, but also sample flow on two sides of a dividing plane. The construction therefore yields an economy of construction, requiring half the number of nozzles, half the number of welds (in a welded construction) or other penetrations, and half the number of transducers. If the pipe is large enough (e.g. R above five inches) and the transducers ring down quickly (e.g., in under 100 $\mu$s) then the signals would arrive time-separated, and the N-banger method described in U.S. Pat. No. 5,515,733 (May 14, 1996) of L. Lynnworth may be utilized to reduce the number of required electrical channels to a single channel, with the transducers installed in the LHS paralleled electrically, and likewise the ones installed in the RHS.

Figure 24I:
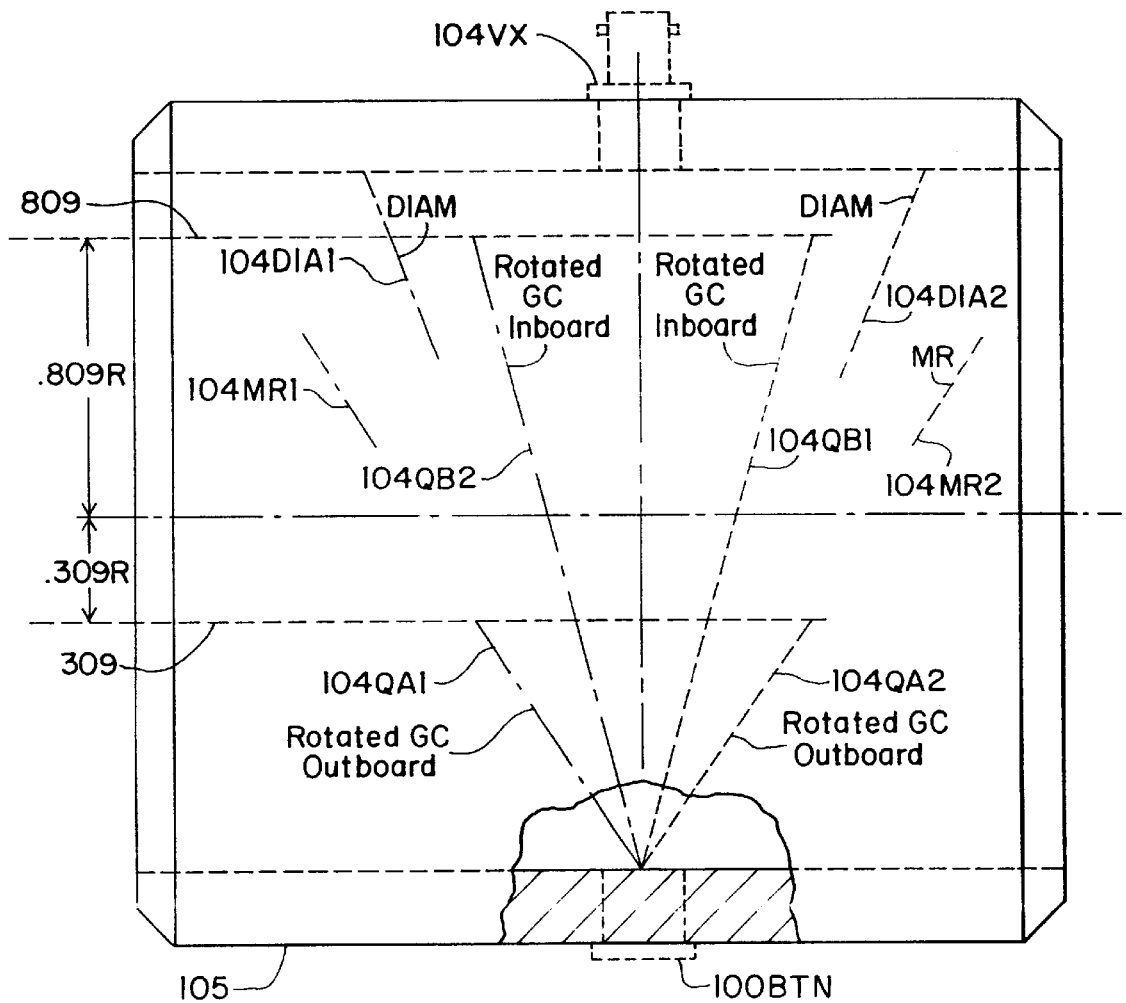
Figure 24J:
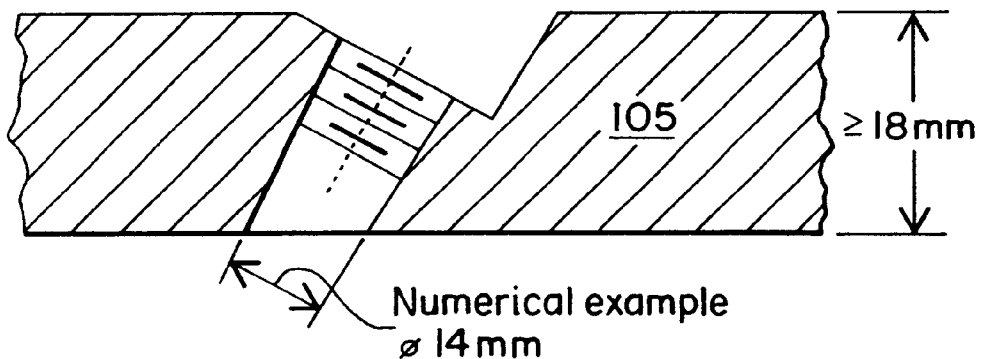
FIGS. 24J,K and L illustrate transducer mounting configurations for multipath systems.
Figure 24K:
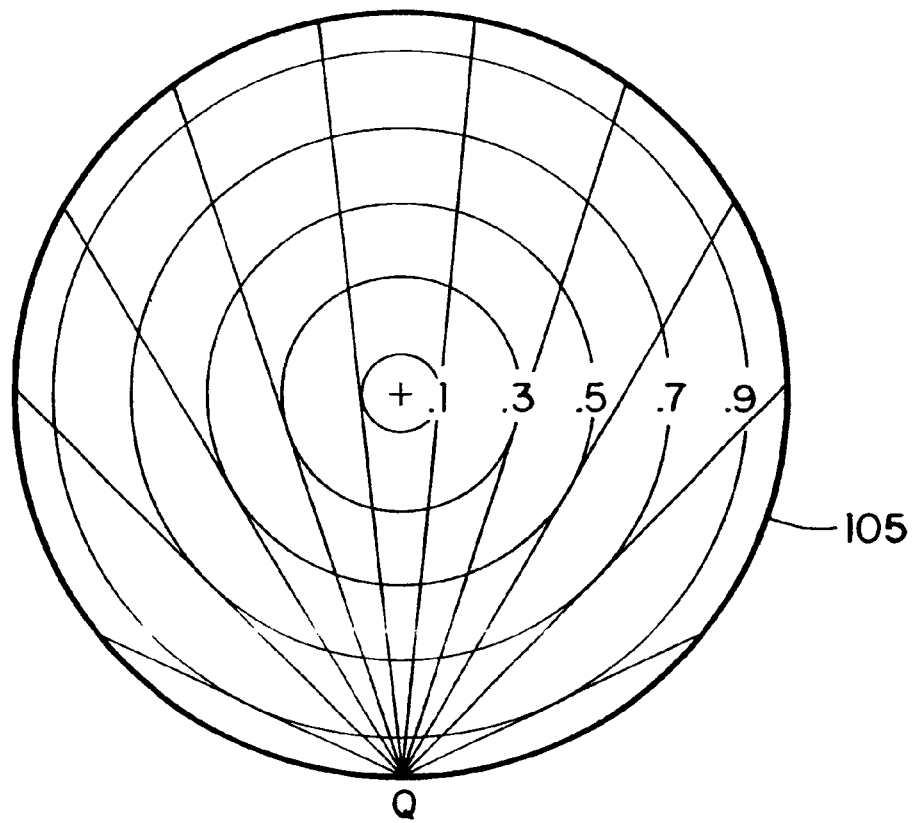

In the system of FIG. 24I, a reflective button 100BTN is shown in phantom at the position at the bottom where the path vertices coincide. This reflective element may be implemented as a face of another transducer assembly, whose inner face would be tangent to the pipe ID. At that spot it would receive contrapropagating single-traverse transmissions. This additional signal would then yield data on how much the crossflow or swirl changed in the regions just upstream or just downstream of its centerline. In this figure there is further shown, also in phantom to indicate its installation is optional, another transducer 104VX at the top and diametrically opposite the bottom button location. This pair of phantom transducers is effective to measure cross flow. Another pair, not shown, could sense swirl or circulation by the methods of FIG. 20, or by the technique described in the Lynnworth et al. *IEEE UFFC* September 1997 article cited above. The cross flow and swirl or circulation measurements may in some embodiment provide correction terms to the rotated GC path data. Further detail on such a button reflector construction appear below, in connection with FIGS. 32D–E.

Figure 24L:
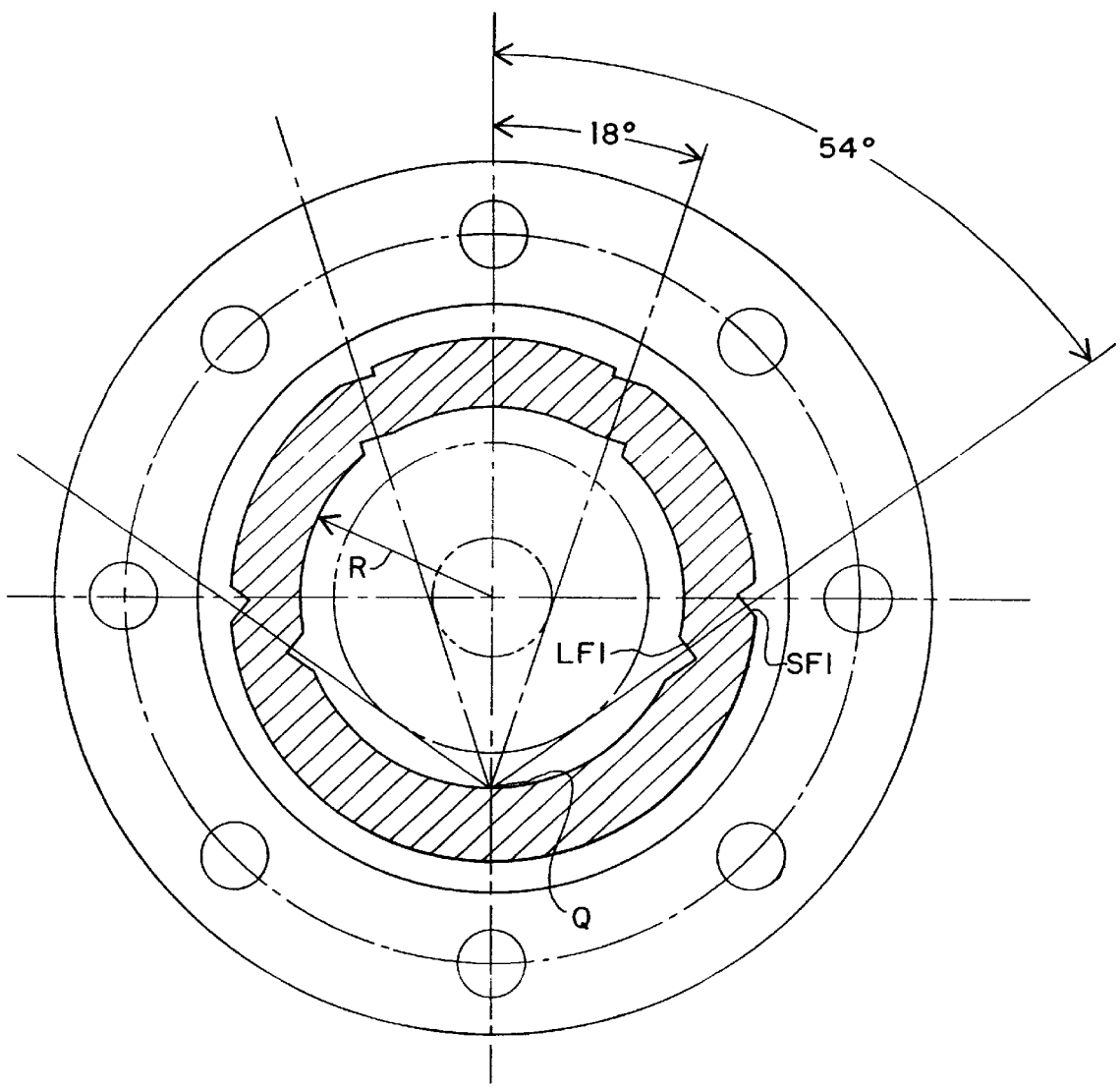

At this juncture, applicant also observes that the transducers employed for these reflective paths may, in certain circumstances, be clamp-on transducers that define effective measurement paths without requiring special nozzles or pipe penetrations. Specifically, applicant contemplates that the plate-like standoffs or coupling bodies shown in applicants' International Application PCT/US97/19238 may be mounted to define the interrogation paths through the fluid. That application, and its corresponding priority application, U.S. patent application Ser. No. 08/879690 are hereby incorporated by reference herein for their description of that "hockeystick" transducer coupler construction. FIG. 24L illustrates a end view partially in cross-section of a flanged spoolpiece suitable for use with such transducers or coupling asssemblies. As shown in FIG. 24L, the spoolpiece is constructed with a pipe segment of thick-walled pipe, wherein the external surface has been milled to define a seating face SF1 on the pipe surface that is perpendicular to the intended plane of the signal path and against which the transducer assembly is to be clamped. On the inner surface of the pipe wall, a corresponding lauching face LF1 has been counter-milled, so that the transducer signal exits the pipe wall directly along the desired tangent path to reflection point Q. The illustrated milled face angles correspond to the quadrature paths described above.

Returning now to the discussion of reflectance-based measurements, FIG. 25 is a side view of a steel, SS or Ti (titanium) spoolpiece 250 for conveying clean gas, for example, pressurized dry steam, and containing impedance matching material 251A, 251B, 251C, 251D at four specific internal locations, and four transducers 104A, 104B, 104C and 104D at four associated external locations. The impedance matching material, for use with steam, would be a high-temperature plastic, or graphite. The vee path illustrated makes one bounce off the opposite matching strip. If the transducers are axially separated a bit further, the path can be a W path, interacting twice with the opposite matcher and once with the same-side matcher, for a total of three reflective interactions. Note that a good matcher increases transmission into the steam, and increases the reflective sensitivity to steam density. Thus a good matcher kills two birds with one stone: overcomes some impedance mismatch and thereby increases signal strength, and then that signal is influenced more by fluid density, than for a poor matcher. These remarks apply if the transformed impedance is still high compared to the fluid impedance. To avoid crosstalk it may be advantageous to not use vee or W paths but rather, use paths that have an odd number of traverses, say three traverses. This would have two reflective interactions with the matching strip, roughly analogous to the two interactions obtained in FIG. 24 off the two small protrusions associated with triangular path $P_A$. This spoolpiece can operate with transducers like those of FIG. 25A.

FIG. 25A is an end view of the spoolpiece 250 of FIG. 25, to better show the strip matcher and transducer locations. The strips are shown installed in quarterwave-deep recesses, such that they end up flush with the general ID of the spoolpiece. They could also have been bonded in the same general areas, protruding inward a quarter wavelength or so. One syntactic foam used as a matcher has a thickness of ~0.52 mm, at the frequency f=500 kHz. This means the recess is not very deep, nor would the protrusion be very significant, if no recess were used. The protruding strip would satisfy the washed objective pointed out earlier. However, even though the protrusion is slight, there would still be some tendency for steam to lift it off, or perhaps in a cleaning cycle, mechanical or other means of cleaning might catch the strip and start it peeling away from the spoolpiece interior. Hence in this situation the recess that accommodates a flush-mounted matcher, may be the preferred solution, as long as the fluid is clean and not residue-bearing. In experiments we have found it convenient to produce the recesses by EDM (electric discharge machining). Depending on spoolpiece size (diameter and length), other machining methods may be more convenient or less expensive than EDM, e.g., broaching, shaping, milling.

If it were necessary to "wash" the strips that are located flush with the spoolpiece ID, a deflector (not shown) may be installed to catch a bit of the flow, diverting it to wash over the strip. In the case of clean fluids like dry steam, where washing is not necessary, the simpler deflector-free arrangement suffices. A SS deflector vane, when used to help wash the flush reflector of relatively low characteristic acoustic impedance (say 3 rayls), can also function as a reference reflector of high acoustic impedance (say 45 rayls). FIG. 25B illustrates further details of a notch placed in the pipe inner wall so as to radiate along a diameter path and also along an off-diameter or skewed path. In this case the notch is multi-faceted, giving rise to the two rays illustrated. If a side view were examined, it would show the notch as a pair of adjacent rectangles, the first one radiating along the (tilted) diameter, and the second along the tilted off-diameter chord.

Figure 26A:
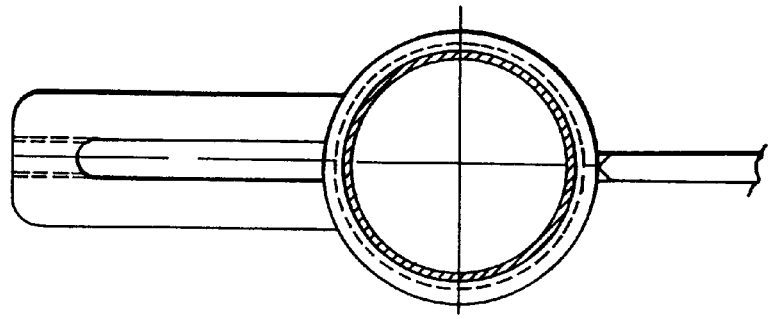
FIG. 26A is an end view of the pipe and transducers of FIG. 26, including a welded-on yoke that provides for easy transducer installation and removal, and a welded-on transducer for permanence.
Figure 26:
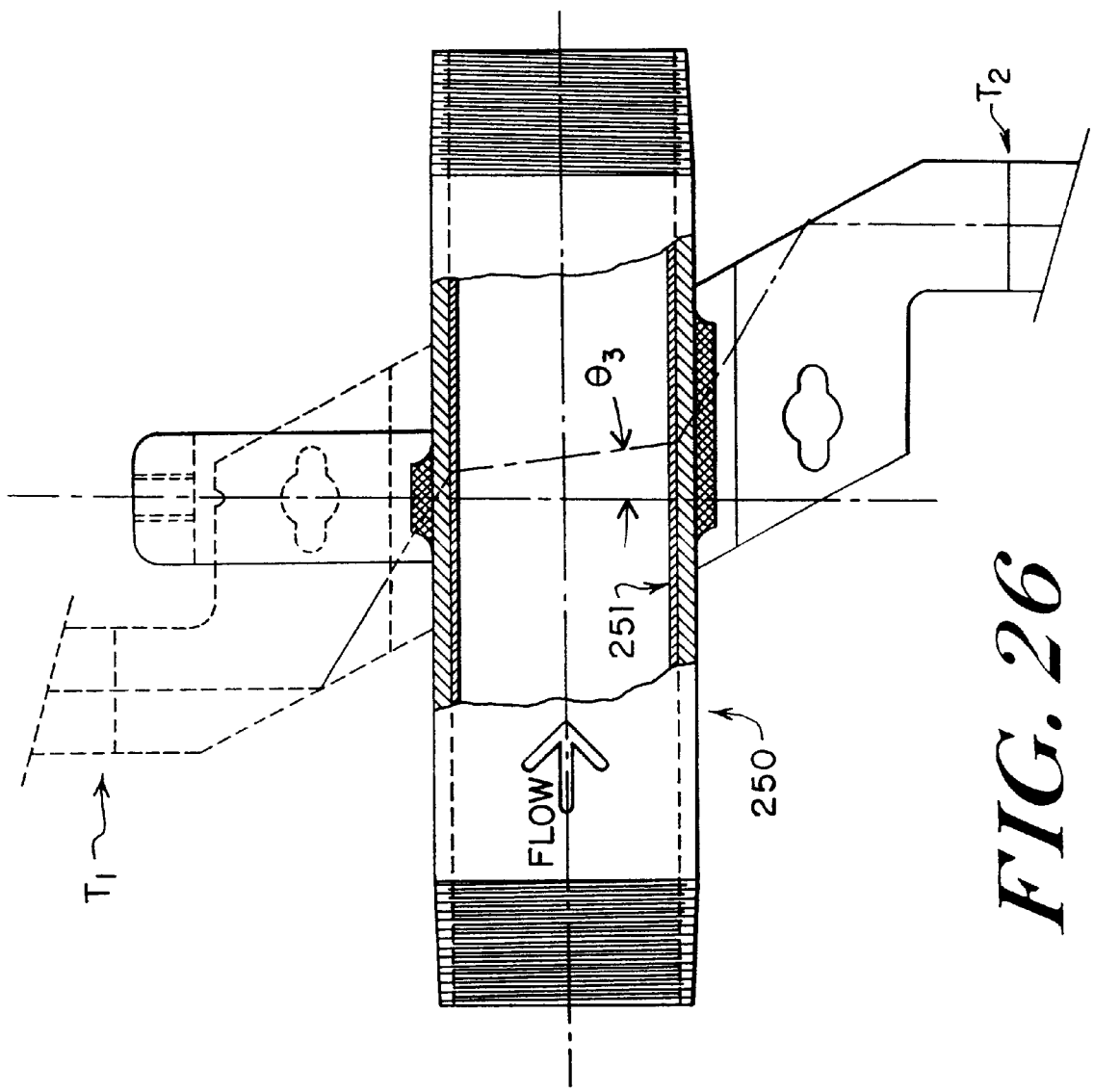
FIG. 26 is a side view of a spoolpiece lined with a quarter wavelength of impedance matching material, and containing at least two transducers on its exterior surface.

FIG. 26 is a side view of a pipe segment 250 lined with a quarter wavelength of impedance matching material 251. It contains at least two transducers T1, T2 mounted on or welded to its exterior surface. This construction has the advantage that virtually no preparation of the spoolpiece interior is required: no fixturing for EDM or the alternative machining methods for creating recesses a quarterwave deep. The interior, however, must be clean so that the lining can be well bonded to it. The lining can be centrifugally cast, or it can be bonded, as when the lining is a sheet or tube of plastic, epoxied in place, or adhesively connected using a suitable high-temperature bonding agent if the fluid is hot steam. Note that many steam applications occur at temperatures below 130 degrees C, so the requirements on plastics and adhesives are not great, and can be achieved at reasonable costs. To perform reliably on hot steam, at temperatures above 300 deg C. or higher, matcher material selection and bonding method are much more difficult. Here the costs may favor the small strip, as shown in the previous figure. Among the plastic materials currently known to be useful at elevated temperature and in particular, suitable for use in steam, one can cite: FDA EPR(ethylene propylene), and Greene Tweed's perfluoroelastomers CHEMRAZ® 605 & 615.

One of the best-known low acoustic impedance refractory materials is graphite. Graphite is available in many forms, with its porosity and grain structure contributing to its relatively low acoustic impedance. If the graphite has been nickel plated, then it can be soldered to steel, SS and even to Ti pipe if the Ti has also been nickel plated.

Figure 27:
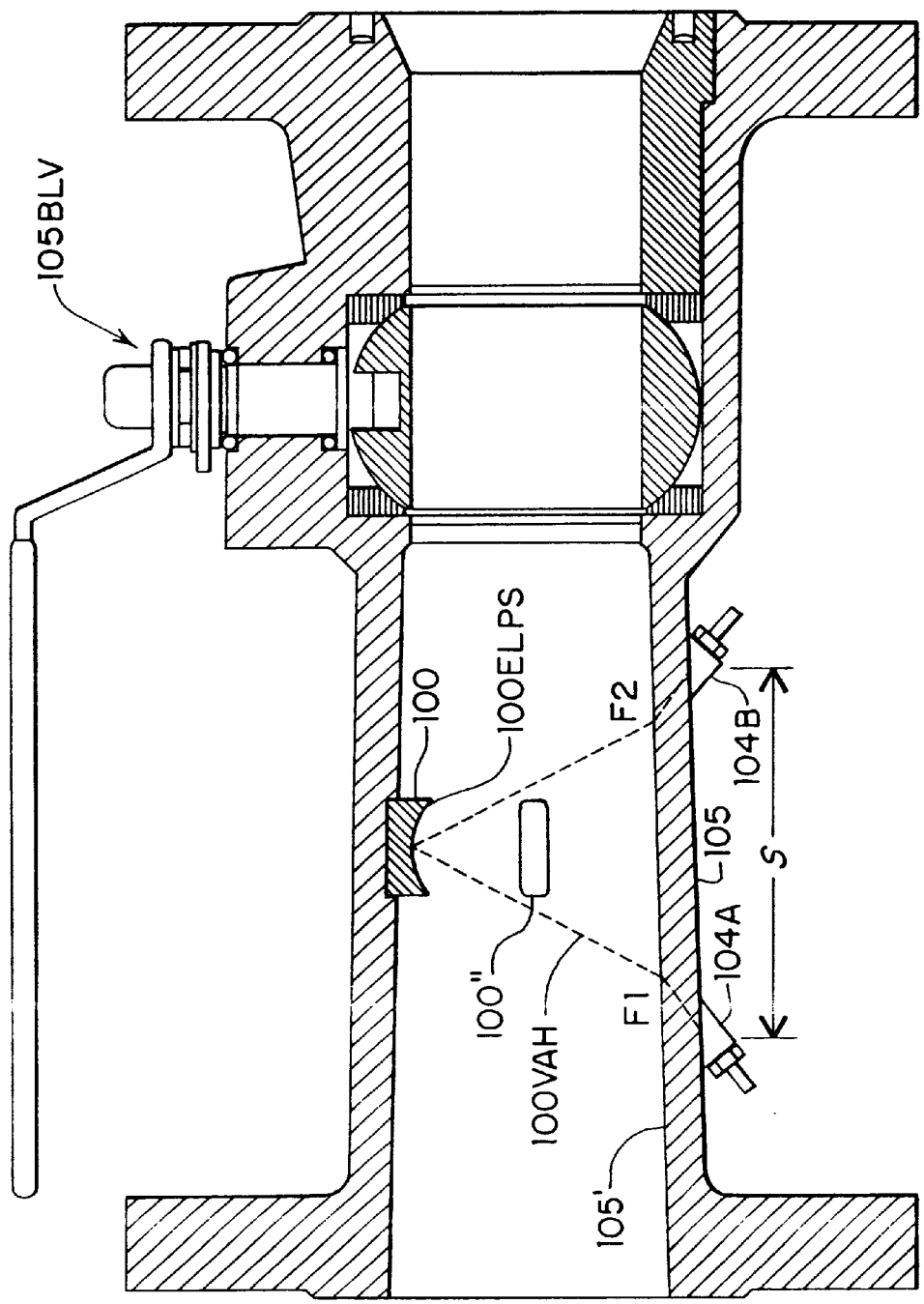
FIGS. 27, 27A and 27B show valve spoolpiece combinations containing a density-responsive reflector system and transducers for sensing the reflection coefficient and the flow despite the boundary being complicated and flow patterns being not fully developed.
Figure 28:
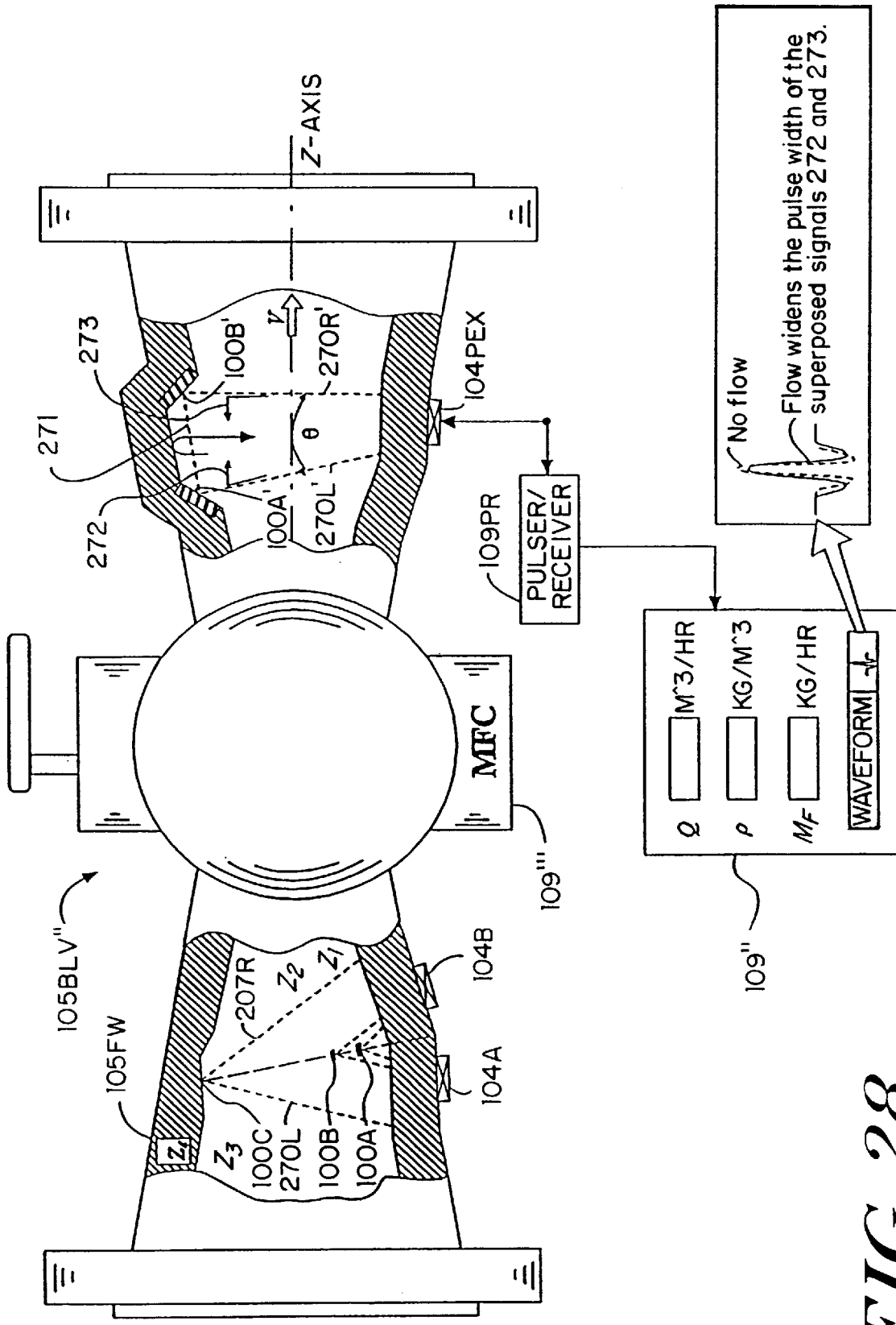
FIG. 28 is a section of pipe contains pairs of nozzled ports, each pair of ports being fitted with multipath transducers, diameter paths involving up to one reflection, and off-diameter paths involving at least one reflection.

FIGS. 27–28 illustrate applications of the foregoing principles to irregularly shaped regions as found, for example, in a valve. In an earlier patent (Lynnworth, U.S. Pat. No. 5,275,060, issued Jan. 4, 1994) vee paths were shown rather schematically, to indicate measurements of flow before, after, and in some cases right through the region of the valve body. FIG. 27 shows a ball valve 105BLV in which the inlet pipe 105 is tapered, as occurs in many commercial ball valves, such as the Jamesbury Type 530S valve. The tapered inlet creates a problem for conventional clamp-on transducers because the angles of the legs of a vee path are tilted such that vee-path symmetry is destroyed. However, by introducing a reflector 100 having a reflective surface running generally parallel to the inside surface 105' of the tapered inlet section, symmetry can be preserved. If the flow velocity covers so wide a range that beam drift could be a problem, then the reflective surface 100ELPS is preferably formed as an ellipse having as its foci, the two points where the refracted vee path 100VAA enters and leaves the fluid. This solution applies to bidirectional flow and can be used even if the inlet section were cylindrical, like a normal pipe, rather than tapered. A second reflector 100" is drawn at the center of the inlet section. This second reflector lies in a plane perpendicular to the plane of the paper and provides the second reflection coefficient, the first having been obtained from the first reflector 100. Thus we have again the basis for an A/B−1 solution, using transducers external to the pressure boundary and capable of measuring V as well as density, when used in conjunction with an electronic console such as console 109' shown earlier.

Figure 27A:
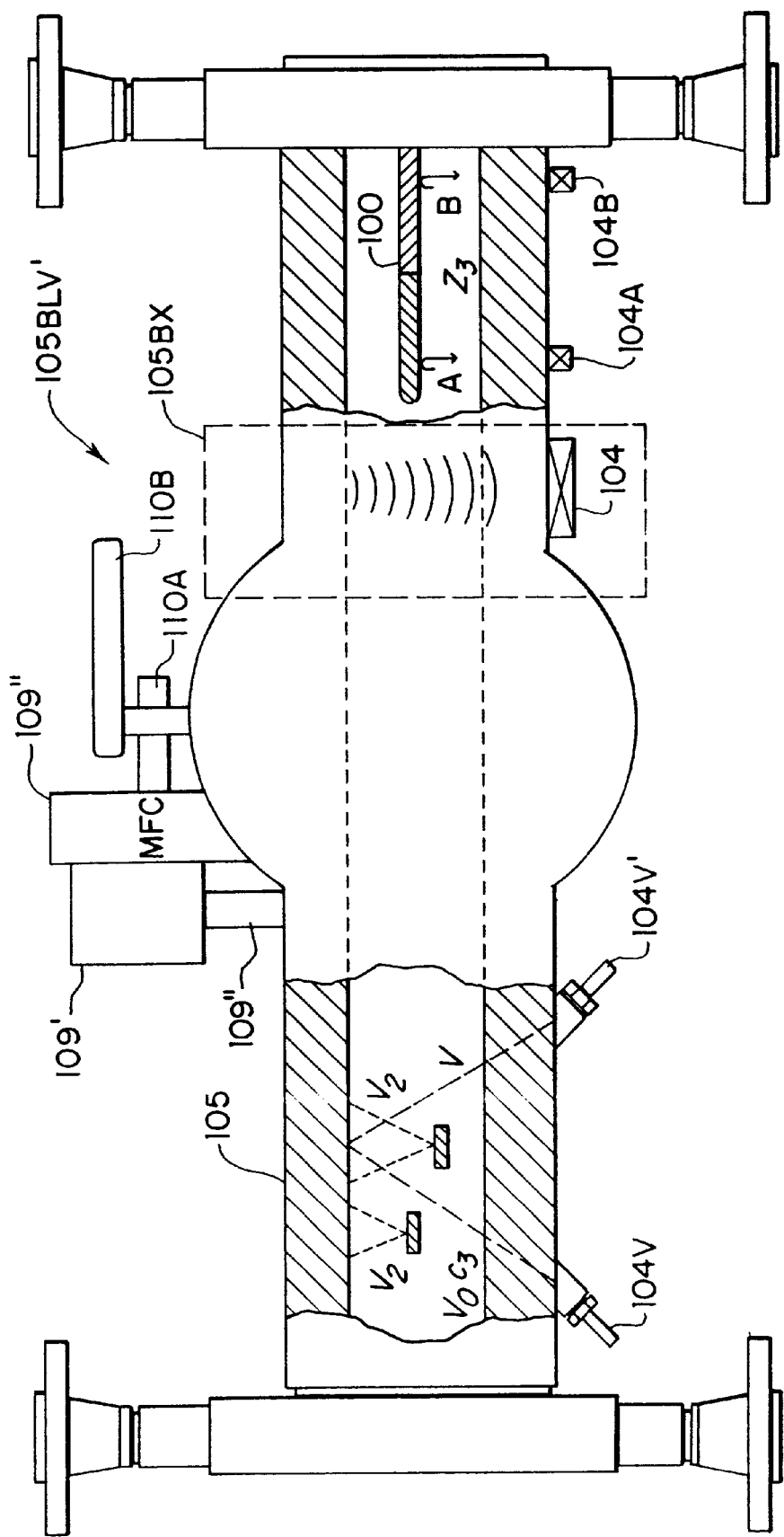

FIG. 27A shows another ball valve 105BLV, which for simplicity is drawn without tapered sections. It contains two internal reflectors, each like the ones in FIG. 1 or 6. External transducers like transducers 104V, 104V' communicate with the reflectors over noninterfering vee paths. The reflections provide the necessary timing and amplitude data for mass flowrate to be computed in electronic console 109 which is shown supported by a post support 109'. The console is connected mechanically and electrically to a mass flow controller 109''' that controls, by means of an actuator 110A, the flow through ball valve 105BLV. Collectively these achieve flow control aided by instantaneous feedback, and therefore superior to performance achieved manually by turning ball valve handle 110B. The sting 100 at the right indicates an alternate way of obtaining reflections. Inside the region enclosed by box 105BX there is still another way shown, for measuring flow velocity utilizing reflections. For clarity, this solution is shown enlarged in FIG. 27B.

Figure 27B:
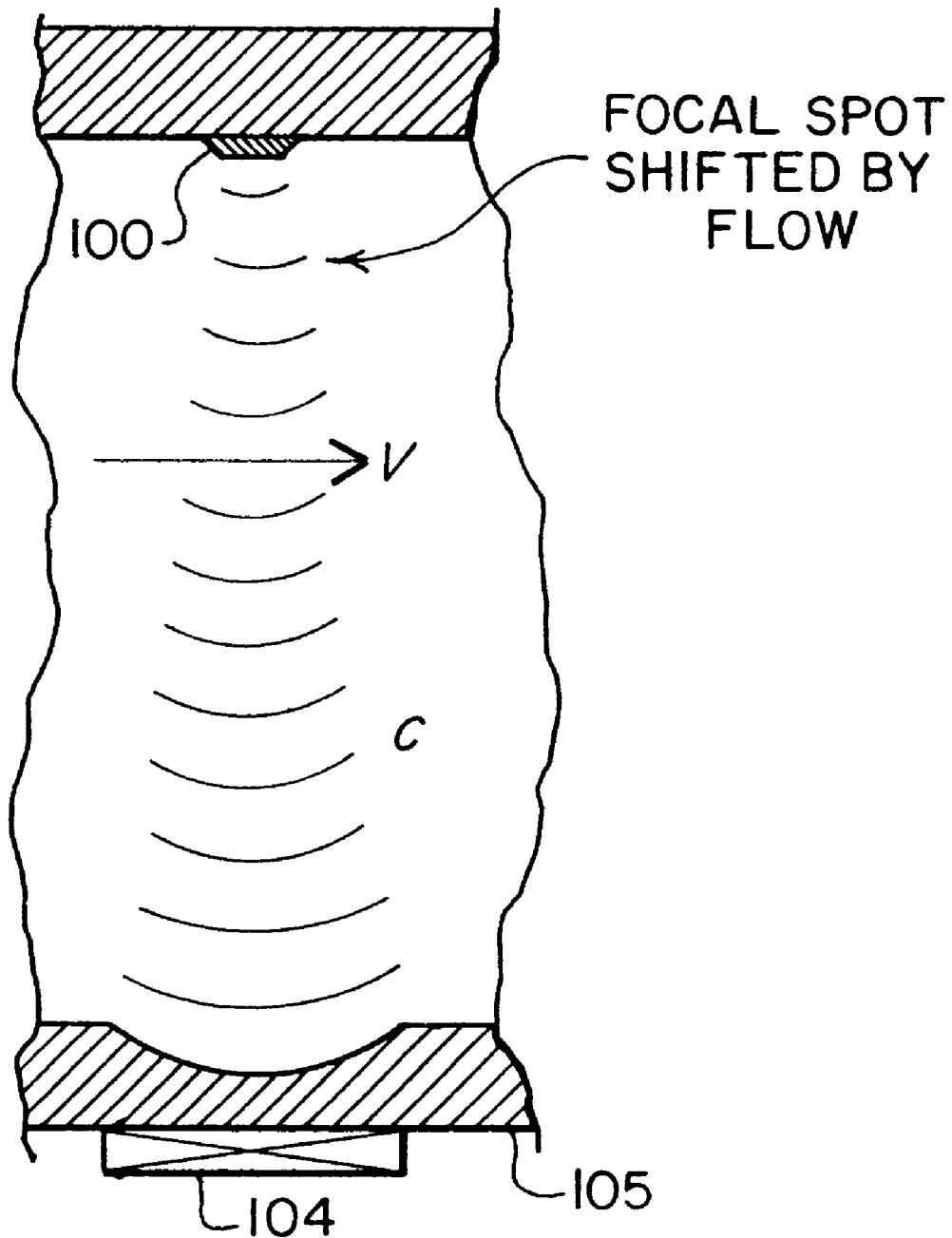

In FIG. 27B the transducer 104 is illustrated straddling a concave lens created in the wall of pipe 105. The lens causes the waves in the fluid to be focused at a point near the opposite wall, and preferably on the surface of a small projecting button reflector 100. If the fluid has a predetermined known sound speed, as would be the case if the device were designed for a particular liquid and for a narrow temperature range, then the system can be designed to focus sharply, to the order of a wavelength, on the target button. As a numerical example, if the ultrasonic frequency=2 MHz and the fluid is water near room temperature, $c \approx 1.5$ mm/$\mu$s and the focal spot size could be as small as about 1 mm in diameter. If the conduit diameter in this region is 100 mm, it is seen that at a Mach number of 0.01 (V=15 m/s) the beam would be nearly swept totally off the button. Thus a sensitive version of the beam drift flowmeter principle is obtained. The reference echo is obtainable by another unfocused transducer which receives echoes from the back wall even at V=15 m/s. The button can be combined with the elliptical reflector 100ELPS of FIG. 27 to provide density and flow data up to a maximum V.

FIG. 28 shows another ball valve 105BLV having an integral mass flow controller 109 and special reflecting and transmitting patterns machined into its tapered inlet and tapered outlet sections. These sections are positioned on either side of the valve mechanism contained within the spherical symbol containing the ball itself. Left of the valve mechanism small reflectors 100A, 100B in the freestream are interrogated by external transducers 104A, 104B along vee paths, as before. The reflectors are small enough so the first reflector 100A does not block the second reflector 100B, and the second does not block the vee path to the far wall 105FW. The far wall is notched by reflective notch 100C to restore symmetry about the centerline of the several vee paths. Right of the valve mechanism an external pulse-echo transducer 104PEX transmits a spreading beam into the fluid. Reflectors 100A, 100B lie within the spreading beam. Contrapropagating paths occur simultaneously, the paths including left and right legs 270L, 270R, respectively, having an angle between them. The resulting echo, detected in pulser/receiver 109PR is broadened slightly and requires analysis in the time or frequency domains in electronic flowmeter console 109 to extract information equivalent to $\Delta t$ in standard contrapropagation flowmeters.

FIG. 29 shows a compact folded-path flowcell embodiment comprised of upper and lower (top and bottom) portions 105TP and 105BM which may be brazed or otherwise sealably connected over their common face. The overall dimensions of this compact flowcell are indicated as x, y, and z. These may have numerical values such as 8" by 8" by 1" for a laboratory demonstration model, and perhaps half these values for spacecraft/satellite applications in zero g or microgravity environments. Piezoceramic transducers are drawn as split crystals 104XA, 104XB, 104XC and 104XD, connected electrically to console 105CE. The console has displays which, for example, might display flow velocities $V_{AB}$, $V_{CD}$, or a velocity derived by other combinations such as BC or AD, the generalized combinations being denoted $V_i$. This notation of the combinations is used to indicate that the interrogation occurred over a path between piezosegments having the corresponding A, B, C or D suffix.

The patterns in FIG. 29 may be considered as modules, connectable in series, or stacked, such that flow passes through each module, one after another, and further, that the sound beam is suitably reflected into the folded path of the next module. Then, according to sensitivity desired, as long as pressure drop and attenuation allow it, this construction can multiply severalfold, the sensitivity achievable per module. This will achieve a very cost effective enhancement solution if the modules are mass produced.

FIG. 29A is a simplified representation of the bottom of a two-part compact flowcell. The bottom plate 105BM has a passageway 105BMP milled out. The passageway could be ten mm wide by five mm deep, through which the fluid can enter and exit by tubing or other conventional means. When bonded to the mating plate, the passageway cross section becomes a ten millimeter square conduit. The top and bottom portions could each be made of Ti, as mirror images, and be brazed together. The acoustic path is shown comprised of four legs of length a, connected by shorter segments of length b. At the corners the ultrasonic signal wave is reflected by 45° reflectors. There are six such reflectors illustrated. We may refer to these as R1, . . . , R6.

An experimental model of the embodiment corresponding to FIG. 29A was constructed of an aluminum plate 8"×8"× ¾" thick with a 12.7 mm wide by 12.7 mm deep passageway, covered by a flat plate of lexan polycarbonate. In this model the lexan material for the top cover plate was selected because it is transparent and allowed applicant to observe the tendency for air bubbles to be trapped, and at the same time, allowed applicant to see what measures were successful in eliminating bubble entrapment. The milled passageway provided a total acoustic folded path slightly over three feet long, and it utilized fourteen (14) 45° reflectors. This 14 reflector geometry may be viewed as an enhancement of the doubling of the reflection coefficient's effect, as discussed above in connection with FIG. 3A, where that effect was obtained using corner reflectors. However, unless the corners are coated with plastic or other low c material, there is complete reflection at the 45° angle of incidence. At an ultrasonic frequency of 2 MHz, obtained by clamping Panametrics M106 contact transducers against an aluminum plate at the places where transducer symbols 104XC and 104XD are shown in the figure, good transmission was observed when the fluid was ordinary drinking water. Even at very low flow rates, good signals and easily detectable transit time differences were obtained. In this experimental model the path length p in the plate was ½ inch (12.7 mm). As seen in FIG. 29A, there is plenty of space between the four legs of path a. This means, a much longer path can be folded within the plate boundary illustrated. Again, in the experimental model, the liquid path was nearly one meter. This long path accomplishes several desirable objectives. It makes it easy to obtain accurate measurement of sound speed c in the fluid; it makes it possible to enhance the reflection coefficient principle if plastic or other sufficiently low sound speed material is introduced at a number of reflection points; it reduces the "end effects" where the fluid enters and exits the measuring channel, because the total acoustic path is so much greater than the passageway diameter. One may reasonably anticipate achieving a ratio of 100:1, using a one meter path and passageway dimensions of 1×1 cm. In the first tests the cover plate was merely screwed down. For later tests it was epoxied in place.

Using the split crystals, the bottom plate can provide the reference echo amplitude, and the top plate (in FIG. 29) can contain the plastic reflectors. In this way a very large difference in echo amplitudes can be obtained, to provide a sensitive measure of changes in fluid density. One way the reflectors could be made of plastic, is to make the entire upper plate of plastic, while keeping the bottom plate of metal. Each plate would be milled or formed with half the height of the passageway.

Since as many as 14 reflectors have been found practical, not as an upper limit, but rather, a value already demonstrated in 2 MHz lab experiments, to augment sensitivity, one may consider applying the reflection coefficient principle to measuring the density of gases. The transducers might have to be wetted, and isolated from one another (for example, by the O-ring flange sandwich method as illustrated in U.S. Pat. No. 5,515,733). Another solution is to subtract crosstalk electronically. One such electronic subtraction routine, which we may refer to as the A–B method, is described in the aforesaid U.S. Pat. No. 5,962,790 of Lynnworth and Liu. For gases, preferably the ultrasonic frequency is to be reduced to the 0.1 to 1 MHz range, depending on gas pressure and gas characteristics.

In a pulse-echo test the 14 reflectors were interrogated twice each at f=2 MHz, for a total of 28 interactions. The flow measurement is generally a one-way interrogation in each direction. The density measurement, however, can utilize a greater number of interactions at the reflecting surfaces, than does the flow measurement. The number of reflections demonstrated in this folded path prototype far exceeded the number utilized in earlier straight-path multi-bounce transmission, e.g., nine bounces shown in FIG. 6c on page 424 in Lynnworth's chapter 5 in Mason and Thurston (Ed.), *Physical Acoustics* 14 (1979).

FIG. 29B shows another embodiment of the folded-path multi-reflector aspect of the invention. Here the fluid is confined by a number of sections of square or rectilinear tubing, a cross section of which is depicted at cross section 105CS. One segment is denoted 105SG1. Segments can be thought of as being welded together at their ends, although other ways of fabrication are well known, e.g. in the microwave waveguide field. Note the use of many 45° corner reflectors, analogous to the corner reflectors R1, . . . R6 in FIG. 29A. The sections are drawn as if they lie in a first horizontal plane HP1, a second horizontal plane HP2, or in a vertical plane VP1, or in planes parallel to these reference planes. The idea is to make best use of available volume, and not be limited by the space between two physical obstacles such as a tank and a nearby engine. We can imagine a cube or other envelope surrounding the measuring sections. The total path of the folded system can obviously far exceed the edge dimension of such an envelope. Thus the folded path shown in FIG. 29A in one plane is extended to more than one plane (three, for example) in FIG. 29B.

FIG. 29B shows inlet and outlet tubing 105IN and 105EX, respectively, and shows a square transducer 104SQ having an area equal or similar to the internal cross section $D_X \times D_X$ of conduit cross section 105CS. The conduit wall thickness is w. The transducer can be round, as depicted by transducer 104RD. Transducers are connected to the flowmeter/densitometer console 105CE.

Among the disadvantages of the compact flowcell, one may list: pressure drop at high flow velocity; possibility of depositions forming if stagnant regions exist; bubbles from air or other gases coming out of solution could collect and block some of the signal. If the fluid is a gas of low sound speed, it becomes difficult to find a reflector with sufficiently low sound speeds, that there is some energy transmitted from gas into reflector. On the other hand, if the gas is of low molecular weight (if, for example, it is rich in hydrogen or helium) its sound speed may be above 1000 m/s, and plastics can certainly be found in which the velocity of at least one bulk wave (shear and/or longitudinal) has a sound speed comparable to or less than 1000 m/s.

Figure 30:
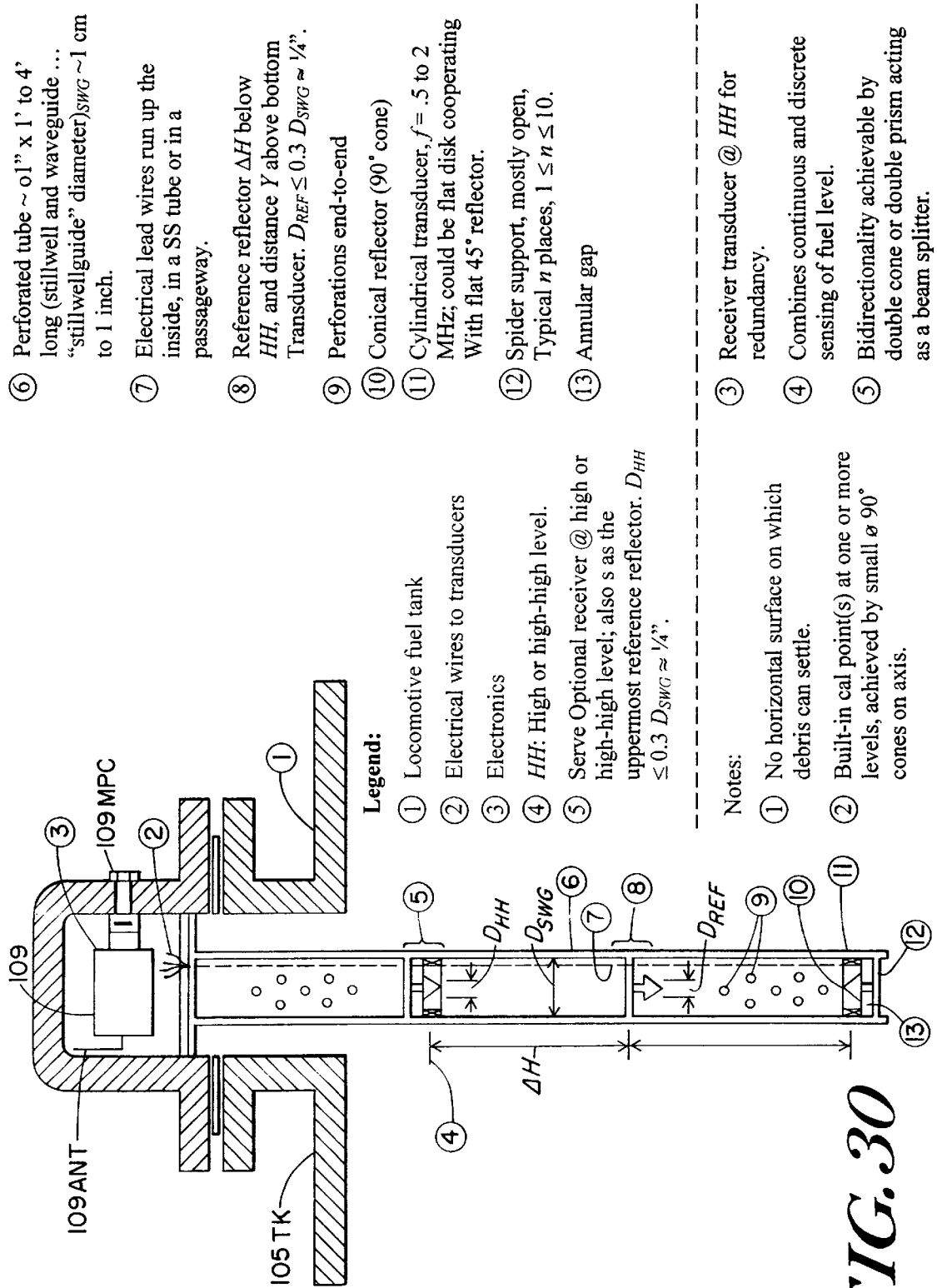
FIG. 30 shows a system useful for fuel management, overfill protection, optimizing refueling or fuel consumption rates and other such purposes, a density sensor combined with a liquid level measurement in a perforated stillwell; means for sensing density steps as well as evaluating the density of the major constituent such as diesel fuel on top of water, in a locomotive, shipboard or other vehicle fuel storage tank.
Figure 30B:
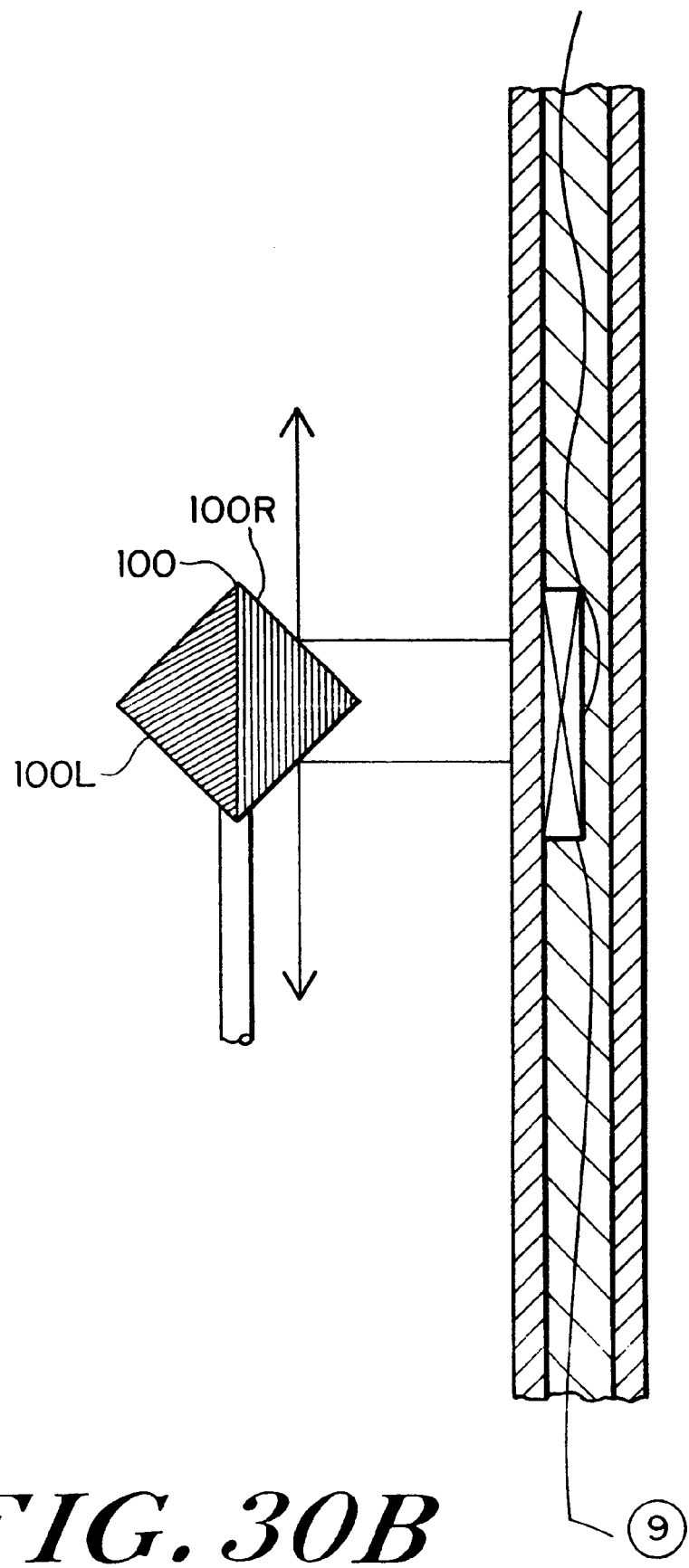

In FIGS. 30 and 30A we show liquid level sensing constructions, which including means to sense density at one or more locations based on differential reflectivity off a triangular reflector pointing downward like a plumb bob. The illustrated stillwell can be made of commercially available perforated tubing, one source being Perforated Tubes, Inc. of 4850 E. Fulton Street, Ada, Mich. 49301-9108.

FIG. 30 shows the 45° reflector operating bidirectionally, to obtain as a first measure of density distribution, the location of interfaces such as the water/fuel interface near the bottom of a (diesel) fuel storage tank, and the fuel liquid/vapor interface near the top of the tank. The accurate determination of (diesel) fuel density is achieved by the reflections from two differently-reflecting surfaces, as before, but within the confines of a stillwell. The electronics module 109 is contained within a standard explosionproof cap-like junction box. This box may include a wireless transmitting antenna 109ANT as well as a multi-pin connector 109MPC for controlling the filling and keeping track of withdrawals or consumption of fuel within tank 105TK. Wiring from the individual transducers passes up through a passageway along the inside (or outside) of the stillwell. A general description of this class of applications appears in Rountree and Berjaoui, U.S. Pat. No. 5,568,449. The pattern of a centralized reflector, shaped in side view as a square pattern with corners up and down, (◊) as illustrated, may be repeated at two or more levels within the stillwell. One site will be the highest level at which fuel is allowed to be present. This may be four inches (100 mm) from the inside top of the tank, or it may be defined as the height at which the tank volume would be 87% full, for example. Another site will be above the water level but near the bottom, perhaps corresponding to where the tank volume would be 20% full. From these two sites one can see that the vertical path would be comprised of fuel, the major constituent. Now if each reflector has a left side looking like<and a right side looking like>, the paths between transducers take the form of half-brackets, that is, ] for the left path and [for the right path. Let us take the right path [to be the reference path, which means the parts of the reflector participating in that path are metal and totally reflecting at the 45° inclined surfaces. Such 45° tilted surfaces shed debris, especially when subject to vibration as would occur when the tank is in motion, in a noisy environment, or if acoustic streaming were produced in the reflector vicinity, or if the stillwell were vibrated by electromagnetic or other means. Depending on the fuel composition, its density might be obtained simply and with moderate accuracy from the speed of sound sensed over the reference path [. Note that the square-on-its-corner reflector, allows some ultrasound to pass horizontally between transducers left and right of itself, if its corner-to-corner dimension is less than the height of the transducers. Transmission through fuel just beneath a reflector can be symbolized as follows: ___◊___. This provides a reference sound speed across the stillwell diameter. Then the height to reflecting interfaces can be obtained by proportion, with some correction for the vertical gradient in sound speed obtained from the horizontal samples across each reflector. In other words, (Distance to an interface)/(Stillwell inside diameter)=ratio of corresponding transit times, corrected by averaging horizontal transit times at the reflectors furthest apart and participating in the timing to interfaces. Absence of a horizontal signal indicates no fuel at that height. Thus the arrangement provides a simple discrete monitor of fuel height. The continuous monitor is obtained from interface echo travel times. Density is obtained from the ratio of echo amplitudes for the semi-bracket paths symbolized by ] and [. A further measure of fuel height is obtained in the immediate vicinity of the uppermost partially submerged reflector. As the fuel reaches this level, the signal amplitudes grow, both for the left path ] and the right path [, reaching their maxima as the fuel reaches the midpoint of the square-on-its-corner, ◊. We can symbolize this point as follows: ──◊──. This achieves locally continuous measurement of fuel height, useful in a feedback system, so fueling rate can be slowed down as the desired fill height is obtained. To provide a measure of the size of the elements, the flanged opening in a railroad diesel fuel tank, and in other cases where fueling occurs from a wayside or directly from a fueling truck, is often of diameter three inches (~75 mm). The height of the stillwell for a railroad locomotive would be around one meter. It could be shorter, just a foot or so, if interest was limited to the top region, just to prevent overfilling. On the other hand, for buried fuel storage tanks, if of a size that can be carried to a site on a truck, the tank, if cylindrical, will be around three to four meters in diameter (ten or twelve ft being common). The stillwell length for such cases will be comparable to the respective tank diameter. The reflector and associated transducers might be vertically spaced at one or two foot intervals (30 or 60 cm spacings). Transit time across the horizontal portions of such a stillwell, for a liquid having a sound speed=1000 m/s, would be, for a 75-mm path, t=(75 mm)/(1 mm/$\mu$s)=75 $\mu$s. From Rao's Rule, the vertical density gradient can be obtained from the sound speed gradient (as explained in Rountree and Berjaoui, for example), as a crosscheck on the density obtained from the ratio of composite reflection coefficients that involved reflectors at two different heights in the fuel, and hence subjected to two different densities. The density difference at the two heights depends on temperature, but temperature need not be measured. By analogy to four-path GC flowmeters, one could install four stillwells across a pipe such that the stillwell axes lay on GC paths. This would provide a quadrature method of measuring density, far too complex for most situations but perhaps useful if the fluid were extremely inhomogeneous in density and one required the area-averaged density. If the stillwells and flow-sensing paths both utilized the same off-axis locations, i.e., tangent to circles of normalized radii 0.309 and 0.809, then each stillwell "average" density, wall-to-wall, would be multiplied by the corresponding flow velocity, to obtain a chord-by-chord mass flow rate, subsequently to be weighted as in the traditional four-path GC method (Wyler, for example). This provides one specific example of multiplying a density distribution by a flow distribution, to yield an accurate mass flow rate, despite complexity in the distributions of flow and/or density.

While operation of the stillwell containing 45° reflectors is described within the confines of a fuel storage tank, the same stillwell and its sensors can be installed through a flanged opening in pipe in which fluid flows, but where the pipe is not always full. This falls in the class of problem for which flow meters are available under the designation "area velocity" flow meter. Now, however, with the added feature of density sensing, the solution can be enhanced and can be referred to as "area •velocity•density" mass flow meter.

To isolate the transducers and wiring from exposure to fuel or other liquids in the tanks for which this device is designed, a perforated dewar arrangement is shown in FIG. 30A.

Basically the design is the same as in FIG. 30 except the stillwell is of double-wall construction with multiple sealed holes through both walls. This is achieved by welding-in short lengths of tubing, to allow equilibration of liquid inside and outside the stillwell. The stillwells in FIGS. 30, 30A do not sit on the bottom of the tank. Rather, they are suspended from the flanged opening at the top. The datum is the seal face of the flange on the tank nozzle.

Figure 31A:
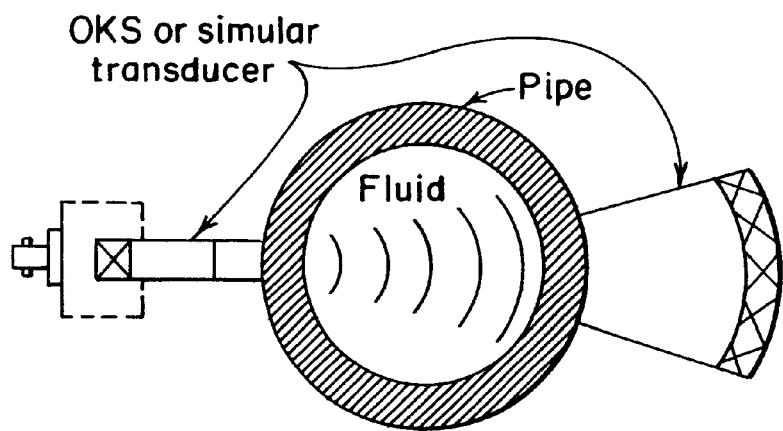
FIG. 31 shows clamp-on transducers to improve SNR (signal to noise ratio) for the velocity-sensing portion of a clamp-on transducer mass flowmeter that uses the differential reflection coefficient method with a locally plastic-coated metal to sense liquid density.
Figure 31B:
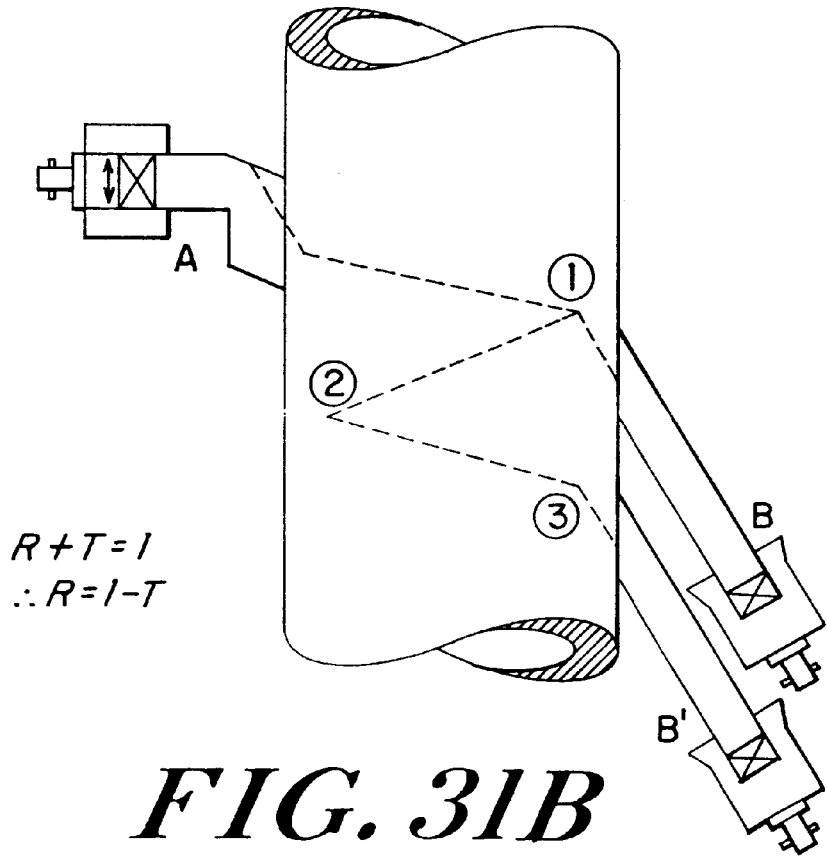

FIG. 31 shows the measurement of transmitted signals that have bounced off reflective portions of a pipe twice or not at all. They are picked up at two axially-displaced locations by receiving transducers B & B'. The shear wave transducers in this diagram are polarized either along the z-axis or in a plane perpendicular to z. This arrangement has been found to reduce interfering crosstalk.

Figure 32:
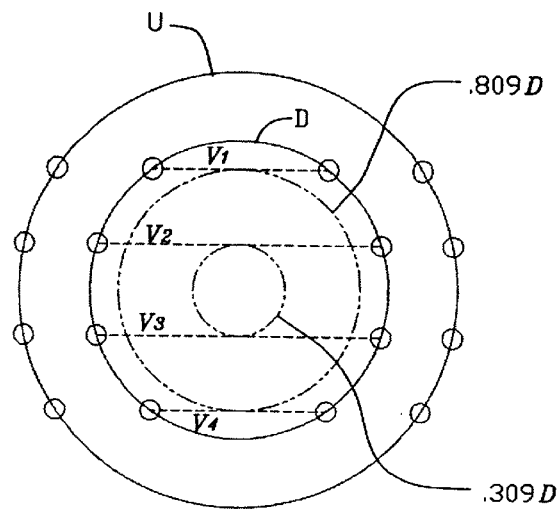
FIG. 32 illustrates a prior art Gauss-Ch000ebysheff path configuration.
Figure 32A:
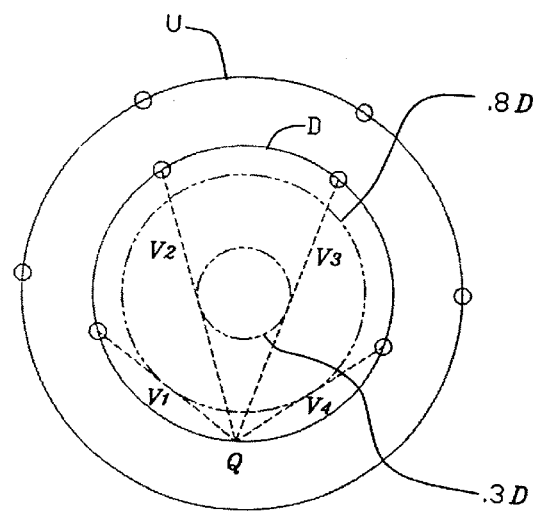
FIGS. 32A–32E illustrate novel flow-integrating reflective path interrogations of the present invention.
Figure 32B:
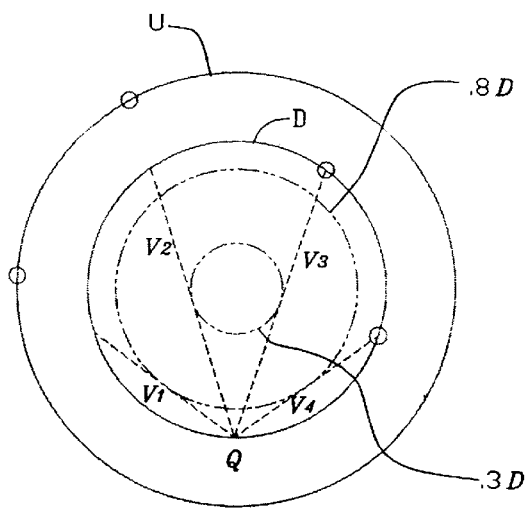
Figure 32C:
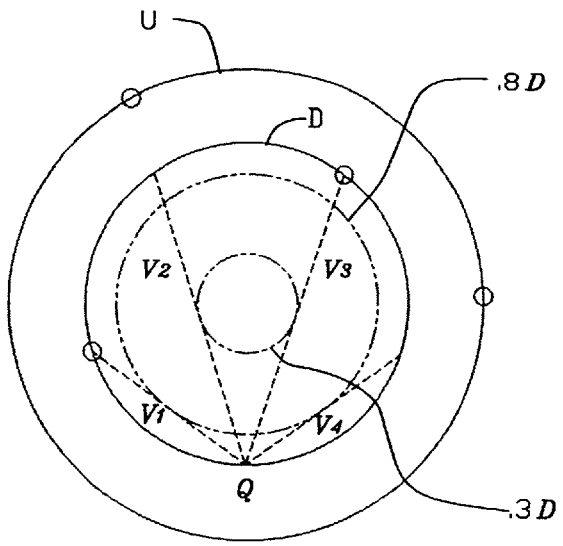
Figure 32D:
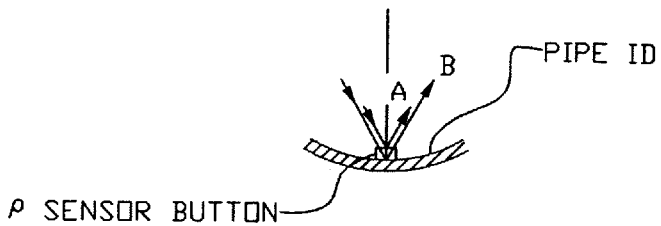
Figure 32E:
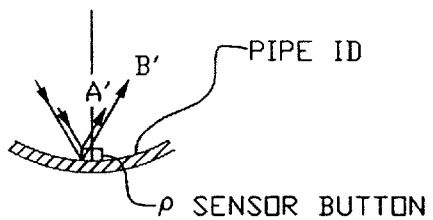

The reflection method of the present invention may also be seen to offer interesting improvements over other prior art systems. By way of example, FIG. 32 illustrates a conventional set of Gauss-Chebyshev (GC) paths, taken in four planes, two each being tangent to either a concentric cylinder of 0.309D or one of 0.809D. In the prior art the path measurements are combined with weights to yield the average flow through the conduit cross section. FIG. 32 schematically illustrates the placement of eight upstream and eight downstream transducers (on the circles designated U and D, respectively), needed for a general set of GC path measurements. However, applicant has realized that one may employ other tangent planes to these cylinders, and take these measurements along skew planes, similar to the configuration of FIG. 24H above, and directed at a common reference reflector region. This allows one to utilize the same GC weights, and reduce the number of required transducers. FIGS. 32A–32C illustrate representative systems of this type. The system of FIG. 32A uses only eight transducers. If the secondary flow components are known, or are known to be small, then as few as four transducers, arranged as in FIG. 32B or 32C, will suffice. The bounce averages both inboard paths $V_2$ and $V_3$, and both outboard legs $V_1$ and $V_4$. FIGS. 32D and 32E illustrate details of the reflective path using a pipe wall reference and a ρ sensor button at the common reflecting region Q. FIG. 33 illustrates a system like that of FIGS. 32A–C, showing end views of the two sets of nozzles.

The foregoing systems may be adapted to diverse measurement needs. Thus in addition to the broad constructions enumerated in the claims, the invention includes specific systems as described above as well as numerous simple adaptations to know measurement systems. The invention includes a multiply reflected sensing system wherein the ultrasonic path is folded into n linear segments each of axial length $L_{ax} > 2D$ where D=segment hydraulic diameter, $4 \leq n \leq 32$ with a total folded path length $10D_{HYD} \leq P-F \leq 100D_{HYD}$. In this case, the linear segments may, for example lie in or parallel to any one of three orthogonal planes, and at least one 45° reflector lies serially adjacent linear segments. The invention includes special reflectors, such as a differential vee block, which provides two reflective regions, one being totally internally reflecting within the fluid, and the other providing a substantially attenuated echo responsive to fluid density. It includes systems in which a multipath flowcell has at least two different paths between two axially separated transducer assemblies, and wherein the axial projection of the two paths are equal to within the axial dimensions of the smaller of the two transducer assemblies, and one of the paths traverses one or more tilted diameters, while the other of the paths traverses an off-diameter spiraled path whose projection in a plane perpendicular to the longitudinal axis of the multipath flowcell is a regular geometric figure having three to nine vertices. A preferred rotated gGauss-Chebyshev implementation defines paths tangent to circles of radii approximately 0.309R and 0.809R where R is the pipe radius, and wherein all the transducer nozzles point downward such that their axes make an angle with the horizontal of at least 15°, and preferably are directed to a reflector that is oriented oblique to the horizontal direction to shed material which may deposit thereon. When transducers and reflectors are arranged to produce rotated GC paths, these may include inboard paths utilizing clamp-on transducers and outboard paths utilizing wetted transducers, and the reflection region Q may include a protruding button of different impedance than the pipe to provide a timewise distinguishable echo that provides data on fluid density. The inboard vertex and an outboard vertex may be arranged so the vertices are staggered, and the system may provide additional paths in the vicinity of the rotated GC paths, configured to resolve orthogonal components of flow. When a reflector button is used, it may be configured to produce an echo distinguishable from a pipe echo, and the processor may include a processing module effective to perform at least one of the processes of deconvolution, reference echo correlation and frequency filtration.

This completes a description of a basic embodiment of the invention and a number of variations, construction details, and applications to sensing and measurement problems and systems. The invention being thus disclosed, variations and modifications thereof will occur to those skilled in the art, and all such variations and modifications are considered to be within the spirit and scope of the invention, as defined by the claims appended hereto and their equivalents.

What is claimed is:

1. A sensing system for determining a physical property of a fluid, wherein the system performs measurements of an ultrasonic signal propagated through the fluid to a reflector in the fluid and includes at least one differential impedance fluid reflection path measurement wherein the ultrasonic signal propagates along a differential path in said fluid effective to determine a value of fluid impedance locally at the reflector.

2. A sensing system according to claim 1, wherein the differential impedance fluid reflection path measurement is performed by reflecting signals from a reflector formed of a high acoustic impedance material having an impedance matching surface.

3. A sensing system according to claim 1, wherein the impedance matching surface is a quarter wave layer of low Z material.

4. A sensing system according to claim 1, wherein the differential impedance fluid reflection path measurement is performed by reflecting signals from a reflector having a high impedance portion and a low impedance portion.

5. A sensing system according to claim 4, wherein the reflector is a vee block, a sting, a conduit liner or insert.

6. A sensing system according to claim 4, wherein the differential impedance fluid reflection path measurement is performed by reflecting signals from two reflectors positioned close together along an ultrasonic signal path.

7. A sensing system according to claim 1, wherein the differential impedance fluid reflection path measurement is performed by reflecting signals from a reflector positioned at a region of representative flow.

8. A sensing system according to claim 1, using at least two reflections obtained from one or more wetted reflectors positioned along one or more signal paths and in contact with the fluid, wherein the reflectors differ in at least one of: characteristic acoustic impedance; protrusion distance into fluid; and reflector shape.

9. A sensing system according to claim 1, which is an ultrasonic mass flow rate measuring system that determines fluid density by processing ultrasonic signals reflected off two different reflectors.

10. A sensing system according to claim 1, configured with a single transducer or a single reflector to yield ultrasonic data on density and flow velocity.

11. A sensing system according to claim 1, wherein a multiplicity of transducers are mounted to interrogate a reflector system from regions outside a pressure boundary and determine symmetry and homogeneity of fluid inside said pressure boundary.

12. A sensing system according to claim 1, having a first elastic member operated in resonance to transform acoustic impedance of a second elastic member from a relatively high value substantially greater than 10 Mrayls, to a lower value on the order of 3 Mrayls.

13. A sensing system according to claim 1, wherein two reflecting surfaces provide two echoes corresponding to two reflection coefficients having respectively values R1 & R2, greater than and less than, that from a reflector of characteristic acoustic impedance equal to an acoustic impedance set point, wherein magnitudes of the two echoes are adjusted electronically to produce a null when the fluid impedance equals a set point impedance.

14. A sensing system according to claim 1, configured as a density measuring system for a multicomponent fluid system such as a tank containing fuel and water, and wherein steps in density are located by reflections from the interface between fluids of different impedance and further including means to sense the density of the major constituent in the multicomponent fluid.

15. A sensing system according to claim 1, configured with a folded path containing at least ten reflections at angles between 30° and 75° and lying beyond the critical angle for total internal reflection, optionally wherein a number of said reflections are damped by coating a reflector substrate possessing a high sound speed with a slower coating.

16. A sensing system according to claim 1, using at least two reflections obtained along one or more signal paths from a wetted reflector positioned in contact with the fluid, wherein the wetted reflector has differing reflectivity for shear and longitudinal waves.

* * * * *